US006258827B1

(12) United States Patent
Chenard et al.

(10) Patent No.: US 6,258,827 B1
(45) Date of Patent: *Jul. 10, 2001

(54) COMBINATIONS FOR THE TREATMENT OF PARKINSONISM CONTAINING SELECTIVE NMDA ANTAGONISTS

(75) Inventors: Bertrand L. Chenard, Waterford; Frank S. Menniti, Mystic, both of CT (US)

(73) Assignee: Pfizer Inc., New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/930,599

(22) PCT Filed: May 26, 1995

(86) PCT No.: PCT/IB95/00398

§ 371 Date: Oct. 10, 1997

§ 102(e) Date: Oct. 10, 1997

(87) PCT Pub. No.: WO96/37226

PCT Pub. Date: Nov. 28, 1996

(51) Int. Cl.⁷ ........................ A61K 31/445; A61K 31/195
(52) U.S. Cl. .................. 514/327; 514/327; 514/315; 514/565; 514/567
(58) Field of Search ................................. 514/327, 565, 514/567

(56) References Cited

U.S. PATENT DOCUMENTS

| 5,272,160 | 12/1993 | Chenard | 514/327 |
| 5,356,905 | 10/1994 | Butler | 514/320 |
| 5,654,302 | 8/1997 | Chenard | 514/235.5 |

FOREIGN PATENT DOCUMENTS 0517347   9/1992   (EP) .

OTHER PUBLICATIONS

The Merck Index, 11th Edition, Merck & Co., Inc., #1802, 1989.*
Greenamyre and O'Brien, Arch Neurol., 1991, 48, 977.
Greenamyre et al., Annals of Neurology, 1994, 35, 655.
Williams et al, Neuron, 1993, 10, 267.
Monyer et al., Science, 1992, 256, 1217.
Greenamyre, Journal of Neural Transmission, 1993, 91, 255.

* cited by examiner

Primary Examiner—Theodore J. Criares
Assistant Examiner—Jennifer Kim
(74) Attorney, Agent, or Firm—Peter C. Richardson; Gregg C. Benson; Robert T. Ronau

(57) ABSTRACT

This invention relates to a method of treating Parkinson's Disease whereby a mammal suffering from Parkinson's Disease is treated with a combination of a forebrain selective NMDA antagonist and a compound which is capable of increasing the excitatory feedback from the ventral lateral nucleus of the thalamus into the cortex. This invention also relates to pharmaceutical compositions containing the synergistic combination.

5 Claims, No Drawings

COMBINATIONS FOR THE TREATMENT OF PARKINSONISM CONTAINING SELECTIVE NMDA ANTAGONISTS

CROSS-REFERENCE TO RELATED APPLICATION

This application is the National Stage under 35 U.S.C. §371 of copending International Application No. PCT/IB95/00398, filed May 26, 1995, entitled "Synergistic Treatment for Parkinsonism."

BACKGROUND OF THE INVENTION

This invention relates to the field of treating Parkinson's Disease (also termed parkinsonism). Specifically, this invention relates to the treatment of mammals suffering from parkinsonism which comprises administering to said mammal a synergistic amount of a forebrain selective N-methyl-D-aspartate (hereinafter NMDA) antagonist and a compound capable of increasing the excitatory feedback from the ventral lateral nucleus of the thalamus into the cortex, such that the balance of the excitatory feedback from the ventral lateral nucleus of the thalamus into the cortex in said mammal suffering from Parkinson's Disease is restored.

Parkinsonism is an insidious disease characterized by symptoms including progressive tremor, bradykinesia and rigidity. The disease can be fatal within 5–10 years of the onset of symptoms. The underlying cause of Parkinson's disease is the degeneration of the dopaminergic neurons in the nigrostriatal pathway. These dopaminergic neurons are part of a neuronal feedback circuit for the control of motor function. The degeneration of these neurons results in toxic changes in the activity of several of the neuronal pathways in this motor circuit. The outcome of these changes is a significant decrease in feedback from the ventrolateral thalamus to the premotor cortex. This loss of feedback engenders the motor symptoms of the disease.

The only successful treatment for parkinsonism to date is levodopa therapy. Levodopa is a dopamine precursor. Therapy with this agent partially restores the loss of dopamine in the striatum which results from the degeneration of the nigrostriatal dopaminergic neurons. The use of levodopa has greatly improved the quality of life and the life expectancy of patients suffering from parkinsonism. However, the use of levodopa to treat parkinsonism suffers from drawbacks. Levodopa is now most often administered with a levodopa decarboxylase inhibitor such as carbidopa or benserazide. This prevents the conversion of levodopa into dopamine outside of the central nervous system and further improves the benefit/adverse effect ratio of this therapy. Nonetheless, levodopa therapy treats only the symptoms of the disease and does not slow or avert disease progression. Further, the beneficial effects of levodopa therapy on the motor symptoms of the disease decline within several years of beginning treatment. This reduced efficacy is also often accompanied by development of severe dyskinesias and levodopa-induced confusion, hallucinations, paranoia and delirium. Clearly there is a need for a new therapeutic strategy which provides enhanced treatment of the symptoms of parkinsonism and at the same time reduces the side effects which limit the current therapy.

Other approaches are under consideration to treat Parkinson's disease. Some of these approaches aim to replace the loss in dopamine function in the striatum. These include: dopamine receptor agonists including dopamine D1 receptor agonists, dopamine D2 receptor agonists, dopamine D5 receptor agonists, and dopamine/opiate receptor agonists; dopamine uptake inhibitors; tyrosine hydroxylase stimulants; monoamine oxidase inhibitors and monoamine oxidase-B inhibitors; and COMT inhibitors. Still other therapies under consideration are directed at restoring the feedback from the ventrolateral thalamus to the premotor cortex by a variety of mechanisms. These include: AMPA antagonists, GABA agonists, aminergic receptor agonists, muscarinic receptor antagonists, adenosine regulating agents, opiate receptor antagonists, LDH stimulants, CCK receptor agonists, CCK receptor antagonists, adrenoreceptor agonists, IL-1 antagonists, growth factors, antiinflammatory agents, antioxidants, immunostimulants, serotonin reuptake inhibitors, and aminergic reuptake inhibitors. However, while some of these approaches show promise based on animal studies, none of these treatments have yet proved effective in Parkinson' disease in man.

Chenard, in U.S. Pat. Nos. 5,185,343; 5,272,160 and 5,338,754, all three of which are incorporated herein by reference, discloses that compounds of the formulae

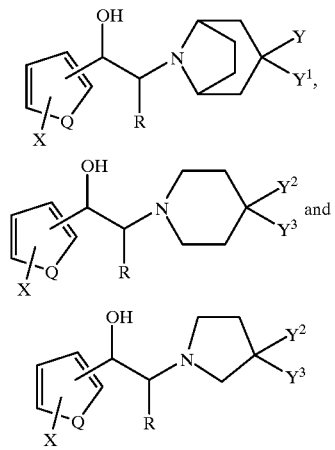

are NMDA antagonists and as such have utility in the treatment of Parkinson's Disease.

Butler, in U.S. Pat. No. 5,356,905, also incorporated herein by reference, discloses that compounds of the formula

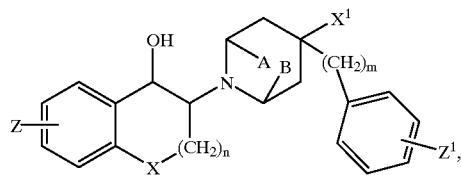

are NMDA antagonists and as such have utility in the treatment of Parkinson's Disease.

The NMDA antagonists disclosed by Butler and Chenard, when tested in the screen disclosed in Williams et al., Neuron, 10, 267–278 (1993) are shown to be NR2B subtype selective NMDA antagonists. Those skilled in the art are well aware that the terminology "NR2A", "NR2B", "NR2C" and "NR2D" is used to describe NMDA receptors in the rat and that similar receptors exist in other mammals, including humans, which are named differently.

The present invention teaches that forebrain selective NMDA antagonists which are selective for receptors containing the NR2B subunit also act synergistically with levodopa to reverse motor deficits in animal models of Parkinson's disease. The NMDA receptor is comprised of an NR1 subunit in combination with one or more of an NR2 subunits, NR2A, NR2B, NR2C, or NR2D. (Monyer et al., Science, 256, 1217–1221 (1992)). An NR2B selective NMDA antagonist is an agent which has been found to inhibit NMDA receptor function for receptors containing the NR2B subunit but is less efficacious at NMDA receptors which lack this subunit. To date, only non-selective NMDA antagonists have been reported to act synergistically with levodopa in animal models of Parkinsonism. Examples of non-selective NMDA antagonists are MK801, CGS-19,755, or CNS-1102. The present invention teaches that it is the NR2B-containing NMDA receptors which is an important site of action of the non-selective agents.

The adverse effects exhibited upon administration of certain NMDA antagonists are not observed or are significantly reduced when using the forebrain selective NMDA antagonists of the instant invention. Thus, the present invention allows the utilization of the full therapeutic potential of levodopa by using NMDA antagonists synergistically in combination therewith.

SUMMARY OF THE INVENTION

The present invention is directed to a method of treating Parkinson's Disease in a mammal comprising administering to said mammal a Parkinson's Disease treating effective amount of a combination of a forebrain selective N-methyl-D-aspartate (NMDA) antagonist and an agent capable of increasing the excitatory feedback from the ventral lateral nucleus of the thalamus into the cortex (an excitatory feedback enhancing agent).

A preferred method within the scope of this invention is a method of treating Parkinson's Disease in a mammal suffering from Parkinson's Disease as described in the preceding paragraph wherein said agent capable of increasing the excitatory feedback from the ventral lateral nucleus of the thalamus into the cortex is selected from the group consisting of dopamine agonists, dopamine D1 agonists, dopamine D2 agonists, dopamine/β-adrenergic receptor agonists, dopamine/5-HT uptake inhibitor/5-HT-1A agonists, dopamine/opiate agonists, adrenoreceptor agonists, α2-adrenergic antagonist/dopamine agonists, α2-adrenergic/dopamine D2 agonists, dopamine uptake inhibitors, monoamine oxidase-B inhibitors, COMT inhibitors and levodopa.

A more preferred method within the scope of this invention is a method as described in the preceding paragraph wherein said forebrain selective NMDA antagonist is an NR2B subtype selective NMDA antagonist.

A still more preferred method within the scope of this invention is a method as described in the preceding paragraph wherein said excitatory feedback enhancing agent is levodopa.

A still more preferred method within the scope of this invention is a method as described in the preceding paragraph which further comprises treating said mammal with a levodopa decarboxylase inhibitor.

A still more preferred method within the scope of this invention is a method as described in the preceding paragraph wherein said NR2B subtype selective NMDA antagonist is a compound of the formula

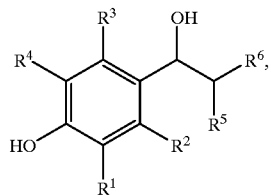

(I)

or a pharmaceutically acceptable acid addition salt thereof, wherein:
(a) $R^2$ and $R^5$ are taken separately and $R^1$, $R^2$, $R^3$ and $R^4$ are each independently hydrogen, $(C_1–C_6)$ alkyl, halo, $CF_3$, OH or $OR^7$ and $R^5$ is methyl or ethyl; or
(b) $R^2$ and $R^5$ are taken together and are

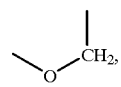

forming a chroman-4-ol ring, and $R^1$, $R^3$ and $R^4$ are each independently hydrogen, $(C_1–C_6)$ alkyl, halo, $CF_3$, OH or $OR^7$;
$R^6$ is

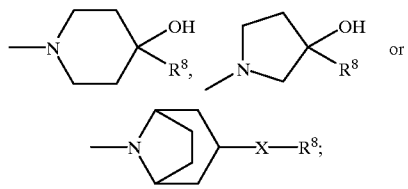

$R^7$ is methyl, ethyl, isopropyl or n-propyl;
$R^8$ is phenyl optionally substituted with up to three substituents independently selected from the group consisting of $(C_1–C_6)$ alkyl, halo and $CF_3$;
X is O, S or $(CH_2)_n$; and
n is 0, 1, 2, or 3.

Three compounds within the scope of this invention as described in the preceding paragraph are particularly preferred. These compounds are (+)-(1S,2S)-1-(4-hydroxyphenyl)-2-(4-hydroxy-4-phenylpiperidino)-1-propanol; (1S, 2S)-1-(4-hydroxy-3-methoxyphenyl)-2-(4-hydroxy-4-phenylpiperidino)-1-propanol; and (3R,4S)-3-(4-(4-flourophenyl)-4-hydroxypiperidin-1-yl)-chroman-4,7-diol.

A particularly preferred method within the scope of the preceding paragraph comprises administering the levodopa decarboxylase inhibitor carbidopa with one of the particularly preferred compounds.

Also within the scope of the present invention are pharmaceutical compositions comprising a Parkinson's Disease treating effective amount of a combination of a forebrain selective NMDA antagonist and an excitatory feedback enhancing agent; and a pharmaceutically acceptable diluent or carrier.

Particularly preferred compositions within the scope of this invention as described in the preceding paragraph are those compositions wherein:
(a) said forebrain selective NMDA antagonist is (+)-(1S, 2S)-1-(4-hydroxy-phenyl)-2-(4-hydroxy-4-phenylpiperidino)-1-propanol and said excitatory feedback enhancing agent is levodopa;

(b) said forebrain selective NMDA antagonist is (1S,2S)-1-(4-hydroxy-3-methoxyphenyl)-2-(4-hydroxy-4-phenylpiperidino)-1-propanol and said excitatory feedback enhancing agent is levodopa; and (c) said forebrain selective NMDA antagonist is (3R,4S)-3-(4-(4-fluorophenyl)-4-hydroxypiperidin-1-yl)-chroman-4,7-diol and said excitatory feedback enhancing agent is levodopa.

A more particularly preferred composition within the scope of this invention is a composition as described in the preceding paragraph further comprising carbidopa.

Also within the scope of the present invention is a first pharmaceutical composition for use with a second pharmaceutical composition for achieving an antiparkinson effect in a mammal suffering from Parkinson's Disease, which effect is greater than the sum of the antiparkinson effects achieved by administering said first and second pharmaceutical compositions separately and which second pharmaceutical composition comprises an amount of an excitatory feedback enhancing agent and a pharmaceutically acceptable carrier or diluent, said first pharmaceutical composition comprising an amount of a forebrain selective NMDA antagonist and a pharmaceutically acceptable carrier or diluent.

Particularly preferred compositions within the scope of this invention as described in the preceding paragraph are those compositions wherein:

(a) said forebrain selective NMDA antagonist is (+)-(1S,2S)-1-(4-hydroxy-phenyl)-2-(4-hydroxy-4-phenylpiperidino)-1-propanol;

(b) said forebrain selective NMDA antagonist is (1S,2S)-1-(4-hydroxy-3-methoxyphenyl)-2-(4-hydroxy-4-phenylpiperidino)-1-propanol; and (c) said forebrain selective NMDA antagonist is (3R,4S)-3-(4-(4-fluorophenyl)-4-hydroxypiperidin-1-yl)-chroman-4,7-diol.

Additionally within the scope of this invention is a first pharmaceutical composition for use with a second pharmaceutical composition for achieving an antiparkinson effect in a mammal suffering from Parkinson's Disease, which effect is greater than the sum of the antiparkinson effects achieved by administering said first and second pharmaceutical compositions separately and which second pharmaceutical composition comprises an amount of levodopa, an amount of a levodopa decarboxylase inhibitor and a pharmaceutically acceptable carrier or diluent, said first pharmaceutical composition comprising an amount of a forebrain selective NMDA antagonist and a pharmaceutically acceptable carrier or diluent.

Particularly preferred compositions within the scope of this invention as described in the preceding paragraph are those compositions wherein:

(a) said forebrain selective NMDA antagonist is (+)-(1S,2S)-1-(4-hydroxy-phenyl)-2-(4-hydroxy-4-phenylpiperidino)-1-propanol;

(b) said forebrain selective NMDA antagonist is (1S,2S)-1-(4-hydroxy-3-methoxyphenyl)-2-(4-hydroxy-4-phenylpiperidino)-1-propanol; and (c) said forebrain selective NMDA antagonist is (3R,4S)-3-(4-(4-fluorophenyl)-4-hydroxypiperidin-1-yl)-chroman-4,7-diol.

Also within the scope of the present invention is a first pharmaceutical composition for achieving an antiparkinson effect in a mammal suffering from Parkinson's Disease, which effect is greater than the sum of the antiparkinson effects achieved by administering said first and second pharmaceutical compositions separately and which second pharmaceutical composition comprises an amount of a forebrain selective NMDA antagonist and a pharmaceutically acceptable carrier or diluent, said first pharmaceutical composition comprising an amount of an excitatory feedback enhancing agent and a pharmaceutically acceptable carrier or diluent.

Particularly preferred compositions within the scope of this invention as described in the preceding paragraph are those compositions wherein said excitatory feedback enhancing agent is levodopa.

Also within the scope of the present invention is a first pharmaceutical composition for achieving an antiparkinson effect in a mammal suffering from Parkinson's Disease, which effect is greater than the sum of the antiparkinson effects achieved by administering said first and second pharmaceutical compositions separately and which second pharmaceutical composition comprises an amount of a forebrain selective NMDA antagonist and an amount of a levodopa decarboxylase inhibitor and a pharmaceutically acceptable carrier or diluent, said first pharmaceutical composition comprising an amount of levodopa.

Also within the scope of this invention is a first pharmaceutical composition for use with a second pharmaceutical composition and a third pharmaceutical composition for achieving an antiparkinson effect in a mammal suffering from Parkinson's Disease, which effect is greater than the sum of the antiparkinson effects achieved by administering said first and second pharmaceutical compositions separately and which second pharmaceutical composition comprises an amount of levodopa and a pharmaceutically acceptable carrier or diluent and said third pharmaceutical composition comprises a levodopa decarboxylase inhibitor and a pharmaceutically acceptable carrier or diluent, said first pharmaceutical composition comprising a forebrain selective NMDA antagonist and a pharmaceutically acceptable carrier or diluent.

Particularly preferred compositions within the scope of this invention as described in the preceding paragraph are those compositions wherein:

(a) said forebrain selective NMDA antagonist is (+)-(1S,2S)-1-(4-hydroxy-phenyl)-2-(4-hydroxy-phenylpiperidino)-1-propanol;

(b) said forebrain selective NMDA antagonist is (1S,2S)-1-(4-hydroxy-3-methoxyphenyl)-2-(4-hydroxy-4-phenylpiperidino)-1-propanol; and (c) said forebrain selective NMDA antagonist is (3R,4S)-3-(4-(4-fluorophenyl)-4-hydroxypiperidin-1-yl)-chroman-4,7-diol.

Additionally within the scope of this invention is a first pharmaceutical composition for use with a second pharmaceutical composition and a third pharmaceutical composition for achieving an antiparkinson effect in a mammal suffering from Parkinson's Disease, which effect is greater than the sum of the antiparkinson effects achieved by administering said first and second pharmaceutical compositions separately and which second pharmaceutical composition comprises an amount of a forebrain selective NMDA antagonist and a pharmaceutically acceptable carrier or diluent and said third composition comprises a levodopa decarboxylase inhibitor and a pharmaceutically acceptable carrier or diluent, said first pharmaceutical composition comprising an amount of levodopa and a pharmaceutically acceptable carrier or diluent.

Also within the scope of this invention is a method for achieving a synergistic antiparkinson effect in a mammal in need thereof which comprises administering to said mammal amounts of two therapeutic agents selected from the group consisting of: (a) a forebrain selective NMDA antagonist; and (b) an excitatory feedback enhancing agent, wherein the amount of (a) alone and the amount of (b) alone is insufficient to achieve the therapeutic effect; and wherein the combined effect of the amounts of the therapeutic agents administered is greater than the sum of the therapeutic effects of the amounts of the individual therapeutic agents separately administered.

A preferred method within the scope of this invention is the method as described in the preceding paragraph wherein an amount of a forebrain selective NMDA antagonist and an amount of an excitatory feedback enhancing agent are administered simultaneously.

An additionally preferred method within the scope of this invention is the method as described in the paragraph preceding the immediately preceding paragraph wherein an amount of a forebrain selective NMDA antagonist and an amount of an excitatory feedback enhancing agent are administered sequentially in any order.

Particularly preferred methods within the scope of this invention are the methods as described in the two paragraphs immediately preceding this paragraph wherein said methods further comprise administering an amount of carbidopa.

In a particularly preferred embodiment, this invention is directed to a method for achieving a synergistic antiparkinson effect in a mammal in need thereof which comprises administering to said mammal amounts of two therapeutic agents selected from the group consisting of: (a) a forebrain selective NMDA antagonist; and (b) an excitatory feedback enhancing agent, wherein the amount of (a) alone and the amount of (b) alone is insufficient to achieve the therapeutic effect; and wherein the combined effect of the amounts of the therapeutic agents administered is greater than the sum of the therapeutic effects of the amounts of the individual therapeutic agents separately administered; and wherein said forebrain selective NMDA antagonist is selected from the group consisting of (+)-(1S,2S)-1-(4-hydroxy-phenyl)-2-(4-hydroxy-4-phenylpiperidino)-1-propanol; (1S,2S)-1-(4-hydroxy-3-methoxyphenyl)-2-(4-hydroxy-4-phenylpiperidino)-1-propanol; and (3R,4S)-3-(4-(4-fluorophenyl)-4-hydroxypiperidin-1-yl)-chroman-4,7-diol.

The expression "pharmaceutically-acceptable acid addition salts" is intended to include but not be limited to such salts as the hydrochloride, hydrobromide, sulfate, hydrogen sulfate, phosphate, hydrogen phosphate, dihydrogenphosphate, acetate, succinate, citrate, tartrate, lactate, mandelate, methanesulfonate (mesylate) and p-toluenesulfonate (tosylate) salts.

The acid addition salts of the compounds of the present invention are readily prepared by reacting the base forms with the appropriate acid. When the salt is of a monobasic acid (e.g., the hydrochloride, the hydrobromide, the p-toluenesulfonate, the acetate), the hydrogen form of a dibasic acid (e.g., the hydrogen sulfate, the succinate) or the dihydrogen form of a tribasic acid (e.g., the dihydrogen phosphate, the citrate), at least one molar equivalent and usually a molar excess of the acid is employed. However when such salts as the sulfate, the hemisuccinate, the hydrogen phosphate or the phosphate are desired, the appropriate and exact chemical equivalents of acid will generally be used. The free base and the acid are usually combined in a co-solvent from which the desired salt precipitates, or can be otherwise isolated by concentration and/or addition of a non-solvent.

DETAILED DESCRIPTION OF THE INVENTION

The forebrain selective NMDA antagonists which are used in the synergistic combination of this invention are readily prepared.

The compounds of formula (I) of the instant invention wherein $R^2$ and $R^5$ are taken together forming a chroman-4-ol ring and $R^1$, $R^3$ and $R^4$ are hydrogen are prepared by methods analogous to those disclosed in U.S. Pat. No. 5,356,905, the teachings of which are incorporated herein by reference.

The compounds of formula (I) of the instant invention wherein $R^2$ and $R^5$ are taken separately and $R^1$, $R^2$, $R^3$ and $R^4$ are hydrogen are prepared by methods analogous to those disclosed in U.S. Pat. Nos. 5,185,343, 5,272,160 and 5,338,754, the teachings of which are incorporated herein by reference.

The compounds of formula (I) of the instant invention wherein $R^2$ and $R^5$ are taken together forming a chroman-4-ol ring and at least one of $R^1$, $R^3$ and $R^4$ is not hydrogen and the compounds of formula (I) of the instant invention wherein $R^2$ and $R^5$ are taken separately and at least one of $R^1$, $R^2$, $R^3$ and $R^4$ is not hydrogen are prepared as described hereinbelow.

Specifically, the compounds of formula (I) are most generally prepared by deprotecting a phenolic alcohol intermediate. This phenol protecting group is removed by conventional methods. The phenol group is preferably protected in the form of conventional silyl ethers such as triisopropyl, tert-butyldimethylsilyl, triphenylsilyl and the like or as benzyl or substituted benzyl ethers. The preferred method of removing said silyl groups employs 1 to 1.1 molar equivalents of tetrabutylammonium fluoride or another convenient fluoride source in a reaction inert solvent such as tetrahydrofuran. The reaction is conveniently carried out at about 0–50° C. and most conveniently at ambient temperature so as to avoid the cost of heating or cooling the reaction mixture and to minimize the decomposition of the product in the event of heating. One method of removing benzyl or substituted benzyl ethers employs conventional hydrogenolysis over a noble metal catalyst such as palladium or nickel in a reaction inert solvent, for example using 10% palladium on carbon as a catalyst, preferably at low pressures (e.g., 1–10 atmospheres) and temperatures (e.g., 20–75° C.) and generally in a reaction inert solvent such as methanol or ethanol. Another method for hydrogenolysis employs ammonium formate as the hydrogen source in a reaction inert solvent at low temperature (e.g. 20° C. to reflux). Suitable reaction inert solvents for this hydrogenolysis reaction include ethers such as diethylether, tetrahydrofuran or dioxane; lower alcohols such as methanol or ethanol; or a combination thereof. A particularly preferred solvent combination for this hydrogenolysis is a mixture of tetrahydrofuran and methanol.

As used in the preceding paragraph, and elsewhere herein, the expression "reaction inert solvent" refers to any solvent which does not interact with starting materials, reagents, intermediates or products in a manner which adversely affects the yield of the desired product.

Compounds of formula (I) wherein the phenolic hydroxy group is protected may be prepared by conventional hydride reduction of a 3-piperidino chromen-4-one, a 3-pyrrolidino-chromen-4-one, a 3-(8-aza-bicyclo(3.2.1)octanyl)-chromen-4-one, a 2-piperidino-4'-hydroxypropiophenone, a 2-pyrrolidino-4'-hydroxypropiophenone, a 2-(8-aza-bicyclo (3.2.1)octanyl)-4'-hydroxypropiohenone, a 3-piperidino chroman-4-one, a 3-pyrrolidino chroman-4-one, or a 2-8-aza-bicyclo(3.2.1)octanyl chromanone, e.g.,

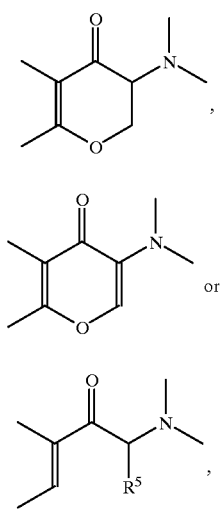

which in general produces a mixture of cis- and trans- isomers, e.g., respectively,

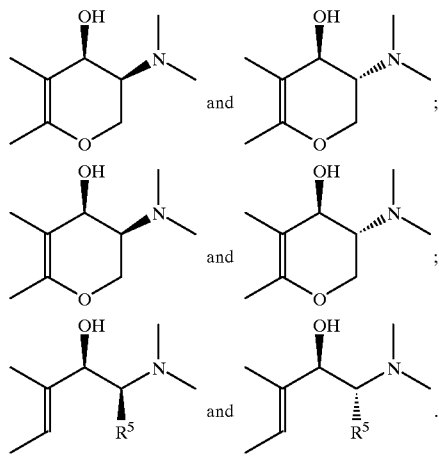

Of course, in individual cases, one or the other of these cis- or trans- isomers will frequently predominate.

These hydride reductions are carried out using conventional hydride reducing agents, e.g., NaBH$_4$ or LiAlH$_4$. The latter hydride reagent is usually used in excess (e.g., mol for mol) in a reaction inert solvent such as tetrahydrofuran, at reduced temperature (e.g., −15° C. to 75° C.). Any protecting groups which are still in place after ketone reduction are then removed according to the methods described hereinabove.

Intermediate compounds of the type (B) as depicted hereinabove, wherein R$^2$ and R$^5$ are taken together, and intermediate compounds of the type (D) as depicted hereinabove, wherein R$^2$ and R$^5$ are taken separately, are generally prepared by reaction of the corresponding mono-bromo chromanone derivative with a suitably substituted piperidine, pyrrolidine or 8-azabicyclo(3.2.1)octane, e.g.,

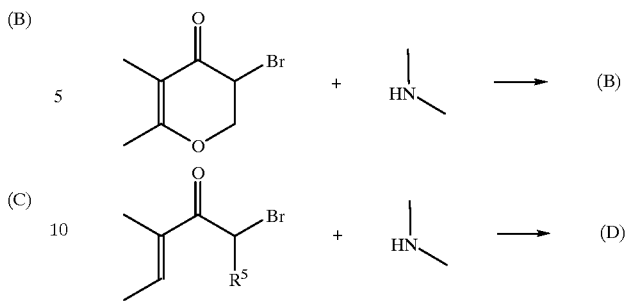

respectively. It will be recognized by those skilled in the art that for the purposes of this reaction the alpha-bromo group can be replaced by another nucleophilically displaceable group such as chloro, alkanesulfonyloxy or arylsulfonyloxy. This reaction is carried out under conditions typical of nucleophilic displacements in general. Where the two reactants are about equivalent in availability, close to substantially molar equivalents may be used; although when one of said reactants is more readily available, it is usually preferred to use said more readily available reactant in excess, to force the bimolecular nucleophilic displacement reaction to completion in a shorter period of time. Said reaction is generally carried out in the presence of at least 1 molar equivalent of a base, the amine derivative itself if it is readily available, but more usually a tertiary amine which is at least comparable in base strength to the nucleophilic amine; and in a reaction inert solvent such as acetonitrile, ethanol, methanol or the like. If desired, the reaction is catalyzed by the addition of up to one molar equivalent or more of an iodide salt (e.g., NaI, KI). Temperature is not critical, but will generally be somewhat elevated in order to force the reaction to completion within a shorter time period, but not so high as to lead to undue decomposition. A temperature in the range of 20–120° C. is generally satisfactory. It will be recognized by those skilled in the art that when elevated temperatures are used it is advantageous to monitor said reaction carefully so that the shortest possible reaction time is utilized to minimize decomposition. Conveniently, the temperature is the reflux temperature of the reaction mixture.

Intermediate compounds of the type (C) as depicted hereinabove, wherein R$^2$ and R$^5$ are taken together, are generally prepared by reaction of the corresponding alpha, alpha-dibromo chromanone derivative with a suitably substituted piperidine, pyrrolidine or 8-azabicyclo(3.2.1)octane, e.g.,

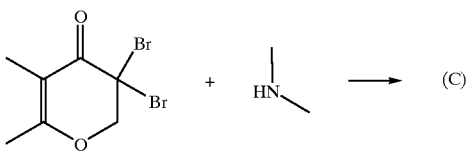

Except for the use of at least one additional molar equivalent of base (to neutralize the HBr formed in the concurrent dehydrohalogenation), conditions are analogous to those described above for the preparation of compounds of the types (B) and (D) by nucleophilic displacement.

The compounds of the formula (I) contain two asymmetric carbons—corresponding to two racemates and four optically active compounds. One of these racemates is the above-noted cis-isomer, and the other the trans-isomer. Each of these racemates is capable of resolution into a pair of enantiomers via diastereomeric acid addition salts with an optically active acid. Alternatively, the racemic alcohol is converted to corresponding diastereomeric esters or urethanes formed with an optically active acid or isocyanate. Such covalently bonded derivatives are subject to a variety of separation methods (e.g., chromatography). Such diastereomeric esters are formed from the alcohol and the optically active acid or isocyanate by standard methods, generally those involving activation of the acid, e.g., as the acid chloride, as a mixed anhydride with an alkyl chloroformate, or with a dehydrative coupling agent such as dicyclohexylcarbodiimide. Once the resulting diastereomeric esters are separated, e.g., by chromatographic methods, they are hydrolyzed by conventional methods, e.g., aqueous acid or aqueous base, to obtain the enantiomeric, optically active alcohol compounds of the formula (I). It is the intent of the applicant that this invention not be limited to the racemic cis- and trans- compounds specifically exemplified hereinbelow, but include all optically active enantiomers of the compounds of formula (I) of this invention.

The alpha-halo ketone starting materials required for the synthesis of the compounds of this invention are generally prepared by reaction of the corresponding acyl halide with an aromatic halide under the conditions of Friedel-Crafts acylation or under other aromatic acylation conditions well known to one of skill in the art. When the acyl halide does not contain a halo substituent alpha to the carbonyl group, the product of said aromatic acylation reaction is reacted under standard bromination conditions well known to one of skill in the art. Other starting materials and reagents required for the synthesis of the compounds of the present invention are readily available, either commercially, according to literature methods, or by methods exemplified in the Preparations section hereinbelow.

It is to be understood that other forebrain selective NMDA antagonists, and particularly NR2B subtype selective NMDA antagonists, are within the scope of the method of this invention. Included within the scope of these other NMDA antagonists are the compounds of formula (II), also termed ifenprodil, and the compound of formula (III), also termed eliprodil. Ifenprodil is prepared by methods analogous to those disclosed in U.S. Pat. No. 3,509,164, which is incorporated herein by reference. Eliprodil is prepared by methods analogous to those disclosed in U.S. Pat. No. 4,690,931, which is also incorporated herein by reference.

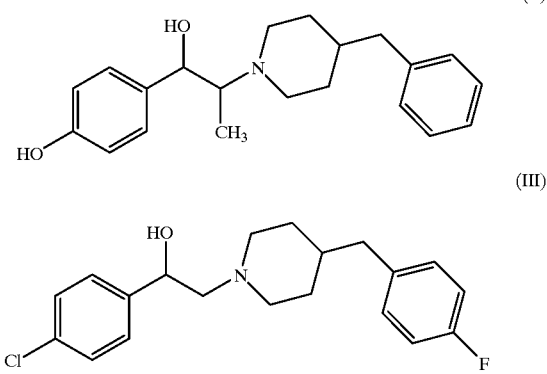

The present compounds of formula (I) are forebrain selective NMDA antagonists, as shown by the following biological assay. Frog oocytes are injected, using techniques well known to one of ordinary skill in the art, with RNA which expresses mammalian NR1 and NR2A, NR1 and NR2B, NR1 and NR2C or NR1 and NR2D subtype NMDA receptors. This ensures that a particular oocyte will only contain either an NR2A, NR2B, NR2C or NR2D subtype NMDA receptor. The frog oocytes thus prepared are treated with test compound according to the procedures set forth in Williams et al., Neuron, 10, 267–278 (1993). Compounds which show greater efficacy in the oocytes containing the NR2B receptors compared to other NMDA receptors are NR2B subtype selective NMDA antagonists and are thus forebrain selective NMDA antagonists.

The present compounds of formula (I) are shown to bind receptors in the forebrain region of the brain by performing the following autoradiography experiment. Male Sprague-Dawley rats are decapitated and the brains are removed quickly and frozen on powdered dry ice. The brains are mounted on a specimen stage with Tissue-Tek and 20 micron sections are thaw-mounted on chrome alum/gelatin subbed slides. These slides are stored at −20° C. until use. The slides must be used within 48 hours. On the day of the assay, the slides are warmed to room temperature and are incubated with a tritiated test compound (generally about 10 nM) for twenty minutes at 30° C. in 50 mM Tris Hcl buffer at pH 7.4. Non-specific binding is defined by the addition of 100 μM non-tritiated test compound. The slides are rinsed repeatedly in ice cold buffer for two to ten seconds and then blown dry with warm air. The slides are placed in cassettes and exposed to a tritium sensitive film for 14 to 18 days at 4. The film is developed, fixed and dried. Inspection of the slides reveals the portion of the brain in which the tritiated compound binds to a receptor site.

Many compounds and classes of compounds are reported to be useful in the treatment of Parkinson's Disease. Of these, the classes of compounds which operate to increase the excitatory feedback from the ventral lateral nucleus of the thalamus into the cortex (excitatory feedback enhancing agents) are within the scope of this invention. Classes of compounds which contain excitatory feedback enhancing agents include, but are not limited to, dopamine agonists, dopamine D1 agonists, dopamine D2 agonists, dopamine/β-adrenergic receptor agonists, dopamine/5-HT uptake-inhibitor/5-HT-1A agonists, dopamine/opiate agonists, adrenoreceptor agonists, α2-adrenergic antagonist/dopamine agonists, α2-adrenergic/dopamine D2 agonists, dopamine uptake inhibitors, monoamine oxidase-B inhibitors, COMT inhibitors and levodopa.

The dopamine agonists useful in the method of this invention include, but are not limited to, dihydroergocryptine, etisulergine, AF-14, alaptide, pergolide and piribedil. The dopamine D1 agonists useful in the method of this invention include, but are not limited to, A-68939, A-77636, dihydrexine and SKF-38393. The dopamine D2 agonists useful in the method of this invention include, but are not limited to, carbergoline, lisuride, N-0434, naxagolide, PD-118440, pramipexole, quinpirole and ropinirole. The dopamine/β-adrenergic receptor agonists useful in the method of this invention include, but are not limited to, DPDMS and dopexamine. A dopamine/5-HT uptake inhibitor/5-HT-1A agonist useful in the method of this invention includes, but is not limited to, roxindole. A dopamine/opiate agonist useful in the method of this invention includes, but is not limited to, NIH-10494. The adrenoreceptor agonists useful in the method of this invention include, but are not limited to, droxidopa, ibopamine and mazindole. A α2-adrenergic antagonist/dopamine agonist useful in the method of this invention includes, but is not limited to, terguride. The α2-adrenergic/dopamine D2 agonists useful in the method of this invention include, but are not limited to, ergolines and talipexole. The dopamine uptake inhibitors useful in the method of this invention include, but are not limited to, GBR-12909, GBR-13069, GYKI-52895 and NS-2141. The monoamine oxidase-B inhibitors useful in the method of this invention include, but are not limited to selegiline, N-(2-butyl)-N-methylpropargylamine, N-methyl-N-(2-pentyl) propargylamine, AGN-1133, ergot derivatives, Iazabemide, LU-53439, MD-280040 and mofegiline. The COMT inhibitors useful in the method of this invention include, but are not limited to, CGP-28014, entacapone and tolcapone. These compounds are well known in the literature and are readily prepared by methods disclosed therein.

The following excitatory feedback enhancing agents are particularly useful in the method of this invention: levodopa, prepared as disclosed in U.S. Pat No. 3,405,159; dihydroergocriptine, prepared as disclosed in U.S. Pat. No. 3,755,328; etisulergine and AF-14, each of which are prepared as disclosed in U.S. Pat. No. 4,348,392; alaptide, prepared as disclosed in U.S. Pat. No. 4,083,985; pergolide, prepared as disclosed in U.S. Pat. No. 4,166,182; piribedil, prepared as disclosed in U.S. Pat. No. 3,299,067; lisuride, prepared as disclosed in Coll. Czech. CC, 25, 1922 (1960); bromocriptine, prepared as disclosed in U.S. Pat. No. 3,752, 814; amantadine, prepared as disclosed in U.S. Pat. No. 3,152,180; 3-PPP, prepared as disclosed in European Patent No. 105,243; A-68930, prepared as disclosed in J. Med. Chem. 33, 2848 (1990); A-77636, prepared as disclosed in J. Org. Chem., 57, 7115 (1992); SKF-38393, prepared as disclosed in J. Med. Chem., 23, 973 (1980); N-0434, prepared as disclosed in U.S. Pat. No. 4,465,692; naxagolide, prepared as disclosed in U.S. Pat. No. 4,420,480; PD-118440, prepared as disclosed in U.S. Pat. No. 4,650, 805; pramipexole, prepared as disclosed in U.S. Pat. No. 4,886,812; quinpirole, prepared as disclosed in J. Med. Chem., 26, 1112 (1983); ropinirole, prepared as disclosed in U.S. Pat. No. 4,452,808; quinelorane, prepared as disclosed in U.S. Pat. No. 4,501,890; DPDMS, prepared as disclosed in Biochem. Pharm. 33, 2371, (1984); dopexamine, prepared as disclosed in U.S. Pat. No. 5,013,760; roxindole, prepared as disclosed in U.S. Pat. No. 4,251,538; NIH-10494, prepared as disclosed in J. Med. Chem., 30, 1906 (1987); droxidopa, prepared as disclosed in U.S. Pat. No. 3,920,728; ibopamine, prepared as disclosed in U.S. Pat. No. 4,218,470; mazindole, prepared as disclosed in U.S. Pat. No. 3,597,445; terguride, prepared as disclosed in U.S. Pat. No. 3,953,454; talipexole, prepared as disclosed in U.S. Pat. No. 3,804,849; GBR-12909, prepared as disclosed in U.S. Pat. No. 4,202, 896; GBR-13069, prepared as disclosed in Eu. J. Chem. Chim. Ther., 15, 363 (1980); GYKI-52895, prepared as disclosed in German patent DE 3,727,226; selegiline, prepared as disclosed in Netherlands patent NL 6605956; N-(Bu)-N-methylpropargylamine and N-methyl-N-(2-pent) propargylamine, each of which are prepared as disclosed in J. Med. Chem., 35, 3705 (1992); AGN-1133, prepared as disclosed in U.S. Pat. No. 3,201,470; lazabemide, prepared as disclosed in U.S. Pat. No. 4,764,522; MD-280040, prepared as disclosed in U.S. Pat. No. 4,971,995; mofegiline, prepared as disclosed in U.S. Pat. No. 4,454,158; CGP-28014, prepared as disclosed in U.S. Pat. No. 4,863,938; entacapone, prepared as disclosed in U.S. Pat. No. 5,135, 950; tolcapone, prepared as disclosed in Australia 90/603788; and SDZ HDC 912, prepared as disclosed in U.S. Pat. No. 4,950,672. The teaching of all U.S. patents which are referenced herein are incorporated herein by reference.

A forebrain selective NMDA antagonist as disclosed hereinabove, is used in combination with an excitatory feedback enhancing agent disclosed hereinabove to synergistically treat Parkinson's Disease. To determine the activity of the present combination of the forebrain selective NMDA antagonist and excitatory feedback enhancing agent, a forebrain selective NMDA antagonist is combined in suitable proportions with a excitatory feedback enhancing agent and the combination is tested according to the method well known to those skilled in the art as described in Greenamyre et al., Annals of Neurology, 35, 655–61 (1994).

Where used herein, a "synergistic amount" of a forebrain selective NMDA antagonist and a compound capable of restoring the balance of the excitatory feedback from the ventral lateral nucleus of the thalamus into the cortex (excitatory feedback enhancing agent) is an amount which, when administered to a mammal suffering from Parkinson's Disease, is sufficient to exhibit a greater action against said Parkinson's Disease than the sum of the action that would be observed upon independent administration of the forebrain selective NMDA antagonist and the excitatory feedback enhancing agent alone.

Due to the nature of Parkinson's Disease, the synergistic effects of the forebrain selective NMDA antagonist and the excitatory feedback enhancing agent will occur over a wide range of doses. Parkinson's Disease results from the progressive death of dopamine neurons projecting from the midbrain of the striatum. Since the clinical effect of this neuronal death is cumulative with advancing disease, administration of therapeutic agents must be titrated carefully over the course of the disease. Dose titration is accomplished readily by the clinician of ordinary skill in the art of treating mammals suffering from Parkinson's Disease enabled by this disclosure.

For administration of levodopa alone, an initial dose is typically 14 milligrams per kilogram of body weight of the patient per day. The dose is increased over the course of the disease to the maximally tolerated dose of approximately 114 milligrams per kilogram of body weight of the patient per day. For the co-administration of levodopa and carbidopa, an initial dose is typically 1.4 milligrams of levodopa per kilogram of body weight of patient per day. The dose is increased over the course of the disease to the maximally tolerated dose of 11.4 milligrams of levodopa per body weight of patient per day. Carbidopa is concomitantly administered at levels of at least 1.4 milligrams per kilogram of body weight of patient per day. For the treatment of Parkinson's Disease with (+)-(1S,2S)-1-(4-hydroxy-phenyl)-2-(4-hydroxy-4-phenylpiperidino)-1-propanol, and levodopa, (+)-(1S,2S)-1-(4-hydroxy-phenyl)-2-(4-hydroxy-4-phenylpiperidino)-1 -propanol is administered over the dose range of about 15 to 100 µg per kilogram of body weight of patient per day and levodopa is co-administered at an initial dose of 1.4 to 7.1 milligrams per kilogram of body weight of patient per day. When the synergistic combination includes at least 1.4 milligrams of carbidopa per kilogram of body weight of patient per day, the dose of levodopa is 0.14 milligrams to 0.71 milligrams per kilogram of body weight of patient per day. The dose of levodopa can be increased as required up to its maximum tolerated dose. However, the use of the forebrain selective NMDA antagonist in combination with levodopa should forestall the need to increase the dosage of levodopa in the latter stages of Parkinson's Disease.

Similarly, other excitatory feedback enhancing agents will also be dosed at ½ to ¹⁄₁₀ the dose at which the compound has a therapeutic effect alone or, after progression of Parkinson's Disease to its latter stages, at which the compound can be maximally tolerated. Such dose titration is readily accomplished by the clinician of ordinary skill in the art of treating Parkinson's patients enabled by this disclosure.

The synergistic combination of the present invention is generally administered in the form of a pharmaceutical composition comprising one of the forebrain selective NMDA antagonists and one of the excitatory feedback enhancing agents, together with a pharmaceutically acceptable carrier or diluent. Such compositions are generally formulated in a conventional manner utilizing solid or liquid vehicles or diluents as appropriate to the mode of administration. Alternatively, the forebrain selective NMDA antagonist and the excitatory feedback enhancing agent may be administered simultaneously in separate form to result in a synergistic combination of said forebrain selective NMDA antagonist and said excitatory feedback enhancing agent after incorporation into the body of the patient. In these conditions, the forebrain selective NMDA antagonist is formulated in one conventional pharmaceutical composition and the excitatory feedback enhancing agent is formulated in a separate conventional pharmaceutical composition. Optionally, when levodopa is the excitatory feedback enhancing agent, a levodopa decarboxylase inhibitor such as carbidopa is administered. Generally the levodopa decarboxylase inhibitor is administered as a separate pharmaceutical composition.

The individual elements of the combination of this invention, namely the forebrain selective NMDA antagonist or a pharmaceutical composition thereof and the excitatory feedback enhancing agent or a pharmaceutical composition thereof, may also be administered as individual compositions, which, when administered together, either simultaneously or sequentially, exhibit synergistic antiparkinson effects.

For purposes of oral administration, tablets containing excipients such as sodium citrate, calcium carbonate and dicalcium phosphate may be employed along with various disintegrants such as starch and preferably potato or tapioca starch, alginic acid and certain complex silicates, together with binding agents such as polyvinylpyrrolidone, sucrose, gelatin and acacia. Additionally, lubricating agents such as, but not limited to, magnesium stearate, sodium lauryl sulfate and talc are often very useful for tableting purposes. Solid compositions of a similar type may also be employed as fillers in soft elastic and hard-filled gelatin capsules; preferred materials in this connection also include, by way of example and not of limitation, lactose or milk sugar as well as high molecular weight polyethylene glycols. When aqueous suspensions and/or elixirs are desired for oral administration, the essential active ingredient may be combined with various sweetening or flavoring agents, coloring matter or dyes and, if so desired, emulsifying and/or suspending agents, together with diluents such as water, ethanol, propylene glycol, glycerin and various like combinations thereof.

The term antiparkinson, when used herein and in the appendant claims, defines an effect which alleviates the symptomatology of Parkinson's Disease.

The present invention is illustrated by the following examples, but is not limited to the details thereof.

All non-aqueous reactions were run under nitrogen for convenience and generally to maximize yields. All solvents/diluents were dried according to standard published procedures or purchased in a predried form. All reactions were stirred either magnetically or mechanically. NMR spectra are recorded at 300 MHz and are reported in ppm. The NMR solvent was $CDCl_3$ unless otherwise specified. IR spectra are reported in $cm^{-1}$, generally specifying only strong signals.

EXAMPLES

Example 1

(1R*,2R*)-1-(3-Fluoro-4-hydroxyphenyl)-2-(4-(4-fluorophenyl)-4-hydroxypiperidin-1-yl)-propan-1-ol mesylate A mixture of 3-fluoro-4-triisopropylsilyloxy-α-bromopropiophenone (the compound of Preparation 1, 1.19 g, 2.95 mmol), 4-(4-fluorophenyl)-4-hydroxypiperidine (0.864 g, 4.43 mmol) and triethylamine (1.03 mL, 7.38 mmol) in ethanol (25 mL) was refluxed 4 h then stirred at ambient temperature 64 h. The solvent was removed at reduced pressure and the residue was partitioned between ethyl acetate and water. The phases were separated and the organic layer was washed with brine, dried over calcium sulfate and concentrated. The residue was flash chromatographed on silica gel (1.5×3 inches) with elution proceeding as follows: 10% ethyl acetate/hexane (350 mL), nil; 20% ethyl acetate/hexane (150 mL), nil; 20% ethyl acetate/hexane (450 mL), 0.437 g (29%) of 1-(3-fluoro-4-triisopropylsilyloxyphenyl)-2-(4-(4-fluorophenyl)-4-hydroxypiperidin-1-yl)-propan-1-one as a yellow oil which had: NMR δ7.88 (dd, J=2, 11 Hz, 1 H), 7.81 (d, J=8.5 Hz, 1 H), 7.43 (dd, J=5.5, 9 Hz, 1 H), 7.00 (t, J=9 Hz, 1 H), 6.95 (t, J=8.5 Hz, 1 H), 4.05 (q, J=6.5 Hz, 1 H), 2.93–2.72 (m, 2 H), 2.72–2.53 (m, 2 H), 2.03 (sym m, 2 H), 1.82–1.58 (m, 3 H), 1.35–1.22 (m, 5 H), 1.10 (d, J=7 Hz, 18 H).

A mixture of sodium borohydride (0.027 g, 0.717 mmol) and ethanol (10 mL) was stirred 10 min and then 1-(3-fluoro-4-triisopropylsilyloxyphenyl)-2-(4-(4-fluorophenyl)-4-hydroxypiperidin-1-yl)-propan-1-one (0.371 g, 0.717 mmol in 10 mL of ethanol) was added. The reaction was stirred at ambient temperature overnight. The mixture was concentrated and the residue was partitioned between ethyl acetate and water. The phases were separated and the organic phase was washed with brine, dried over calcium sulfate and concentrated. The residue was flash chromatographed on silica gel (0.75×3 inches packed in hexane) with elution proceeding as follows: 10% ethyl acetate/hexane (200 mL), nil; 10% ethyl acetate/hexane (100 mL) and 20% ethyl acetate/hexane (200 mL), to give 0.22 g (59%) of (1R*, 2R*)-1-(3-fluoro-4-triisopropylsilyloxyphenyl)-2-(4-(4-fluorophenyl)-4-hydroxypiperidin-1-yl)-propan-1-ol. A sample recrystallized from ether had: mp 159–160° C.

The product of the above reaction (0.192 g, 0.37 mmol) was dissolved in tetrahydrofuran (10 mL) and tetrabutylammonium fluoride (0.407 mL, 0.407 mmol, 1 M tetrahydrofuran solution) was added. The reaction was stirred 30 min at ambient temperature and then concentrated. The residue was partitioned between ethyl acetate and water and the phases were separated. The organic layer was washed with brine, dried over calcium sulfate, and concentrated to afford 0.122 g, (91%) of white solid product. The solid was slurried in methanol (6 mL) and methanesulfonic acid (0.022 mL, 0.34 mmol) was added. The mixture was concentrated at the boil to 0.5 mL. Cooling gave white crystals which were collected by filtration to afford 0.062 g, (36%) of (1R*, 2R*)-1-(3-fluoro-4-hydroxyphenyl)-2-(4-(4-fluorophenyl)-4-hydroxypiperidin-1-yl)-propan-1-ol mesylate which had: mp 239–241° C. Analysis calculated for $C_{20}H_{23}F_2NO_3 \cdot CH_4SO_3$: C, 54.89; H, 5.92; N, 3.05. Found: C, 55.17; H, 6.08; N, 3.11.

Example 2

(1R*, 2R*)-1-(4-Hydroxy-3-methylphenyl)-2-(4-(4-fluorophenyl)-4-hydroxypiperidin-1-yl)-propan-1-ol mesylate A mixture of 3-methyl-4-triisopropylsilyloxy-α-bromopropiophenone (the compound of Preparation 6, 9.17 g, 22.97 mmol), 4-(4-fluorophenyl)-4-hydroxypiperidine (6.73 g, 34.45 mmol) and triethylamine (8.0 mL, 57.43 mmol) in ethanol (180 mL) was refluxed 6 h. The solvent was removed at reduced pressure and the residue was partitioned between ethyl acetate and water. The phases were separated and the organic layer was washed with brine, dried over calcium sulfate and concentrated. The residue was flash chromatographed on silica gel (3×3.5 inches packed in hexane) with elution proceeding as follows: 10% ethyl acetate/hexane (1000 mL), nil; 20% ethyl acetate/hexane (700 mL), nil; 20% ethyl acetate/hexane (1300 mL) and 25% ethyl acetate/hexane (600 mL), 7.66 g (65%) of 1-(3-methyl-4-triisopropylsilyloxyphenyl)-2-(4-(4-fluorophenyl)-4hydroxypiperidin-1-yl)-propan-1-one as a yellow foam which was suitable for use without further purification. A sample recrystallized from ethyl acetate/hexane as white crystals had: mp 78–82° C.

A mixture of sodium borohydride (0.564 g, 14.92 mmol) and ethanol (60 mL) was stirred 10 min and then 1-(3-methyl-4-triisopropylsilyloxyphenyl)-2-(4-(4-fluorophenyl)-4-hydroxypiperidin-1-yl)-propan-1-one (7.66 g, 14.92 mmol in 10 mL of ethanol) was added with two 30 mL ethanol rinses. The reaction was stirred at ambient temperature overnight. The white solid which precipitated was collected by filtration and dried to yield 5.72 g (74%) of (1R*, 2R*)-1-(3-methyl-4-triisopropylsilyloxyphenyl)-2-(4-(4-fluorophenyl)-4-hydroxypiperidin-1-yl)-propan-1-ol which was suitable for use without further purification and had: mp 188–189° C.

The product of the above reaction (5.72 g, 11.1 mmol) was dissolved in tetrahydrofuran (150 mL) and tetrabutylammonium fluoride (12.21 mL, 12.21 mmol, 1 M tetrahydrofuran solution) was added. The reaction was stirred 1 h at ambient temperature and then concentrated. The residue was partitioned between ethyl acetate and water and the phases were separated. The organic layer was concentrated and slurried with methylene chloride. The white solid which had precipitated was collected by filtration and dried to afford 3.41 g (85%) of (1R*, 2R*)-1-(4-hydroxy-3-methylphenyl)-2-(4-(4-fluorophenyl)-4-hydroxypiperidin-1-yl)-propan-1-ol. A sample (0.16 g, 0.447 mmol) was converted to its mesylate salt. It was slurried in methanol (8 mL) and methanesulfonic acid (0.029 mL, 0.45 mmol) was added. The mixture was filtered and concentrated; then the residue was recrystallized from ethanol to give 0.152 g (58%) of the mesylate salt which had: mp 215–216° C. Analysis calculated for $C_{21}H_{25}FNO_3 \cdot CH_4SO_3$: C, 58.01; H, 6.64; N, 3.07. Found: C, 57.99; H, 6.72; N, 3.17.

Example 3

(1R*, 2R*)-1-(3,5-Dimethyl-4-hydroxyphenyl)-2-(4-(4-chlorophenyl)-4-hydroxypiperidin-1-yl-propan-1-ol mesylate A mixture of 3,5-dimethyl-4-triisopropylsilyloxy-α-bromopropiophenone (the compound of Preparation 18, 1.50 g, 3.63 mmol), 4-(4-chlorophenyl)-4-hydroxypiperidine (1.00 g, 4.03 mmol) and triethylamine (1.7 mL, 12.2 mmol) in ethanol (30 mL) was refluxed 4.5 h and then stirred overnight at ambient temperature. The solvent was removed at reduced pressure and the residue was partitioned between ethyl acetate and water. The phases were separated and the organic layer was washed with brine, dried over magnesium sulfate and concentrated. The residue was flash chromatographed on silica gel (1×5 inches packed in hexane) with elution proceeding as follows: 10% ethyl acetate/hexane (750 mL), nil; 10% ethyl acetate/hexane (250 mL) and 20% ethyl acetate/hexane (500 mL), to give 0.82 g (41%) of 1-(3,5-dimethyl- 4-triisopropylsilyloxyphenyl)-2-(4-(4-chlorophenyl)-4-hydroxypiperidin-1-yl)-propan-1-one as a yellow foam which was suitable for use without further purification and had: NMR δ7.37 (s, 2 H), 7.36 (ABq, $\Delta v_{1-3}$=30.5 Hz, J=8.5 Hz, 4 H), 4.15 (q, J=6.7 Hz, 1 H), 2.85–2.75 (m, 2 H), 2.67–2.53 (m, 1 H), 2.31 (s, 6 H), 2.25–1.97 (m, 2 H), 1.74–1.60 (m, 2 H), 1.60 (s, 1 H), 1.40–1.18 (m, 6 H), 1.13 (d, J=7.2 Hz, 18 H).

A mixture of sodium borohydride (0.054 g, 1.43 mmol) and ethanol (5 mL) was stirred 10 min and then 1-(3,5-dimethyl-4-triisopropylsilyloxyphenyl)-2-(4-(4-chlorophenyl)-4-hydroxypiperidin-1-yl)-propan-1-one (0.77 g, 1.42 mmol in 25 mL of ethanol) was added. The reaction was stirred at ambient temperature overnight. The white solid which precipitated was collected by filtration and dried to yield 0.44 g (56%) of (1R*,2R*)-1-(3,5-dimethyl-4-triisopropylsilyloxyphenyl)-2-(4-(4-chlorophenyl)-4-hydroxypiperidin-1-yl)-propan-1-ol which was suitable for use without further purification and had: mp 211.5–212.5° C.

The product of the above reaction (0.40 g, 0.73 mmol) was dissolved in tetrahydrofuran (10 mL) and tetrabutylammonium fluoride (0.81 mL, 0.81 mmol, 1 M tetrahydrofuran solution) was added. The reaction was stirred 30 min at ambient temperature and then concentrated. The residue was partitioned between ethyl acetate and water and the phases were separated. The organic layer was washed with brine, dried and concentrated. The residue was flash chromatographed on silica gel (1×3 inches packed with hexane) with elution proceeding as follows: 50% ethyl acetate/hexane (300 mL), nil; 50% ethyl acetate/hexane (100 mL and ethyl acetate (200 mL), 0.247 g (88%) of (1R*,2R*)-1-(3,5-dimethyl-4-hydroxyphenyl)-2-(4-(4-chlorophenyl)-4-hydroxypiperidin-1-yl)-propan-1-ol. A sample (0.24 g, 0.616 mmol) was converted to its mesylate salt. It was slurried in methanol (15 mL) and methanesulfonic acid (0.040 mL, 0.616 mmol) was added. The mixture was filtered and concentrated; then the residue was recrystallized from 9:1 ethanol/water to give 0.228 g (58%) of the mesylate salt as a fluffy white solid which had: mp 202.5–203° C. Analysis calculated for $C_{22}H_{26}ClNO_3 \cdot CH_4SO_3$: C, 56.84; H, 6.64; N, 2.88. Found: C, 57.01; H, 6.83; N, 2.94.

Example 4

(1R*,2R*)-1-(3,5-Dimethyl-4-hydroxyphenyl)-2-(4-(4-fluorophenyl)-4-hydroxypiperidin-1-yl)-propan-1-ol mesylate A mixture of 3,5-dimethyl-4-triisopropylsilyloxy-α-bromopropiophenone (the compound of Preparation 18, 1.50 g, 3.63 mmol), 4-(4-fluorophenyl)-4-hydroxypiperidine (0.78 g, 4.00 mmol) and triethylamine (1.0 mL, 7.2 mmol) in ethanol (30 mL) was refluxed 4.5 h and then stirred overnight at ambient temperature. The solvent was removed at reduced pressure and the residue was partitioned between ethyl acetate and water. The phases were separated and the organic layer was washed with brine, dried over magnesium sulfate and concentrated. The residue was flash chromatographed on silica gel (1×4 inches packed in hexane) with elution proceeding as follows: 10% ethyl acetate/hexane (500 mL), nil; 20% ethyl acetate/hexane (500 mL), 0.96 g (50%) of 1-(3,5-dimethyl-4-triisopropylsilyloxyphenyl)-2-(4-(4-fluorophenyl)-4-hydroxypiperidin-1-yl)-propan-1-one as an orange foam which was suitable for use without further purification and had: NMR δ7.74 (s, 2 H), 7.48–7.43 (m, 2 H), 7.02 (t, J=8.8 Hz, 2 H), 4.15 (q, J=6.7 Hz, 1 H), 2.90–2.77 (m, 3 H), 2.68–2.57 (m, 1 H), 2.31 (s, 6 H), 2.28–2.03 (m, 2 H), 1.77–1.66 (m, 2 H), 1.56 (s, 1 H), 1.41–1.19 (m, 5 H), 1.13 (d, J=7.2 Hz, 18 H).

A mixture of sodium borohydride (0.065 g, 1.72 mmol) and ethanol (5 mL) was stirred 10 min and then 1-(3,5-dimethyl-4-triisopropylsilyloxyphenyl)-2-(4-(4-fluorophenyl)-4-hydroxypiperidin-1-yl)-propan-1-one (0.90 g, 1.71 mmol in 25 mL of ethanol) was added. The reaction was stirred at ambient temperature over the weekend. The white solid which precipitated was collected by filtration and dried to yield 0.365 g (40%) of (1R*,2R*)-1-(3,5-dimethyl-4-triisopropylsilyloxyphenyl)-2-(4-(4-fluorophenyl)-4-hydroxypiperidin-1-yl)-propan-1-ol which was suitable for use without further purification and had: mp 186.5–187° C. Analysis calculated for $C_{31}H_{48}FNO_3Si.0.125\ H_2O$: C, 69.69; H, 9.15; N, 2.62. Found: C, 69.65; H, 9.29; N, 2.57.

The product of the above reaction (0.31 g, 0.59 mmol) was dissolved in tetrahydrofuran (10 mL) and tetrabutylammonium fluoride (0.65 mL, 0.65 mmol, 1 M tetrahydrofuran solution) was added. The reaction was stirred 30 min at ambient temperature and then concentrated. The residue was partitioned between ethyl acetate and water and the phases were separated. The organic layer was washed with brine, dried and concentrated. The residue was flash chromatographed on silica gel (1×3 inches packed with hexane) with elution proceeding as follows: 50% ethyl acetate/hexane (150 mL), nil; 50% ethyl acetate/hexane (50 mL) and ethyl acetate (200 mL), 0.200 g(91%) of (1R*,2R*)-1-(3,5-dimethyl-4-hydroxyphenyl)-2-(4-(4-fluorophenyl)-4-hydroxypiperidin-1-yl)-propan-1-ol. A sample (0.194 g, 0.5.19 mmol) was converted to its mesylate salt. It was slurried in methanol (15 mL) and methanesulfonic acid (0.034 mL, 0.524 mmol) was added. The mixture was filtered and concentrated; then the residue was recrystallized from 9:1 ethanol/water to give the mesylate salt as a fluffy white solid (0.174 g) which had: mp 179–180° C. Analysis calculated for $C_{22}H_{28}FNO3.CH_4SO_3.0.25\ H_2O$: C, 58.27; H, 6.91; N, 2.95. Found: C, 58.30; H, 7.24; N, 3.00.

Example 5

(1R*,2R*)-1-(3,5-Difluoro-4-hydroxyphenyl)-2-(4-(4-chlorophenyl)-4-hydroxypiperidin-1-yl-propan-1-ol mesylate A mixture of 3,5-difluoro-4-triisopropylsilyloxy-α-bromopropiophenone (the compound of Preparation 20, 1.50 g, 3.56 mmol), 4-(4-chlorophenyl)-4-hydroxypiperidine (1.00 g, 4.03 mmol) and triethylamine (1.7 mL, 12.2 mmol) in ethanol (30 mL) was refluxed 4.5 h and then stirred overnight at ambient temperature. The solvent was removed at reduced pressure and the residue was partitioned between ethyl acetate and water. The phases were separated and the organic layer was washed with brine, dried over magnesium sulfate and concentrated. The residue was flash chromatographed on silica gel (1×4 inches packed in hexane) with elution proceeding as follows: 10% ethyl acetate/hexane (250 mL), nil; 10% ethyl acetate/hexane (250 mL) and 20% ethyl acetate/hexane (250 mL), 0.79 g (40%) of 1-(3,5-difluoro-4-triisopropylsilyloxyphenyl)-2-(4-(4-chlorophenyl)-4-hydroxypiperidin-1-yl)-propan-1-one as an orange foam which was suitable for use without further purification and had: NMR δ7.73 (long range coupled d, J=9.0 Hz, 2 H), 7.37 (ABq, Δv₁₋₃=26.3 Hz, J=8.7 Hz, 4 H), 4.03 (q, J=6.8 Hz, 1 H), 2.95–2.81 (m, 2 H), 2.66–2.61 (m, 2 H), 2.17–1.93 (m, 2 H), 1.80–1.55 (m, 3 H), 1.39–1.21 (m, 5 H), 1.12 (d, J=7.2 Hz, 18 H).

A mixture of sodium borohydride (0.058 g, 1.40 mmol) and ethanol (5 mL) was stirred 10 min and then 1-(3,5-difluoro-4-triisopropylsilyloxyphenyl)-2-(4-(-4-chlorophenyl)-4-hydroxypiperidin-1-yl)-propan-1-one (0.76 g, 1.38 mmol in 20 mL of ethanol) was added. The reaction was stirred at ambient temperature over the weekend. The white solid which precipitated was collected by filtration and dried to yield 0.43 g (57%) of (1R*,2R*)-1-(3,5-difluoro-4-triisopropylsilyloxyphenyl)-2-(4-(4-chlorophenyl)-4-hydroxypiperidin-1-yl)-propan-1-ol which was suitable for use without further purification and had: mp 192–192.5° C. Analysis calculated for $C_{29}H_{42}ClF_2NO_3Si.0.25\ H_2O$: C, 62.35; H, 7.67; N, 2.51. Found: C, 62.37; H, 7.81; N, 2.73.

The product of the above reaction (0.39 g, 0.70 mmol) was dissolved in tetrahydrofuran (10 mL) and tetrabutylammonium fluoride (0.80 mL, 0.80 mmol, 1 M tetrahydrofuran solution) was added. The reaction was stirred 30 min at ambient temperature and then concentrated. The residue was partitioned between ethyl acetate and water and the phases were separated. The organic layer was washed with brine, dried and concentrated. The residue was flash chromatographed on silica gel (1×4 inches) with elution proceeding as follows: 50% ethyl acetate/hexane (200 mL), nil; ethyl acetate (200 mL), nil; 2% methanol/ethyl acetate (200 mL) and 5% methanol/ethyl acetate (200 mL), to give 0.232 g (86%) of (1R*,2R*)-1-(3,5-difluoro-4-hydroxyphenyl)-2-(4-(4-chlorophenyl)-4-hydroxypiperidin-1-yl)-propan-1-ol. A sample (0.226 g, 0.589 mmol) was converted to its mesylate salt. It was slurried in methanol (15 mL) and methanesulfonic acid (0.038 mL, 0.587 mmol) was added. The mixture was filtered and concentrated; then the residue was recrystallized from 9:1 ethanol/water to give the mesylate salt as a white solid (0.240 g) which had: mp 239.5–240° C. Analysis calculated for $C_{20}H_{22}ClF_2NO_3.CH_4SO_3.H_2O$: C, 50.65; H, 5.67; N, 2.81. Found: C, 50.94; H, 5.54; N, 2.85.

Example 6

(1R*,2R*)-1-(3,5-Dimethyl-4-hydroxyphenyl)-2-(4-(4-trifluoromethylphenyl)-4-hydroxypiperidin-1-yl)-propan-1-ol mesylate A mixture of 3,5-dimethyl-4-triisopropylsilyloxy-α-bromopropiophenone (the compound of Preparation 18, 2.00 g, 4.84 mmol), 4-(4-trifluoromethylphenyl)-4-hydroxypiperidine (1.78 g, 7.26 mmol) and triethylamine (1.4 mL, 10.0 mmol) in ethanol (30 mL) was refluxed 7.75 h and then stirred overnight at ambient temperature. The solvent was removed at reduced pressure and the residue was partitioned between ethyl acetate and water. The phases were separated and the organic layer was washed with brine, dried over magnesium sulfate and concentrated. The residue was flash chromatographed on silica gel (1.5×4 inches packed in hexane) with elution proceeding as follows: 10% ethyl acetate/hexane (500 mL), nil; 25% ethyl acetate/hexane (250 mL), 1.39 g (50%) of 1-(3,5-dimethyl-4-triisopropylsilyloxyphenyl)-2-(4-(4-trifluoromethylphenyl)-4-hydroxypiperidin-1-yl)-propan-1-one as an orange foam which was suitable for use without further purification and had: NMR δ7.74 (s, 2 H), 7.60 (m, 4 H), 4.17 (q, J=6.8 Hz, 1 H), 2.92–2.79 (m, 2 H), 2.71–2.58 (m, 1 H), 2.31 (s, 6 H), 2.25–2.00 (m, 2 H), 1.76–1.65 (m, 2 H), 1.41–1.18 (m, 6 H), 1.13 (d, J=7.2 Hz, 18 H).

A mixture of sodium borohydride (0.090 g, 2.38 mmol) and ethanol (5 mL) was stirred 10 min and then 1-(3,5-dimethyl-4-triisopropylsilyloxyphenyl)-2-(4-(4-trifluoromethylphenyl)-4-hydroxypiperidin-1-yl)-propan-1-one (1.30 g, 2.25 mmol in 25 mL of ethanol) was added. The reaction was stirred at ambient temperature overnight. The white solid which precipitated was collected by filtration and dried to yield 0.408 g (31%) of (1R*,2R*)-1-(3,5-dimethyl-4-triisopropylsilyloxyphenyl)-2-(4-(4-trifluoromethylphenyl)-4-hydroxypiperidin-1-yl)-propan-1-ol which was suitable for use without further purification and had: mp 177–177.5° C. Analysis calculated for $C_{32}H_{48}F_3NO_3Si \cdot 0.25\ H_2O$: C, 65.78; H, 8.37; N, 2.40. Found: C, 65.65; H, 8.51; N, 2.57.

The product of the above reaction (0.348 g, 0.60 mmol) was dissolved in tetrahydrofuran (10 mL) and tetrabutylammonium fluoride (0.60 mL, 0.60 mmol, 1 M tetrahydrofuran solution) was added. The reaction was stirred overnight at ambient temperature. The reaction was diluted with water and ether and stirred vigorously. The solid which precipitated was filtered and rinsed with ether and weighed 0.166 g (65% of product). The filtrate was extracted with ethyl acetate. The organic layer was washed with brine, dried and concentrated. The residue was flash chromatographed on silica gel (1×3 inches) with elution proceeding as follows: 50% ethyl acetate/hexane (100 mL), nil; 50% ethyl acetate/hexane (100 mL) and ethyl acetate (75 mL), 0.077 g of product. In this manner 0.243 g (96%) of (1R*,2R*)-1-(3,5-dimethyl-4-hydroxyphenyl)-2-(4-(4-trifluoromethylphenyl)-4-hydroxypiperidin-1-yl)-propan-1-ol was obtained. The product was converted to its mesylate salt. It was slurried in 9:1 ethanol/water (5 mL) and methanesulfonic acid (0.038 mL, 0.587 mmol) was added. The mixture was filtered and concentrated to about 0.5 mL and the product was collected to give 0.184 g of the mesylate salt as a white solid which had: mp 147–148° C. Analysis calculated for $C_{23}H_{28}F_3NO_3 \cdot CH_4SO_3 \cdot 1.25\ H_2O$: C, 53.18; H, 6.42; N, 2.58. Found: C, 53.18; H, 6.63; N, 2.58.

Example 7

(1R*,2R*)-1-(3,5-Dichloro-4-hydroxyphenyl)-2-(4-(4fluorophenyl)-4-hydroxypiperidin-1-yl)-propan-1-ol mesylate A mixture of 3,5-dichloro-4-triisopropylsilyloxy-α-bromopropiophenone (the compound of Preparation 14, 1.00 g, 2.20 mmol), 4-(4-fluorophenyl)-4-hydroxypiperidine (0.64 g, 3.28 mmol) and triethylamine (0.62 mL, 4.45 mmol) in ethanol (20 mL) was refluxed 6 h and then stirred overnight at ambient temperature. The solvent was removed at reduced pressure and the residue was partitioned between ethyl acetate and water. The phases were separated and the organic layer was washed with brine, dried over magnesium sulfate and concentrated. The residue was flash chromatographed on silica gel (1×4 inches packed in hexane) with elution proceeding as follows: 10% ethyl acetate/hexane (250 mL), nil; 10% ethyl acetate/hexane (350 mL) 0.12 g (10%) of 1-(3,5-dichloro-4-triisopropylsilyloxyphenyl)-2-(4-(4-fluorophenyl)-4-hydroxypiperidin-1-yl)-propan-1-one as an orange oil which was carried directly into the next step.

A mixture of sodium borohydride (0.010 g, 0.26 mmol) and ethanol (1 mL) was stirred 10 min and then 1-(3,5-dichloro-4-triisopropylsilyloxyphenyl)-2-(4-(4-fluorophenyl)-4-hydroxypiperidin-1-yl)-propan-1-one (0.12 g, 0.211 mmol in 4 mL of ethanol) was added. The reaction was stirred at ambient temperature overnight. The mixture was quenched with water and concentrated at 40° C. The residue was partitioned between ethyl acetate and water and the phases were separated. The organic layer was washed with brine, dried over magnesium sulfate, and concentrated. The residue was flash chromatographed on silica gel (0.75×4 inches packed in hexane) with elution proceeding as follows: 10% ethyl acetate/hexane (200 mL), nil; 20% ethyl acetate/hexane (150 mL), 0.033 g (27%) of (1R*,2R*)-1-(3,5-dichloro-4-triisopropylsilyloxyphenyl)-2-(4-(4-fluorophenyl)-4-hydroxypiperidin-1-yl)-propan-1-ol as a yellow oil which was suitable for use without further purification.

The product of the above reaction (0.033 g, 0.058 mmol) was dissolved in tetrahydrofuran (5 mL) and tetrabutylammonium fluoride (0.060 mL, 0.060 mmol, 1 M tetrahydrofuran solution) was added. The reaction was stirred 3 h at ambient temperature and then concentrated. The residue was partitioned between ethyl acetate and water and the phases were separated. The organic layer was washed with brine, dried and concentrated. The residue was flash chromatographed on silica gel (0.75×3 inches packed with hexane) with elution proceeding as follows: 25% ethyl acetate/hexane (200 mL), nil; 50% ethyl acetate/hexane (150 mL), to give 0.014 g (58%) of (1R*,2R*)-1-(3,5-dichloro-4-hydroxyphenyl)-2-(4-(4-fluorophenyl)-4hydroxypiperidin-1-yl)-propan-1-ol as a white solid. The sample was converted to its mesylate salt. It was slurried in methanol and methanesulfonic acid (0.0022 mL, 0.0034 mmol) was added. The mixture was concentrated; then the residue was triturated with 20:1 ether/ethanol to give 0.013 g of the mesylate salt as a white solid which had: NMR ($D_2O/DMSO-d_6$) δ7.70 (ABq, $\Delta v_{1-3}$=23.8 Hz, J=8.5 Hz, 4 H), 7.42 (s, 2 H), 4.70 (d, J=10.2 Hz, 1 H), 3.71–3.50 (m, 4 H), 3.37–3.32 (m, 1 H), 2.75 (s, 3 H), 2.60–2.42 (m, 2 H), 2.15–2.05 (m, 2 H), 1.11 (d, J=6.8 Hz, 3 H).

Example 8

(1R*,2R*)-1-(3,5-Dichloro-4-hydroxyphenyl)-2-(4-(4-trifluoromethylphenyl)-4-hydroxypiperidin-1-yl)-propan-1-ol mesylate A mixture of 3,5-dichloro-4-triisopropylsilyloxy-α-bromopropiophenone (the compound of Preparation 14, 1.00 g, 2.20 mmol), 4-(4-trifluoromethylphenyl)-4-hydroxypiperidine (0.80 g, 3.26 mmol) and triethylamine (0.62 mL, 4.45 mmol) in ethanol (20 mL) was refluxed 6 h and then stirred overnight at ambient temperature. The solvent was removed at reduced pressure and the residue was partitioned between ethyl acetate and water. The phases were separated and the organic layer was washed with brine, dried over magnesium sulfate and concentrated. The residue was flash chromatographed on silica gel (1×3 inches packed in hexane) with elution proceeding as follows: 10% ethyl acetate/hexane (250 mL), nil; 10% ethyl acetate/hexane (250 mL) 0.18 g (13%) of 1-(3,5-dichloro-4-triisopropylsilyloxyphenyl)-2-(4-(4-trifluoromethylphenyl)-4-hydroxypiperidin-1-yl)-propan-1-one as an orange oil which was carried directly into the next step.

A mixture of sodium borohydride (0.012 g, 0.317 mmol) and ethanol (1 mL) was stirred 10 min and then 1-(3,5-dichloro-4-triisopropylsilyloxyphenyl)-2-(4-(4-trifluoromethylphenyl)-4-hydroxypiperidin-1-yl)-propan-1-one (0.18 g, 0.291 mmol in 4 mL of ethanol) was added. The reaction was stirred at ambient temperature overnight. The mixture was quenched with water and concentrated at 40° C. The residue was partitioned between ethyl acetate and water and the phases were separated. The organic layer was washed with brine, dried over magnesium sulfate, and concentrated. The residue was flash chromatographed on silica gel (0.75×4 inches packed in hexane) with elution proceeding as follows: 10% ethyl acetate/hexane (200 mL), nil; 20% ethyl acetate/hexane (150 mL), 0.072 g (40%) of (1R*,2R*)-1-(3,5-dichloro-4-triisopropylsilyloxyphenyl)-2-(4-(4-trifluoromethylphenyl)-4-hydroxypiperidin-1-yl)-propan-1-ol as a yellow oil which was suitable for use without further purification.

The product of the above reaction (0.072 g, 0.116 mmol) was dissolved in tetrahydrofuran (5 mL) and tetrabutylammonium fluoride (0.120 mL, 0.120 mmol, 1 M tetrahydrofuran solution) was added. The reaction was stirred 3 h at ambient temperature and then concentrated. The residue was flash chromatographed on silica gel (0.75×4 inches packed with hexane) with elution proceeding as follows: 25% ethyl acetate/hexane (200 mL), nil; 50% ethyl acetate/hexane (100 mL), 0.028 g (52%) of (1R*,2R*)-1-(3,5-dichloro-4-hydroxyphenyl)-2-(4-(4-trifluoromethylphenyl)-4-hydroxypiperidin-1-yl)-propan-1-ol as a white solid. The sample was converted to its mesylate salt. It was slurried in methanol and methanesulfonic acid (0.0039 mL, 0.006 mmol) was added. The mixture was concentrated; then the residue was triturated with 20:1 ether/ethanol to give 0.022 g of the mesylate salt as a white solid which had: mp 208–208.5° C.; NMR (D$_2$O/DMSO-d$_6$) δ7.49–7.42 (m, 6 H), 4.70 (d, J=10.2 Hz, 1 H), 3.72–3.47 (m, 4 H), 3.36–3.28 (m, 1 H), 2.75 (s, 3 H), 2.55–2.33 (m, 2 H), 2.14–2.02 (m, 2 H), 1.10 (d, J=6.8 Hz, 3 H).

Example 9

(1R*,2R*)-1-(3,5-Dichloro-4-hydroxyphenyl)-2-(4-(4-chlorophenyl)-4-hydroxypiperidin-1-yl)-propan-1-ol mesylate A mixture of 3,5-dichloro-4-triisopropylsilyloxy-α-bromopropiophenone (the compound of Preparation 14, 1.00 g, 2.20 mmol), 4-(4-chlorophenyl)-4-hydroxypiperidine (0.81 g, 3.26 mmol) and triethylamine (0.93 mL, 6.67 mmol) in ethanol (20 mL) was refluxed 6 h and then stirred overnight at ambient temperature. The solvent was removed at reduced pressure and the residue was partitioned between ethyl acetate and water. The phases were separated and the organic layer was washed with brine, dried over magnesium sulfate and concentrated. The residue was flash chromatographed on silica gel (1×3 inches packed in hexane) with elution proceeding as follows: 10% ethyl acetate/hexane (250 mL), nil; 10% ethyl acetate/hexane (250 mL) 0.08 g (6%) of 1-(3,5-dichloro-4-triisopropylsilyloxyphenyl)-2-(4-(4-chlorophenyl)-4-hydroxypiperidin-1-yl)-propan-1-one as an orange oil which was carried directly into the next step.

A mixture of sodium borohydride (0.010 g, 0.26 mmol) and ethanol (1 mL) was stirred 10 min and then 1-(3,5-dichloro-4-triisopropylsilyloxyphenyl)-2-(4-(4-chlorophenyl)-4-hydroxypiperidin-1-yl)-propan-1-one (0.08 g, 0.137 mmol in 4 mL of ethanol) was added. The reaction was stirred at ambient temperature overnight. The mixture was quenched with water and concentrated at 40° C. The residue was partitioned between ethyl acetate and water and the phases were separated. The organic layer was washed with brine, dried over magnesium sulfate, and concentrated. The residue was flash chromatographed on silica gel (0.75×4 inches packed in hexane) with elution proceeding as follows: 10% ethyl acetate/hexane (200 mL), nil; 20% ethyl acetate/hexane (150 mL), 0.03 g (40%) of (1R*,2R*)-1-(3,5-dichloro-4-triisopropylsilyloxyphenyl)-2-(4-(4-chlorophenyl)-4-hydroxypiperidin-1-yl)-propan-1-ol as a yellow oil which was suitable for use without further purification.

The product of the above reaction (0.030 g, 0.051 mmol) was dissolved in tetrahydrofuran (5 mL) and tetrabutylammonium fluoride (0.053 mL, 0.053 mmol, 1 M tetrahydrofuran solution) was added. The reaction was stirred 3 h at ambient temperature and then concentrated. The residue was flash chromatographed on silica gel (0.75×3 inches packed with hexane) with elution proceeding as follows: 25% ethyl acetate/hexane (200 mL), nil; 50% ethyl acetate/hexane (150 mL), 0.009 g (41%) of (1R*,2R*)-1-(3,5-dichloro-4-hydroxyphenyl)-2-(4-(4-chlorophenyl)-4-hydroxypiperidin-1-yl)-propan-1-ol as a white solid. The sample was converted to its mesylate salt. It was slurried in methanol and methanesulfonic acid (0.0014 mL, 0.002 mmol) was added. The mixture was concentrated; then the residue was triturated with 10:1 ether/ethanol to give 0.0085 g of the mesylate salt as a white solid which had: mp 223–223.5° C.; NMR (D$_2$O) δ7.54–7.46 (m, 6 H), 4.70 (d, 1 H partially obscured by the solvent), 3.74–3.53 (m, 4 H), 3.37 (br d, J=13.2 Hz, 1 H), 2.80 (s, 3 H), 2.60–2.27 (m, 2 H), 2.20–2.07 (m, 2 H), 1.15 (d, J=6.8 Hz, 3 H).

Example 10

(1R*,2R*)-1-(3,5-Difluoro-4-hydroxyphenyl)-2-(4-(4-fluorophenyl)-4-hydroxypiperidin-1-yl)-propan-1-ol mesylate A mixture of 4-benzyloxy-3,5-difluoro-α-bromopropiophenone (the compound of Preparation 22, 1.00 g, 2.82 mmol) and 4-(4-fluorophenyl)-4-hydroxypiperidine (1.1 g, 5.63 mmol) in ethanol (25 mL) was refluxed overnight. The solvent was removed at reduced pressure and the residue was partitioned between ethyl acetate and water. The phases were separated and the organic layer was washed with brine, dried over magnesium sulfate and concentrated. The residue was flash chromatographed on silica gel (1×4 inches packed in hexane) with elution proceeding as follows: 5% ethyl acetate/hexane (500 mL), nil; 15% ethyl acetate/hexane (500 mL), nil; 20% ethyl acetate/hexane (250 mL), 0.59 g (45%) of 1-(4-benzyloxy-3,5-difluorophenyl)-2-(4-(4-fluorophenyl)-4-hydroxypiperidin-1-yl)-propan-1-one as a bright yellow oil which was suitable for use without further purification and had: NMR δ7.75 (long range coupled d, J=9.2 Hz, 2 H), 7.48–7.30 (m, 7 H), 7.03 (long range coupled t, J=8.7 Hz, 2 H), 5.31 (s, 2 H), 4.01 (q, J=6.7 Hz, 1 H), 2.93 (dt, J=2.6, 11.2 Hz, 1 H), 2.80–2.75 (m, 1 H), 2.70–2.60 (m, 2 H), 2.18–1.92 (m, 2 H), 1.81–1.62 (m, 2 H), 1.30 (d, J=6.7 Hz, 3 H).

A mixture of sodium borohydride (0.050 g, 1.32 mmol) and ethanol (5 mL) was stirred 10 min and then 1-(4-benzyloxy-3,5-difluorophenyl)-2-(4-(4-fluorophenyl)-4-hydroxypiperidin-1-yl)-propan-1-one (0.55 g, 1.17 mmol in 20 mL of ethanol) was added. The reaction was stirred at ambient temperature overnight. The white solid which precipitated was collected by filtration and dried to yield 0.34 g of product. The filtrate was concentrated at reduced pressure and 400° C. The residue was partitioned between ethyl acetate and water. The phases were separated and the organic layer was washed with water and brine, dried over magnesium sulfate and concentrated. The residue was flash chromatographed on silica gel (1×4 inches packed with hexane) with elution proceeding as follows: 30% ethyl acetate/hexane (300 mL), to afford 0.059 g of product. In this fashion 0.399 g (73%) of (1R*,2R*)-1-(4-benzyloxy-3,5-difluorophenyl)-2-(4-fluorophenyl)-4-hydroxypiperidin-1-yl)-propan-1-ol was obtained and had: mp 169–171° C.; NMR δ7.53–7.44 (m, 4 H), 7.41–7.30 (m, 3 H), 7.06 (long range coupled t, J=8.7 Hz, 2 H), 6.92 (long range coupled d, J=8.9 Hz, 2 H), 5.27 (s, 1 H), 5.15 (s, 2 H), 4.18 (d, J=9.7 Hz, 1 H), 3.08 (dt, J=2.3, 11.6 Hz, 1 H), 2.71–2.68 (m, 2 H), 2.59–2.48 (m, 2 H), 2.26–2.01 (m, 2 H), 1.83 (br d, J=13.9 Hz, 2 H), 1.57 (s, 1 H), 0.86 (d, J=6.7 Hz, 3 H).

The product of the above reaction (0.34 g, 0.721 mmol) was dissolved in tetrahydrofuran (10 mL) and methanol (10 mL) and ammonium formate (0.45 g, 7.14 mmol), and 10% palladium on carbon (0.19 g) were added. The reaction was stirred 2 h at ambient temperature and then filtered through diatomaceous earth. The filter pad was rinsed with ethanol and water. The filtrate was concentrated and the residue was partitioned between ethyl acetate and water. The phases were separated and the organic layer was washed with water and brine, dried over magnesium sulfate and concentrated to leave no material. The magnesium sulfate filter pad was dissolved in water and a gray solid was filtered, rinsed with water and air dried. The gray solid weighed 0.195 g and was purified by flash chromatography on silica gel (1×4 inches). Elution proceeded as follows: 50% ethyl acetate/hexane (100 mL), nil; ethyl acetate (200 mL), nil; 10% methanol/ethyl acetate (200 mL), nil; 25% methanol/ethyl acetate (200 mL) and 50% methanol/ethyl acetate (200 mL), 0.097 g (36%) of (1R*,2R*)-1-(3,5-difluoro-4-hydroxyphenyl)-2-(4-(4-fluorophenyl)-4-hydroxypiperidin-1-yl)-propan-1-ol as a white solid. The product was converted to its mesylate salt. It was slurried in methanol (10 mL) and methanesulfonic acid (0.017 mL, 0.262 mmol) was added. The mixture was filtered and concentrated; then the residue was recrystallized from 9:1 ethanol/water to give the mesylate salt as a crystalline white solid (0.099 g) which had: mp 239–239.5° C. Analysis calculated for $C_{20}H_{22}F_3NO3.CH_4SO_3$: C, 52.82; H, 5.49; N, 2.93. Found: C, 52.80; H, 5.76; N, 2.99.

Example 11

(1R*,2R*)-1-(3,5-Difluoro-4-hydroxyphenyl)-2-(4-(4-trifluoromethylphenyl)-4-hydroxypiperidin-1-yl)-propan-1-ol mesylate A mixture of 4-benzyloxy-3,5-difluoro-α-bromopropiophenone (the compound of Preparation 22, 1.14 g, 3.21 mmol), 4-(4-trifluoromethylphenyl)-4-hydroxypiperidine (0.87 g, 3.55 mmol) and triethylamine (0.90 mL, 6.5 mmol) in ethanol (25 mL) was refluxed 1.75 h and allowed to stir at ambient temperature overnight. The solvent was removed at reduced pressure and the residue was partitioned between ethyl acetate and water. The phases were separated and the organic layer was washed with brine, dried over magnesium sulfate and concentrated. The residue was flash chromatographed on silica gel (1×4 inches packed in hexane) with elution proceeding as follows: 15% ethyl acetate/hexane (500 mL), nil; 25% ethyl acetate/hexane (250 mL), 1.09 g (65%) of 1-(4-benzyloxy-3,5-difluorophenyl)-2-(4-(4-trifluoromethylphenyl)-4-hydroxypiperidin-1-yl)-propan-1-one as a light orange oil which was suitable for use without further purification and had: NMR δ7.74 (long range coupled d, J=9.4 Hz, 2 H), 7.61 (s, 4 H), 7.48–7.34 (m, 5 H), 5.32 (s, 2 H), 4.03 (q, J=6.7 Hz, 1 H), 2.95–2.83 (m, 2 H), 2.67–2.62 (m, 2 H), 2.16–1.98 (m, 2 H), 1.81–1.67 (m, 2 H), 1.57 (br s, 1 H), 1.31 (d, J=6.8 Hz, 3 H).

A mixture of sodium borohydride (0.085 g, 2.25 mmol) and ethanol (5 mL) was stirred 10 min and then 1-(4-benzyloxy-3,5-difluorophenyl)-2-(4-(4-trifluoromethylphenyl)-4-hydroxypiperidin-1-yl)-propan-1-one (1.02 g, 1.96 mmol in 30 mL of ethanol) was added. The reaction was stirred at ambient temperature overnight. The white solid which precipitated was collected by filtration and dried to yield 0.66 g (65%) of (1R*, 2R*)-1-(4- benzyloxy-3,5-difluorophenyl)-2-(4-(4-trifluoromethylphenyl)-4-hydroxypiperidin-1-yl)-propan-1-ol which was suitable for use without further purification and had: mp 201–202° C.

Analysis calculated for $C_{28}H_{28}F_5NO_3.0.25\ H_2O$: C, 63.93; H, 5.46; N, 2.66. Found: C, 63.98; H, 5.49; N, 2.70.

The product of the above reaction (0.60 g, 1.15 mmol) was dissolved in tetrahydrofuran (15 mL) and methanol (15 mL) and ammonium formate (0.73 g, 11.6 mmol), and 10% palladium on carbon (0.30 g) were added. The reaction was stirred 2 h at ambient temperature and then filtered through diatomaceous earth. The filter pad was rinsed with ethanol and water. The filtrate was concentrated and the residue was partitioned between ethyl acetate and water. The phases were separated and the organic layer was washed with water and brine, dried over magnesium sulfate and concentrated to leave 0.517 g of (1R*,2R*)-1-(3,5-difluoro-4-hydroxyphenyl)-2-(4-(4-trifluoromethylphenyl)-4-hydroxypiperidin-1-yl)-propan-1-ol as a white solid. A sample (0.50 g, 1.16 mmol) was converted to its mesylate salt. It was slurried in methanol (15 mL) and methanesulfonic acid (0.075 mL, 1.16 mmol) was added. The mixture was filtered and concentrated; then the residue was recrystallized from 9:1 ethanol/water to give the mesylate salt as a fluffy white solid (0.475 g) which had: mp 218–219° C. Analysis calculated for $C_{22}H_{22}F_5NO_3.CH_4SO_3.0.75\ H_2O$: C, 48.84; H, 5.12; N, 2.59. Found: C, 48.88; H, 5.37; N, 2.59.

Example 12

(1R*,2R*)-1-(3-Fluoro-4-hydroxyphenyl)-2-(4-(4-chlorophenyl)-4-hydroxypiperidin-1-yl)-propan-1-ol mesylate A mixture of 3-fluoro-4-triisopropylsilyloxy-α-bromopropiophenone (the compound of Preparation 11, 1.25 g, 3.10 mmol), 4-(4-chlorophenyl)-4-hydroxypiperidine (1.0 g, 4.03 mmol) and triethylamine (1.51 mL, 10.85 mmol) in ethanol (25 mL) was refluxed 4 h. The solvent was removed at reduced pressure and the residue was partitioned between ethyl acetate and water. The phases were separated and the organic layer was washed with brine, dried over calcium sulfate and concentrated. The residue was flash chromatographed on silica gel (1×3.5 inches packed with 10% ethyl acetate/hexane) with elution proceeding as follows: hexane (150 mL), nil; 10% ethyl acetate/hexane (350 mL), nil; 20% ethyl acetate/hexane (300 mL), 0.535 g (32%) of 1-(3-fluoro-4-triisopropylsilyloxyphenyl)-2-(4-(4-chlorophenyl)-4-hydroxypiperidin-1 -yl)-propan-1-one as a yellow oily foam which had: NMR δ7.87 (dd, J=2, 11.5 Hz, 1 H), 7.80 (d, J=8.5 Hz, 1 H), 7.39 (d, J=8.5 Hz, 2 H), 7.28 (d, J=8.5 Hz, 2 H), 6.95 (t, J=8.5 Hz, 1 H), 4.07 (q, J=7 Hz, 1 H), 2.95–2.78 (m, 2 H), 2.78–2.57 (m, 2 H), 2.04 (sym m, 2 H), 1.78–1.64 (m, 2 H), 1.30 (d, J=7 Hz, 3 H), 1.10 (d, J=7 Hz, 18 H).

A mixture of sodium borohydride (0.032 g, 0.85 mmol) and ethanol (5 mL) was stirred 10 min and then 1-(3-fluoro-4-triisopropylsilyloxyphenyl)-2-(4-(4-chlorophenyl)-4-hydroxypiperidin-1-yl)-propan-1-one (0.454 g, 0.850 mmol in 10 mL of ethanol) was added. The reaction was stirred at ambient temperature overnight. The white precipitate which formed was collected by filtration to afford 0.245 g (54%) of (1R*, 2R*)-1-(3-fluoro-4-triisopropylsilyloxyphenyl)-2-(4-(4-chlorophenyl)-4-hydroxypiperidin-1-yl)-propan-1-ol which had: NMR δ7.39 (ABq, Δν$_{1-3}$=35.2 Hz, J=8.5 Hz, 4 H), 7.06 (dd, J=2, 11.5 Hz, 1 H), 6.96–6.82 (m, 2 H), 5.15 (s, 1 H), 4.18 (d, J=9.5 Hz, 1 H), 3.04 (dt, J=2.5, 11.5 Hz, 1 H), 2.78–2.67 (m, 1 H), 2.67–2.52 (m, 3 H), 2.12 (sym m, 2 H), 1.80 (distorted d, J=14 Hz, 2 H), 1.54 (s, 1 H), 1.36–1.19 (m, 3 H), 1.08 (d, J=7 Hz, 18 H), 0.80 (d, J=6.5 Hz, 3 H). The product also contained about 8% of the erythro diastereomer but was suitable for use without additional purification.

The product of the above reaction (0.220 g, 0.41 mmol) was dissolved in tetrahydrofuran (10 mL) and tetrabutylammonium fluoride (0.452 mL, 0.45 mmol, 1 M tetrahydrofuran solution) was added. The reaction was stirred 30 min at ambient temperature and then concentrated. The residue was partitioned between ethyl acetate and water and the phases were separated. The organic layer was washed with brine, dried over calcium sulfate, and concentrated. The residue was flash chromatographed on silica gel (0.75×3.5 inches) with elution proceeding as follows: 5% ethyl acetate/hexane (100 mL), nil; 15% ethyl acetate/hexane (200 mL), nil; 25% ethyl acetate/hexane (200 mL), nil; 35% ethyl acetate/hexane (200 mL), nil; 35% ethyl acetate/hexane (200 mL), 0.106 g (68%) of white solid product. The solid was slurried in methanol (4 mL) and methanesulfonic acid (0.018 mL, 0.28 mmol) was added. The mixture was filtered, then concentrated at the boil to 0.5 mL with addition of a few drops of ethanol. Cooling gave white crystals which were collected by filtration to afford 0.084 g, (43%) of (1R*,2R*)-1-(3-fluoro-4-hydroxyphenyl)-2-(4-(4-chlorophenyl)-4-hydroxypiperidin-1-yl)-propan-1-ol mesylate which had: mp 233–235° C. Analysis calculated for $C_{20}H_{23}ClFNO_3 \cdot CH_4SO_3$: C, 52.99; H, 5.72; N, 2.94. Found: C, 53.06; H, 5.91; N, 3.03.

Example 13

(1R*,2R*)-1-(3-Fluoro-4-hydroxyphenyl)-2-(4-(4-trifluoromethylphenyl)-4-hydroxypiperidin-1-yl)-propan-1-ol mesylate A mixture of 3-fluoro-4-triisopropylsilyloxy-α-bromopropiophenone (the compound of Preparation 11, 1.35 g, 3.35 mmol), 4-(4-trifluoromethylphenyl)-4-hydroxypiperidine (1.15 g, 4.69 mmol) and triethylamine (1.20 mL, 8.38 mmol) in ethanol (25 mL) was refluxed 4 h. The solvent was removed at reduced pressure and the residue was partitioned between ethyl acetate and water. The phases were separated and the organic layer was washed with brine, dried over calcium sulfate and concentrated. The residue was flash chromatographed on silica gel (1×3.5 inches packed with 10% ethyl acetate/hexane) with elution proceeding as follows: hexane (150 mL), nil; 10% ethyl acetate/hexane (350 mL), nil; 20% ethyl acetate/hexane (350 mL), 0.841 g (44%) of 1-(3-fluoro-4-triisopropylsilyloxyphenyl)-2-(4-(4-trifluoromethylphenyl)-4-hydroxypiperidin-1-yl)-propan-1-one as a yellow oily foam which had: NMR δ7.88 (dd, J=2, 11.5 Hz, 1 H), 7.80 (sym m, 1 H), 7.60–7.57 (m, 4 H), 6.96 (t, J=8.5 Hz, 1 H), 4.08 (q, J=7 Hz, 1 H), 3.32 (br m, 1 H), 2.95–2.78 (m, 2 H), 2.78–2.56 (m, 2 H), 2.08 (sym m, 2 H), 1.78–1.63 (m, 2 H), 1.31 (d, J=7 Hz, 3 H), 1.10 (d, J=7 Hz, 18 H).

A mixture of sodium borohydride (0.049 g, 1.30 mmol) and ethanol (5 mL) was stirred 10 min and then 1-(3-fluoro-4-triisopropylsilyloxyphenyl)-2-(4-(4-trifluoromethylphenyl)-4-hydroxypiperidin-1-yl)-propan-1-one (0.738 g, 1.30 mmol in 10 mL of ethanol) was added with a 5 mL ethanol rinse. The reaction was stirred at ambient temperature overnight. The white precipitate which formed was collected by filtration to afford 0.335 g (45%) of (1R*,2R*)-1-(3-fluoro-4-triisopropylsilyloxyphenyl)-2-(4-(4-trifluoromethylphenyl)-4-hydroxypiperidin-1-yl)-propan-1-ol which had: NMR δ7.63 (s, 4 H), 7.07 (dd, J=2, 11.5 Hz, 1 H), 6.98–6.84 (m, 2 H), 5.13 (s, 1 H), 4.20 (d, J=9.5 Hz, 1 H), 3.06 (sym m, 1 H), 2.81–2.71 (m, 1 H), 2.70–2.50 (m, 3 H), 2.15 (sym m, 2 H), 1.81 (distorted d, J=14 Hz, 2 H), 1.59 (s, 1 H), 1.33–1.19 (m, 3 H), 1.08 (d, J=7 Hz, 18 H), 0.81 (d, J=6.5 Hz, 3 H). The product also contained about 7% of the erythro diastereomer but was suitable for use without additional purification.

The product of the above reaction (0.300 g, 0.527 mmol) was dissolved in tetrahydrofuran (10 mL) and tetrabutylammonium fluoride (0.58 mL, 0.58 mmol, 1 M tetrahydrofuran solution) was added. The reaction was stirred 30 min at ambient temperature and then concentrated. The residue was partitioned between ethyl acetate and water and the phases were separated. The organic layer was washed with brine, dried over calcium sulfate, and concentrated. The residue was flash chromatographed on silica gel (0.75×3.5 inches) with elution proceeding as follows: 5% ethyl acetate/hexane (100 mL), nil; 15% ethyl acetate/hexane (200 mL), nil; 25% ethyl acetate/hexane (200 mL), nil; 35% ethyl acetate/hexane (350 mL), 0.156 g (72%) of white solid product. The solid was slurried in methanol (4 mL) and methanesulfonic acid (0.025 mL, 0.38 mmol) was added. The mixture was filtered, then concentrated. The residue was recrystallized from ethanol to yield 0.085 g, (32%) of (1R*,2R*)-1-(3-fluoro-4-hydroxyphenyl)-2-(4-(4-trifluoromethylphenyl)-4-hydroxypiperidin-1-yl)-propan-1-ol mesylate which had: mp 155–157° C. Analysis calculated for $C_{21}H_{23}F_4NO_3 \cdot CH_4SO_3$: C, 51.86 H, 5.34; N, 2.75. Found: C, 51.94; H, 5.58; N, 2.76.

Example 14

(1R*,2R*)-4-{2-(3-(4-Chlorophenylsulfanyl)-8-azabicyclo(3.2.1)oct-8-yl)-1-hydroxypropyl}-2-methylphenol A mixture of 3-methyl-4-triisopropylsilyloxy-α-bromopropiophenone (the compound of Preparation 6, 1.25 g, 3.14 mmol), 3-(4-chlorophenylsulfanyl)-8-azabicyclo (3.2.1)octane (the compound of Preparation 41, 1.11 g, 4.40 mmol) and triethylamine (1.09 mL, 7.85 mmol) in ethanol (17 mL) was refluxed 16 h. The solvent was removed at reduced pressure and the residue was partitioned between methylene chloride and water. The phases were separated and the organic layer was washed with brine, dried over calcium sulfate and concentrated. The residue was flash chromatographed on silica gel (1×4 inches packed with hexane) with elution proceeding as follows: hexane (150 mL), nil; 5% ethyl acetate/hexane (300 mL), discarded forerun; 10% ethyl acetate/hexane (200 mL) and 20% ethyl acetate/hexane (150 mL), 1.325 g (74%) of 1-(3-methyl-4-triisopropylsilyloxyphenyl)-2-{3-(4-chlorophenylsulfanyl)-8-azabicyclo(3.2.1)octan-8-yl}-propan-1-one as a yellow oil which was used directly in the next step.

A mixture of sodium borohydride (0.082 g, 2.18 mmol) and ethanol (10 mL) was stirred 10 min and then 1-(3-methyl-4-triisopropylsilyloxyphenyl)-2-{3-(4-chlorophenylsulfanyl)-8-azabicyclo(3.2.1)octan-8-yl}-propan-1-one (1.247 g, 2.18 mmol in 5 mL of ethanol) was added with 2×5 mL ethanol rinses. The reaction was stirred at ambient temperature overnight, then concentrated. The residue was partitioned between methylene chloride and water and the phases were separated. The organic phase was washed with brine, dried, and concentrated. The residue was flash chromatographed on silica gel (1×4 inches) with elution proceeding as follows: 10% ethyl acetate/hexane (200 mL), nil; 20% ethyl acetate/hexane (500 mL), 0.475 g (38%) of (1R*,2R*)-1-(3-methyl-4-triisopropylsilyloxyphenyl)-2-{3-(4-chlorophenylsulfanyl)-8-azabicyclo(3.2.1)octan-8-yl}-propan-1-ol as an oil which had: NMR δ7.29 (ABq, $\Delta v_{1-3}$=23 Hz, J=8.5 Hz, 4 H), 7.07 (d, J=2 Hz, 1 H), 6.94 (dd, J=2, 8 Hz, 1 H), 6.70 (d, J=8 Hz, 1 H), 5.11 (br s, 1 H), 4.00 (d, J=8 Hz, 1 H), 3.42 (br s, 1 H), 3.27 (sym m, 1 H), 3.16

(br s, 1 H), 2.59 (sym m, 1 H), 2.20 (s, 3 H), 1.90–1.51 (m, 8 H), 1.34–1.20 (m, 3 H), 1.08 (d, J=7 Hz, 18 H), 0.79 (d, J=6.5 Hz, 3 H). The product also contained about 10% of the erythro diastereomer but was suitable for use without additional purification. Note that further elution of the flash chromatography column with 25% ethyl acetate/hexane (250 mL) and 30% ethyl acetate/hexane (200 mL) afforded 0.291 g of the erythro diastereomer as an oil.

The product of the above reaction (0.475 g, 0.828 mmol) was dissolved in tetrahydrofuran (14 mL) and tetrabutylammonium fluoride (0.91 mL, 0.91 mmol, 1 M tetrahydrofuran solution) was added. The reaction was stirred 1 h at ambient temperature and then concentrated. The residue was partitioned between methylene chloride and water and the phases were separated. The organic layer was washed with brine, dried, and concentrated. The residue was flash chromatographed on silica gel (0.75×3 inches) with elution proceeding as follows: 20% ethyl acetate/hexane (150 mL), nil; 30% ethyl acetate/hexane (200 mL) and 40% ethyl acetate/hexane (300 mL), 0.183 g (52%) of (1R*,2R*)-4-{2-(3-(4-chlorophenylsulfanyl)-8-azabicyclo(3.2.1)oct-8-yl)-1-hydroxypropyl}-2-methylphenol as a white solid product. A sample recrystallized from ethyl acetate had: mp 168–169° C.; NMR δ7.31 (ABq, $\Delta v_{1-3}$=19.5 Hz, J=8.5 Hz, 4 H), 7.09 (d, J=2 Hz, 1 H), 7.00 (dd, J=2, 8 Hz, 1 H), 6.68 (d, J=8 Hz, 1 H), 5.10 (br s, 2 H), 4.02 (d, J=8 Hz, 1 H), 3.45 (br s, 1 H), 3.30 (sym m, 1 H), 3.22 (br s, 1 H), 2.62 (sym m, 1 H), 2.23 (s, 3 H), 1.92–1.68 (m, 5 H), 1.68–1.55 (m, 3 H), 0.82 (d, J=6.5 Hz, 3 H).

Example 15

(1R*,2R*)-4-{2-(3-(4-Chlorophenylsulfanyl)-8-azabicyclo(3.2.1)oct-8-yl)-1-hydroxypropyl}-2,6-dimethylphenol A mixture of 3,5-dimethyl-4-triisopropylsilyloxy-α-bromopropiophenone (the compound of Preparation 41, 1.3 g, 3.14 mmol), 3-(4-chlorophenylsulfanyl)-8-azabicyclo (3.2.1)octane (1.11 g, 4.40 mmol) and triethylamine (1.09 mL, 7.85 mmol) in ethanol (17 mL) was refluxed 16 h. The solvent was removed at reduced pressure and the residue was partitioned between methylene chloride and water. The phases were separated and the organic layer was washed with brine, dried over calcium sulfate and concentrated. The residue was flash chromatographed on silica gel (1×4 inches packed with hexane) with elution proceeding as follows: hexane (150 mL), nil; 5% ethyl acetate/hexane (300 mL), discarded forerun; 10% ethyl acetate/hexane (200 mL) and 20% ethyl acetate/hexane (150 mL), 1.175 g (64%) of 1-(3,5-dimethyl-4-triisopropylsilyloxyphenyl)-2-{3-(4-chlorophenylsulfanyl)-8-azabicyclo(3.2.1)octan-8-yl}-propan-1-one as a yellow oil which was used directly in the next step.

A mixture of sodium borohydride (0.070 g, 1.86 mmol) and ethanol (10 mL) was stirred 10 min and then 1-(3,5-dimethyl-4-triisopropylsilyloxyphenyl)-2-{3-(4-chlorophenylsulfanyl)-8-azabicyclo(3.2.1)octan-8-yl}-propan-1-one (1.09 g, 2.86 mmol in 5 mL of ethanol) was added with 3×5 mL ethanol rinses. The reaction was stirred at ambient temperature overnight. The white precipitate which formed was collected and dried to give 0.22 g of the erythro product (1R*,2S*). The filtrate was concentrated and the residue was partitioned between methylene chloride and water. The phases were separated and the organic phase was washed with brine, dried, and concentrated. The residue was flash chromatographed on silica gel (1×3.5 inches) with elution proceeding as follows: 10% ethyl acetate/hexane (200 mL), nil; 20% ethyl acetate/hexane (500 mL), 0.208 g (19%) of (1R*,2R*)-1-(3,5-dimethyl-4-triisopropylsilyloxyphenyl)-2-{3-(4-chlorophenylsulfanyl)-8-azabicyclo(3.2.1)octan-8-yl}-propan-1-ol as an oil which had: NMR δ7.29 (ABq, $\Delta v_{1-3}$=22.5 Hz, J=8.5 Hz, 4 H), 6.88 (s, 2 H), 5.08 (br s, 1 H), 3.98 (d, J=7.5 Hz, 1 H), 3.41 (br s, 1 H), 3.26 (sym m, 1 H), 3.14 (br s, 1 H), 2.60 (sym m, 1 H), 2.22 (s, 6 H), 1.90–1.50 (m, 8 H), 1.34–1.20 (m, 3 H), 1.08 (d, J=7 Hz, 18 H), 0.80 (d, J=6.5 Hz, 3 H). The product contained >10% of the erythro diastereomer and was suitable for use without additional purification. Further elution of the flash chromatography column with 20% ethyl acetate/hexane (250 mL) afforded 0.126 g of the erythro diastereomer as an oil for a total yield of 0.346 g of erythro product.

The product of the above reaction (0.196 g, 0.33 mmol) was dissolved in tetrahydrofuran (7 mL) and tetrabutylammonium fluoride (0.37 mL, 0.37 mmol, 1 M tetrahydrofuran solution) was added. The reaction was stirred 1 h at ambient temperature and then concentrated. The residue was partitioned between methylene chloride and water and the phases were separated. The organic layer was washed with brine, dried, and concentrated. The residue was flash chromatographed on silica gel (0.75×2.5 inches) with elution proceeding as follows: 20% ethyl acetate/hexane (140 mL), nil; 30% ethyl acetate/hexane (200 mL) and 40% ethyl acetate/hexane (75 mL), 0.144 g (100%) of (1R*,2R*)-4-{2-(3-(4-chlorophenylsulfanyl)-8-azabicyclo(3.2.1)oct-8-yl)-1-hydroxypropyl}-2,6-dimethylphenol as a light yellow oil. A sample recrystallized from ethyl acetate had: mp 143–144.5° C.; NMR δ7.31 (ABq, $\Delta v_{1-3}$=19.5 Hz, J=8.5 Hz, 4 H), 6.93 (s, 2 H), 5.19 (br s, 1 H), 4.59 (br s, 1 H), 3.98 (d, J=8.5 Hz, 1 H), 3.45 (br s, 1 H), 3.29 (sym m, 1 H), 3.22 (br s, 1 H), 2.62 (sym m, 1 H), 2.23 (s, 6 H), 1.95–1.56 (m, 8 H), 0.81 (d, J=6.5 Hz, 3 H).

Example 16

3R*,4S* 6-Fluoro-3-(4-(4-fluorophenyl)-4-hydroxypiperidin-1-yl)-chroman-4,7-diol A mixture of 3,3-dibromo-6-fluoro-7-benzyloxychroman-4-one (the compound of Preparation 31, 0.91 g, 2.12 mmol), 4-(4-fluorophenyl)-4-hydroxypiperidine (0.83 g, 4.25 mmol) and triethylamine (0.60 mL, 4.30 mmol) in acetonitrile (30 mL) was stirred overnight at ambient temperature. The yellow precipitate which formed was collected by filtration. This material was flash chromatographed on silica gel (1×4 inches packed in methylene chloride) with elution proceeding as follows: 2% methanol/methylene chloride (200 mL), nil; 3% methanol/methylene chloride (100 mL), 0.16 g (16%) 7-benzyloxy-6-fluoro-3-(4-(4-fluorophenyl)-4-hydroxypiperidin-1-yl)-chromen-4-one which was used without further purification.

A mixture of sodium borohydride (0.13 g, 3.44 mmol) and ethanol (5 mL) was stirred 10 min and then 7-benzyloxy-6-fluoro-3-(4(4-fluorophenyl)-4-hydroxypiperidin- 1-yl)-chromen-4-one (0.16 g, 0.345 mmol in 10 mL of ethanol) was added. The reaction was stirred at ambient temperature overnight. The reaction was quenched with water and concentrated. The residue was triturated with water and filtered to give 0.136 g of a white solid which was carried directly to the next step.

The product of the above reaction (0.13 g, 0.28 mmol) was dissolved in tetrahydrofuran (6 mL) and methanol (6 mL) and ammonium formate (0.18 g, 2.85 mmol), and 10% palladium on carbon (0.09 g) were added. The reaction was stirred overnight at ambient temperature and then filtered through diatomaceous earth. The filter pad was rinsed with methanol. The filtrate was concentrated and the residue was stirred vigorously with aqueous bicarbonate. The solids (0.057 g) were collected and recrystallized from ethanol to give 0.022 g (20%) of (3R*,4S*)-6-fluoro-3-(4-(4-fluorophenyl)-4-hydroxypiperidin-1-yl)-chroman-4,7-diol as a white solid which had: mp 160–161° C.; NMR (DMSO-d$_6$) δ9.84 (br s, 1 H), 7.50 (dd, J=5.6, 8.9 Hz, 2 H), 7.11 (t, J=8.9 Hz, 2 H), 6.95 (d, J=11.4 Hz, 1 H), 6.31 ((d, J=7.7 Hz, 1 H), 4.90 (br s, 1 H), 4.86 (s, 1 H), 4.62 (s, 1 H), 4.20 (dd, J=2.3, 10.3 Hz, 1 H), 4.02 (t, J=10.5 Hz, 1 H), 2.95 (br d, J=10.8 Hz, 1 H), 2.85 (br d, J=10.9 Hz, 1 H), 2.73–2.60 (m, 2 H), 2.57–2.52 (m, 1 H partially obscured by NMR solvent), 1.96–1.86 (m, 2 H), 1.56 (br d, J=13.4 Hz, 2 H).

Example 17

(3R*,4S*)-5-Bromo-6- methyl-3-(4-(4-fluorophenyl)-4-hydroxypiperidin-1-yl)-chroman-4,7-diol A mixture of 3,3-dibromo-6-methyl-7-triisopropylsilyloxychroman-4-one and 6-methyl-3,3,5-tribromo-7-triisopropylsilyloxychroman-4-one (the compounds of Preparation 34, 1.0 g), 4-(4-(fluorophenyl)-4-hydroxypiperidine (0.79 g, 4.05 mmol) and triethylamine (0.60 mL, 4.30 mmol) in acetonitrile (30 mL) was stirred 30 min at ambient temperature. The precipitate which formed was collected by filtration to afford 0.188 g of 5-bromo-6-methyl-7-triisopropylsilyloxy-3-(4-(4-fluorophenyl)-4-hydroxypiperidin-1-yl)-chromen-4-one. The filtrate was flash chromatographed on silica gel (1×4 inches packed in hexane) with elution proceeding as follows: 20% ethyl acetate/hexane (100 mL), 0.115 g of 6-methyl-7-triisopropylsilyloxy-3-(4-(4-fluorophenyl)-4-hydroxypiperidin- 1-yl)-chromen-4-one as a light yellow solid which had mp 193–195° C.; 20% ethyl acetate/hexane (100 mL) and 40% ethyl acetate/hexane (100 mL), 0.07 g of a mixture; 40% ethyl acetate/hexane (100 mL) and 60% ethyl acetate/hexane (400 mL), 0.30 g of 6-methyl-7-hydroxy-3-(4-(4-fluorophenyl)-4-hydroxypiperidin-1-yl)-chromen-4-one.

A mixture of sodium borohydride (0.11 g, 2.91 mmol) and ethanol (5 mL) was stirred 10 min and then 5-bromo-6-methyl-7-triisopropylsilyloxy-3-(4-(4-fluorophenyl)-4-hydroxypiperidin-1-yl)-chromen-4-one (0.15 g, 0.285 mmol in 10 mL of ethanol and 5 mL of tetrahydrofuran) was added. The reaction was stirred at ambient temperature over the weekend. The reaction was quenched with water and concentrated. The residue was triturated with water and filtered to give 0.14 g of a cream colored solid. The solid was flash chromatographed on silica gel (1×3.5 inches packed with hexane) with elution proceeding as follows: 20% ethyl acetate/hexane (200 mL) and 30% ethyl acetate/hexane (100 mL), nil; 30% ethyl acetate/hexane (100 mL) and 50% ethyl acetate/hexane (150 mL), 0.094 g (63%) of (3R*,4S*)-5-bromo-6-methyl-7-triisopropylsilyloxy-3-(4-(4-fluorophenyl)-4-hydroxypiperidin-1-yl)-chroman-4-ol as a pale yellow solid which had: mp 201–202.5° C. Analysis calculated for C$_{30}$H$_{43}$BrFNO$_4$Si: C, 59.20, H, 7.12; N, 2.23. Found: C, 59.30; H, 7.41; N, 2.25.

The product of the above reaction (0.09 g, 0.17 mmol) was dissolved in tetrahydrofuran (5 mL) and tetrabutylammonium fluoride (0.175 mL, 0.175 mmol, 1 M tetrahydrofuran solution) was added. The reaction was stirred overnight at ambient temperature and then concentrated. The residue was flash chromatographed on silica gel (1×3 inches packed with hexane) with elution proceeding as follows: 20% ethyl acetate/hexane (200 mL), nil; 40% ethyl acetate/hexane (200 mL), nil; 60% ethyl acetate/hexane (100 mL), nil; 60% ethyl acetate/hexane (100 mL), 0.045 g (71%) of (3R*,4S*)-5-bromo-6-methyl-3-(4-(4-fluorophenyl)-4-hydroxypiperidin-1-yl)-chroman-4,7-diol as a light white solid. The sample was recrystallized from ethanol/ether to afford 0.035 g of product which had: mp 195.5–196° C. Analysis calculated for C$_{21}$H$_{23}$BrFNO$_4$: C, 55.76; H, 5.13; N, 3.10. Found: C, 55.70; H, 5.23; N, 3.07.

Example 18

(3R*,4S*)-Methyl-3-(4-(4-fluorophenyl)-4-hydroxypiperidin-1-yl)-chroman-4,7-diol A mixture of 6-methyl-7-hydroxy-3-(4-(4-fluorophenyl)-4-hydroxypiperidin-1-yl)-chromen-4-one (the compound of example 17, 0.30 g, 0.81 mmol), potassium carbonate (0.22 g, 1.59 mmol), and benzyl bromide (0.10 mL, 0.84 mmol) in acetone was refluxed 6 h. The reaction was concentrated and the residue was partitioned between 2:1 ethyl acetate/tetrahydrofuran and water with warming to help effect dissolution. The phases were separated and the organic layer was washed with water and brine. The organic phase was dried over magnesium sulfate and concentrated to a yellow solid. This solid was triturated with ether to give 0.31 g (84%) of 7-benzyloxy-6-methyl-3-(4-(4-fluorophenyl)-4-hydroxypiperidin-1-yl)-chromen-4-one which had: mp 245–245.5° C. Analysis calculated for C$_{28}$H$_{26}$FNO$_4$: C, 73.19; H, 5.70; N, 3.05. Found: C, 72.87; H, 5.76; N, 3.21.

A mixture of sodium borohydride (0.25 g, 6.61 mmol) and ethanol (5 mL) was stirred 10 min and then 7-benzyloxy-6-methyl-3-(4-(4-fluorophenyl)-4-hydroxypiperidin-1-yl)-chromen-4-one (0.30 g, 0.653 mmol in 20 mL of ethanol and 15 mL of tetrahydrofuran) was added. The reaction was stirred at ambient temperature overnight. Additional sodium borohydride (0.12 g) was added and stirring was continued over the weekend. The reaction was quenched with water and concentrated. The residue was triturated with water and filtered to give a solid which was a 2:1 mixture of starting material and product. This material was stirred with hot ethanol and filtered. The solid which was collected weighed 0.2 g and was pure starting material which could be recycled in this reduction step. The ethanol filtrate was concentrated to afford 0.113 g of (3R*,4S*)-7-benzyloxy-6-methyl-3-(4-(4-fluorophenyl)-4-hydroxypiperidin-1-yl)-chroman-4-ol which had: mp 201–202° C. This material was carried directly to the next step.

The product of the above reaction (0.080 g, 0.173 mmol) was dissolved in tetrahydrofuran (3 mL) and ethanol (3 mL) and ammonium formate (0.14 g, 2.22 mmol, and 10% palladium on carbon (0.06 g) were added. The reaction was stirred over the weekend at ambient temperature and then filtered through diatomaceous earth. The filter pad was rinsed with tetrahydrofuran and ethanol. The filtrate was concentrated and the residue was triturated with water. The solids (0.045 g) were collected and recrystallized from ethanol/ether to give 0.030 g (46%) of (3R*,4S*)-6-methyl-3-(4-(4-fluorophenyl)-4-hydroxypiperidin-1-yl)-chroman-4,7diol as a white solid which had: mp 173.5–174° C.; NMR (DMSO-d$_6$) δ9.10 (s, 1 H), 7.37–7.32 (m, 2 H), 6.94 (t, J=8.9 Hz, 2 H), 6.71 ((s, 1 H), 6.02 (s, 1 H), 4.69 ( s, 1 H), 4.55 (d, J=4.3 Hz, 1 H), 4.43 (br s, 1 H), 4.01 (d, J=7.7 Hz, 1 H), 3.83 (t, J=10 Hz, 1 H), 2.81 (br d, J=11.2 Hz, 1 H), 2.69 (br d, J=10.8 Hz, 1 H), 2.55–2.43 (m, 2 H), 1.85 (s, 3 H), 1.79–1.71 (m, 2 H), 1.40 (br d, J=13.3 Hz, 2 H).

Example 19

(3R*,4S*)-6,8-Dimethyl-3-(4-(4-fluorophenyl)-4-hydroxypiperidin-1-yl)-chroman-4,7-diol A mixture of 3,3-dibromo-6,8-dimethyl-7-triisopropylsilyloxychroman-4-one (the compound of Preparation 28, 0.62 g, 1.22 mmol), 4-(4-fluorophenyl)-4-hydroxypiperidine (0.48 g, 2.46 mmol) and triethylamine (0.68 mL, 4.88 mmol) in acetonitrile (20 mL) was stirred overnight at ambient temperature. The reaction was filtered and the filtrate was concentrated. The residue was partitioned between ethyl acetate and water. The phases were separated and the organic layer was washed with water and brine, dried over magnesium sulfate, and concentrated. This residue was flash chromatographed on silica gel (1×3 inches packed in hexane) with elution proceeding as follows: 10% ethyl acetate/hexane (250 mL), 0.23 g of 3-bromo-6,8-dimethyl-7-triisopropylsilyloxychromen-4-one; 20% ethyl acetate/hexane (250 mL), 0.14 g (21%) 6,8-dimethyl-7-triisopropylsilyloxy-3-(4-(4-fluorophenyl)-4-hydroxypiperidin-1-yl)-chromen-4-one which was used without further purification.

A mixture of sodium borohydride (0.082 g, 2.17 mmol) and ethanol (3 mL) was stirred 10 min and then 6,8-dimethyl-7-triisopropylsilyloxy-3-(4-(4-fluorophenyl)-4-hydroxypiperidin-1-yl)-chromen-4-one (0.117 g, 0.217 mmol in 12 mL of ethanol and 3 mL of tetrahydrofuran) was added. The reaction was stirred at ambient temperature overnight. The reaction was quenched with water and concentrated. The residue was triturated with water and filtered to give 0.110 g of a solid. This material was flash chromatographed on silica gel (1×4 inches packed with hexane) with elution proceeding as follows: 25% ethyl acetate/hexane (300 mL), nil; 25% ethyl acetate/hexane (300 mL), 0.064 g (54%) of (3R*,4S*)-6,8-dimethyl-7-triisopropylsilyloxy-3-(4-(4-fluorophenyl)-4-hydroxypiperidin-1-yl)-chroman-4-ol as a white solid which had: mp 198–199° C.; NMR δ7.46 (dd, J=5.5, 8.5 Hz, 2 h), 7.04 (t, J=8.7 Hz, 2 H), 6.95 (s, 1 h), 4.72 (d, J=2.8 Hz, 1 H), 4.38 (dd, J=2.9, 10.4 Hz, 1 H), 4.06 (t, J=10.5 Hz, 1 H), 3.09 (br d, J=11.1 Hz, 1 H), 2.80–2.68 (m, 4 H), 2.19 (s, 3 H), 2.11–2.02 (m, 4 H), 1.90–1.76 (m, 3 H), 1.38–1.21 (m, 3 H), 1.12 (d, J=7.1 Hz, 18 H).

The product of the above reaction (0.060 g, 0.110 mmol) was dissolved in tetrahydrofuran (5 mL) and tetrabutylammonium fluoride (0.115 mL, 0.115 mmol, 1 M tetrahydrofuran solution) was added. The reaction was stirred 1.5 h at ambient temperature and then concentrated. The residue was flash chromatographed on silica gel (1×4 inches packed with hexane) with elution proceeding as follows: 20% ethyl acetate/hexane (200 mL), nil; 50% ethyl acetate/hexane (200 mL), nil; 75% ethyl acetate/hexane (400 mL), a colorless oil, which solidified to afford 0.035 g (81%) of (3R*,4S*)-6,8-dimethyl-3-(4-(4-fluorophenyl)-4-hydroxypiperidin-1-yl)-chroman-4,7-diol as a white solid. The sample was recrystallized from ethanol/ether to afford 0.016 g of product in two crops which had: mp 185.5–186° C.; NMR (DMSO-$d_6$) δ8.17 (s, 1 H), 7.52 (dd, J=5.7, 8.7 Hz, 2 H), 7.12 (t, J=8.9 Hz, 2 H), 6.76 (s, 1 H), 4.86 (s, 1 H), 4.69 (s, 1 H), 4.61 (s, 1 H), 4.29 (br d, J=7.8 Hz, 1 H), 4.02 (t, J=10.5 Hz, 1 H), 3.01 (br d, J=10.7 Hz, 1 H), 2.89 (br d, J=12.4 Hz, 1 H), 2.72–2.60 (m, 2 H), 2.54–2.49 (m, 1 H, partially obscured by the NMR solvent), 2.08 (s, 3 H), 1.97–1.89 (s with overlapping m, 5 H), 1.58 (br d, J=13 Hz, 2 H).

Example 20

(3R*,4S*)-6,8-Dimethyl-3-(4-(4-fluorophenyl)-4-hydroxypiperidin-1-yl)-chroman-4,7-diol A mixture of 3-bromo-6,8-dimethyl-7-triisopropylsilyloxychromen-4-one (the compound of Example 19, 0.23 g, 0.54 mmol), 4-(4-fluorophenyl)-4-hydroxypiperidine (0.22 g, 1.12 mmol) and triethylamine (0.3 mL, 2.15 mmol) in acetonitrile (15 mL) was stirred over the weekend at ambient temperature. The precipitate which formed was collected and rinsed with water and ether. This solid was flash chromatographed on silica gel (1×4 inches packed in hexane) with elution proceeding as follows: 10% ethyl acetate/hexane (100 mL), nil; 25% ethyl acetate/hexane (200 mL), 0.065 g (22%) 6,8-dimethyl-7-triisopropylsilyloxy-3-(4-(4-fluorophenyl)-4-hydroxypiperidin-1-yl)-chromen-4-one which had: mp 226.5–227° C. Analysis calculated for $C_{31}H_{42}FNO_4Si$: C, 68.98; H, 7.84; N, 2.59. Found: C, 69.00; H, 7.94; N, 2.37. This product was identical to the product isolated in the first step of example 19 and was converted to the title product following the procedure of example 19.

Example 21

(1R*,2R*)-1-(4-Hydroxy-3-methoxyphenyl)-2-(4-hydroxy-4-phenyl-piperidin-1-yl)-propan-1-ol A mixture of 4-benzyloxy-α-bromo-3-methoxypropiophenone (the compound of Preparation 46, 1.00 g, 2.86 mmol), 4-hydroxy-4-phenylpiperidine (0.60 g, 3.39 mmol) and triethylamine (0.80 mL, 5.74 mmol) in ethanol (30 mL) was refluxed 3.5 h. The solvent was removed at reduced pressure and the residue was partitioned between ethyl acetate and water. The phases were separated and the organic layer was washed with brine, dried over magnesium sulfate and concentrated to afford 1.25 g (98%) of 1-(4-benzyloxy-3-methoxyphenyl)-2-(4-hydroxy-4-phenyl-piperidin-1-yl)-propan-1-one as light orange foam which was suitable for use without further purification and had: NMR δ7.76 (dd, J=2, 8.4 Hz, 2 H), 7.71 (d, J=2 Hz, 1 H), 7.49–7.23 (m, 10 H), 68.9 (d, J=8.4 Hz, 1 H), 5.22 (s, 2 H), 4.16–4.11 (m, 1 H), 3.93 (s, 3 H), 2.94–2.62 (m, 4 H), 2.13 (dq, J=4.3, 12.7 Hz, 2 H), 1.78–1.69 (m, 2 H), 1.32 (d, J=6.8 Hz, 3 H).

A mixture of sodium borohydride (0.10 g, 2.64 mmol) and ethanol (5 mL) was stirred 10 min and then 1-(4-benzyloxy-3-methoxyphenyl)-2-(4-hydroxy-4-phenyl-piperidin-1-yl)-propan-1-one (1.13 g, 2.54 mmol in 25 mL of ethanol) was added. The reaction was stirred at ambient temperature overnight. The reaction was quenched with water and concentrated at reduced pressure and 40° C. The residue was partitioned between ethyl acetate and water. The phases were separated and the organic layer was washed with water and brine, dried over magnesium sulfate and concentrated to afford 1.16 g of crude product which was a 5:1 mixture of (1R*,2R*) and (1R*,2S*) isomers. The mixture was recrystallized from ethanol/ether/hexane and then recrystallized from ethanol/ether to give 0.47 g (41%) of (1R*,2R*)-1-(4-benzyloxy-3-methoxyphenyl)-2-(4-hydroxy-4-phenyl-piperidin-1-yl)-propan-1-ol which had: mp 131–132° C. Analysis calculated for $C_{28}H_{33}NO_4$: C, 75.14; H, 7.43; N, 3.13. Found: C, 75.50; H, 7.33; N, 3.25.

A mixture of the product of the above reaction (0.40 g, 0.89 mmol) and 10% palladium on carbon (0.080 g) in methanol (25 mL) and acetic acid (0.5 mL) was hydrogenated at 50 psi (initial pressure) for 5.5 h at ambient temperature and then filtered through diatomaceous earth. The filter pad was rinsed with methanol. The filtrate was concentrated and the residue was partitioned between ethyl acetate and saturated aqueous bicarbonate. The phases were separated and the organic layer was washed with water and brine, dried over magnesium sulfate and concentrated. The light yellow foam was recrystallized from ethanol to afford 0.195 g (61%) of (1R*,2R*)-1-(4-hydroxy-3-methoxyphenyl)-2-(4-hydroxy-4-phenyl-piperidin-1-yl)- propan-1-ol as a white solid which had: mp 187.5–188° C. Analysis calculated for $C_{21}H_{27}NO_4$: C, 70.56; H, 7.61; N, 3.92. Found: C, 70.44; H, 8.00; N, 3.78.

Example 22

(1R*,2R*)-1-(3,4-Dihydroxyphenyl)-2-(4-hydroxy-4-phenyl-piperidin-1-yl)-propan-1-ol A mixture of 2-bromo-1-(2,2-diphenyl-benzo(1,3)dioxol-5-yl)-propan-1-one (the compound of Preparation 43, 2.00 g, 4.89 mmol), 4-hydroxy-4-phenylpiperidine (0.90 g, 5.08 mmol) and triethylamine (1.40 mL, 10.04 mmol) in ethanol (50 mL) was refluxed overnight. The solvent was removed at reduced pressure and the residue was partitioned between ether and water. The phases were separated and the organic layer was washed with brine, dried over magnesium sulfate and concentrated. The residue was flash chromatographed on silica gel (2×5 inches packed with hexane) with elution proceeding as follows: 20% ethyl acetate/hexane (500 mL), unweighed forerun; 50% ethyl acetate/hexane (500 mL), 1.76 g (71%) of 1-(2,2-diphenyl-benzo(1,3)dioxol-5-yl)-2-(4hydroxy-4-phenylpiperidin-1-yl)-propan-1-one as light tan foam which was suitable for use without further purification and had: NMR δ7.81 (dd, J=1.7, 8.3 Hz, 1 H), 7.70 (d, J=1.6 Hz, 1 H), 7.64–7.13 (m, 15 H), 6.92 (d, J=8.2 Hz, 1 H), 4.07 (q, J=7.0 Hz, 1 H), 3.39–3.27 (m, 1 H), 2.94–2.59 (m, 3 H), 2.30–2.04 (m, 2 H), 1.74 (br t, J=13.2 Hz, 2 H), 1.30 (d, J=6.8 Hz, 3 H).

A mixture of sodium borohydride (0.15 g, 3.97 mmol) and ethanol (5 mL) was stirred 10 min and then 1-(2,2-diphenyl-benzo(1,3)dioxol-5-yl)-2-(4-hydroxy-4-phenylpiperidin-1-yl)-propan-1-one (1.70 g, 3.36 mmol in 20 mL of ethanol) was added. The reaction was stirred at ambient temperature over the weekend. The white precipitate was collected, rinsed with ethanol and ether, and air dried to afford 1.35 g of crude product. The product was recrystallized from ethanol/ether/hexane and then recrystallized from ethanol/ethyl acetate/methylene chloride to give 1.05 g (61%) of (1R*,2R*)-1-(2,2-diphenyl-benzo(1,3)dioxol-5-yl)-2-(4-hydroxy-4-phenylpiperidin- 1-yl)-propan-1-ol which had: mp 224–224.5° C. Analysis calculated for $C_{33}H_{33}NO_4$: C, 78.08; H, 6.55; N, 2.76. Found: C, 78.16; H, 6.46; N, 2.72.

A mixture of the product of the above reaction (1.00 g, 1.97 mmol) and 10% palladium on carbon (0.175 g) in methanol (50 mL) and acetic acid (1.0 mL) was hydrogenated at 50 psi (initial pressure) for 5 h at ambient temperature. Additional catalyst (0.18 g) was added and the hydrogenation was continued overnight. The reaction was filtered through diatomaceous earth and the filter pad was rinsed with methanol. The filtrate was concentrated and the residue was partitioned between ethyl acetate and saturated aqueous bicarbonate and stirred vigorously for 1 h. The phases were separated and the aqueous layer was extracted with ethyl acetate (2×). The combined organic layer was washed with water and brine, dried over magnesium sulfate and concentrated. The residue was flash chromatographed on silica gel (1×4 inches) with elution proceeding as follows: 20% ethyl acetate/hexane (500 mL), nil; 10% methanol/ethyl acetate (250 mL), 20% methanol/ethyl acetate (250 mL), and 50% methanol/ethyl acetate (250 mL), 0.51 g (75%) of a light yellow-green solid. The solid was recrystallized from ethanol to afford (1R*,2R*)-1-(3,4-dihydroxyphenyl)-2-(4-hydroxy-4-phenyl-piperidin-1-yl)-propan-1-ol as a white solid which had: mp 167–168° C. Analysis calculated for $C_{20}H_{25}NO_4 \cdot 0.5\ C_2H_6O$: C, 68.83; H, 7.70; N, 3.82. Found: C, 68.78; H, 8.05; N, 3.70.

Example 23

(1R*,2R*)-1-(3-Fluoro-4-hydroxyphenyl)-2-(4-hydroxy-4-phenylpiperidin-1-yl)-propan-1-ol mesylate A mixture of 3-fluoro-4-triisopropylsilyloxy-α-bromopropiophenone (2.0 g, 4.96 mmol), 4-hydroxy-4-phenylpiperidine (1.1 g, 6.2 mmol) and triethylamine (0.9 mL, 6.5 mmol) in ethanol (25 mL) was refluxed 6.5 h. The solvent was removed at reduced pressure and the residue was partitioned between ethyl acetate and water. The phases were separated and the organic layer was washed with brine, dried over magnesium sulfate and concentrated. The residue was flash chromatographed on silica gel (1×6 inches packed with hexane). The product was eluted with 15% ethyl acetate/hexane to afford 1.82 g (73%) of 1-(3-fluoro-4-triisopropylsilyloxyphenyl)-2-(4-hydroxy-4-phenylpiperidin-1-yl)-propan-1-one as a yellow oil which had: NMR δ7.91 (dd, J=2, 12 Hz, 1 H), 7.84 (dd, J=2.5, 8.5 Hz, 1 H), 7.51–7.47 (m, 2 H), 7.39–7.26 (m, 3 H), 6.98 (t, J=8.5 Hz, 1 H), 4.07 (q, J=7 Hz, 1 H), 2.92–2.84 (m, 2 H), 2.69–2.64 (m, 2 H), 2.23–1.95 (m, 2 H), 1.82–1.70 (m, 2 H), 1.38–1.22 (m, 6 H), 1.12 (d, J=7 Hz, 18 H).

A mixture of sodium borohydride (0.12 g, 3.17 mmol) and ethanol (5 mL) was stirred 10 min and then 1-(3-fluoro-4-triisopropylsilyloxyphenyl)-2-(4-hydroxy-4-phenylpiperidin-1-yl)-propan-1-one (1.41 g, 2.82 mmol in 25 mL of ethanol) was added. The reaction was stirred at ambient temperature overnight. The white precipitate which formed was collected by filtration to afford 0.14 g (10%) of (1R*,2R*)-1-(3-fluoro-4-triisopropylsilyloxyphenyl)-2-(4-hydroxy-4-phenylpiperidin-1-yl)-propan-1-ol which had: mp 140–141° C. Analysis calculated for $C_{29}H_{44}FNO_3Si$: C, 69.42; H, 8.84; N, 2.79. Found: C, 69.30; H, 9.06; N, 2.84. The filtrate was quenched with water and stirred overnight. The resulting precipitate was collected, washed with water and air dried (1.5 g). This material was recrystallized from ethanol to afford 0.72 g of additional product for a total yield of 0.86 g (61%).

The product of the above reaction (0.72 g, 1.43 mmol) was dissolved in tetrahydrofuran (10 mL) and tetrabutylammonium fluoride (1.45 mL, 1.45 mmol, 1 M tetrahydrofuran solution) was added. The reaction was stirred overnight at ambient temperature and then concentrated. Ether and water were added to the residue and after vigorous stirring, a white solid was collected and air dried to afford 0.5 g of the free base. This material was taken up in ethanol and methanesulfonic acid (0.093 mL, 1.43 mmol) was added. The mixture was concentrated and recrystallized from ethanol to afford 0.476 g (75%) of 1R*,2R* 1-(3-fluoro-4-hydroxyphenyl)-2-(4-hydroxy-4-phenylpiperidin-1-yl)-propan-1-ol mesylate which had: mp 198.5–199.5° C. Analysis calculated for $C_{20}H_{24}FNO_3 \cdot CH_4SO_3$: C, 57.13; H, 6.39; N, 3.17. Found: C, 57.02; H, 6.45; N, 3.33.

Example 24

(1R*2R*)-1-(3,5-Difluoro-4-hydroxyphenyl)-2-(4-hydroxy-4-phenylpiperidin-1-yl)-propan-1-ol mesylate A mixture of 3,5-difluoro-4-triisopropylsilyloxy-α-bromopropiophenone (2.46 g, 5.84 mmol), 4-hydroxy-4-phenylpiperidine (155 g, 8.74 mmol) and triethylamine (1.6 mL, 11.5 mmol) in ethanol (50 mL) was refluxed overnight. The solvent was removed at reduced pressure and the residue was partitioned between ethyl acetate and water. The phases were separated and the organic layer was washed with brine, dried over magnesium sulfate and concentrated. The residue was flash chromatographed on silica gel (1×5 inches packed with hexane) and eluted as follows: 10% ethyl acetate/hexane (250 mL), nil; 10% ethyl acetate/hexane (250 mL) and 20% ethyl acetate/hexane (250 mL), 1.41 g (47%) of 1-(3,5-difluoro-4-triisopropylsilyloxyphenyl)-2-(4-hydroxy-4-phenylpiperidin-1-yl)-propan-1-one as a orange oil which had: NMR δ7.73 (long range coupled d, J=9 Hz, 2 H), 7.46 (d, J=8.5 Hz, 1 H), 7.33 (t, J=7.5 Hz, 2 H), 7.27–7.21 (m, 1 H), 4.00 (q, J=6.7 Hz, 1 H), 2.91 (dt, J=2.5, 13 Hz, 1 H), 2.79–2.76 (m, 1 H), 2.69–2.60 (m, 2 H), 2.19–1.93 (m, 3 H), 1.80–1.67 (m, 3 H), 1.39–1.27 (m, 6 H), 1.10 (d, J=7 Hz, 18 H).

A mixture of sodium borohydride (0.16 g, 4.23 mmol) and ethanol (5 mL) was stirred 10 min and then 1-(3,5-difluoro-4-triisopropylsilyloxyphenyl)-2-(4-hydroxy-4-phenylpiperidin-1-yl)-propan-1-one (1.40 g, 2.86 mmol in 20 mL of ethanol) was added. The reaction was stirred at ambient temperature for 3 days. The reaction was quenched with water and stirred 4 h. The white precipitate which formed was collected by filtration and recrystallized from ethanol to afford 0.46 g (32%) of 1R*,2R* 1-(3,5-difluoro-4-triisopropylsilyloxyphenyl)-2-(4-hydroxy-4-phenylpiperidin-1-yl)-propan-1-ol which had: NMR δ7.54 (d, J=7.5 Hz, 2 H), 7.40 (t, J=7.5 Hz, J=8.5 Hz, 2 H), 7.31 (d, J=7 Hz, 1 H), 6.89 (d, J=9 Hz, 2 H), 5.28 (s, 1 H), 4.18 (d, J=9.5 Hz, 1 H), 3.10 (dt, J=2.2, 11.7 Hz, 1 H), 2.73–2.69 (m, 2 H), 2.62–2.51 (m, 2 H), 2.30–2.06 (m, 2 H), 1.90–1.83 (m, 2 H), 1.36–1.20 (m, 3 H), 1.10 (d, J=7 Hz, 18 H), 0.85 (d, J=6.7 Hz, 3 H). Analysis calculated for $C_{29}H_{43}F_2NO_3Si$: C, 67.02; H, 8.34; N, 2.69. Found: C, 66.77; H, 8.58; N, 2.71.

The product of the above reaction (0.398 g, 0.81 mmol) was dissolved in tetrahydrofuran (13 mL) and tetrabutylammonium fluoride (0.89 mL, 0.89 mmol, 1 M tetrahydrofuran solution) was added. The reaction was stirred 2 h at ambient temperature and then concentrated. A few drops of saturated aqueous ammonium chloride were added and the solvent was removed under a nitrogen stream. The residue was stirred with saturated aqueous bicarbonate and ethyl acetate and the white solid precipitate was collected and rinsed with water and ethyl acetate, then it was dried to afford 0.185 g of free base. The free base (0.150 g) was slurried in methanol and methanesulfonic acid (0.027 mL, 0.417 mmol) was added. The mixture was filtered, then concentrated at the boil to 0.5 mL with addition of ethyl acetate (2 mL). Cooling and trituration gave white crystals which were collected by filtration to afford 0.173 g, (91%) of 1R*,2R* 1-(3,5-difluoro-4-hydroxyphenyl)-2-(4-hydroxy-4-phenylpiperidin-1-yl)-propan-1-ol mesylate which had: mp 216–218° C. Analysis calculated for $C_{20}H_{23}F_2NO_3 \cdot CH_4SO_3$: C, 54.89; H, 5.92; N, 3.05. Found: C, 54.70; H, 5.90; N, 2.91.

Example 25

(1R*,2R*)-1-(3-Methyl-4-hydroxyphenyl)-2-(4-hydroxy-4-phenylpiperidin-1-yl)-propan-1-ol mesylate A mixture of 4-benzyloxy-3-methyl-α-bromopropiophenone (2.48 g, 7.45 mmol), 4-hydroxy-4-phenylpiperidine (1.1 g, 6.21 mmol), and triethylamine (2.08 mL, 14.9 mmol) in ethanol (17 mL) was refluxed 6 h. The solvent was removed at reduced pressure and the residue was partitioned between methylene chloride and water. The phases were separated and the organic layer was washed with brine, dried over magnesium sulfate and concentrated. The residue was flash chromatographed on silica gel (1×4 inches packed in 10% ethyl acetate/hexane) with elution proceeding as follows: 10% ethyl acetate/hexane (500 mL), nil; 20% ethyl acetate/hexane (250 mL), nil; 50% ethyl acetate/hexane (400 mL), 2.14 g of crude product. The product was recrystallized from ether/hexane to afford 1.41 g (53%) of 1-(4-benzyloxy-3-methylphenyl)-2-(4-hydroxy-4-phenylpiperidin-1-yl)-propan-1-one as a solid which had: mp 98–99° C.; NMR δ8.02 (dd, J=2, 8.5 Hz, 1 H), 7.97 (d, J=1.5 Hz, 1 H), 7.53–7.20 (m, 10 H), 6.92 (d, J=8.5 Hz, 1 H), 5.17 (s, 2 H), 4.14 (q, J=7 Hz, 1 H), 2.95–2.75 (m, 3 H), 2.64 (dt J=2.5, 12 Hz, 1 H), 2.33 (s, 3 H), 2.22–2.02 (m, 2 H), 1.82–1.70 (m, 2 H), 1.55 (br s, 1 H), 1.33 (d, J=7 Hz, 3 H).

A mixture of lithium aluminum hydride (0.246 g, 6.48 mmol) and tetrahydrofuran (45 mL) was chilled to 0° C. and 1-(4-benzyloxy-3-methylphenyl)-2-(4-hydroxy-4-phenylpiperidin-1-yl)-propan-1-one (1.39 g, 3.24 mmol) was added all at once as a solid. The reaction was allowed to warm to ambient temperature and stir overnight. The reaction was carefully quenched with water (0.467 mL) and stirred 4 h. The slurry was dried with sodium sulfate, filtered through diatomaceous earth and concentrated. The residue was flash chromatographed on silica gel (1×3 inches packed with 20% ethyl acetate/hexane) with elution proceeding as follows: 20% ethyl acetate/hexane (150 mL), nil; 30% ethyl acetate/hexane (250 mL) and 40% ethyl acetate/hexane (250 mL), 0.701 g (50%) of 1R*,2R* 1-(4-benzyloxy-3-methylphenyl)-2-(4-hydroxy-4-phenylpiperidin-1-yl)-propan-1-ol as a white solid which had: mp 162–163° C; NMR δ7.53–7.26 (m, 10 H), 7.17 (br d, 1 H), 7.11 (br d, J=8.5 Hz, 1 H), 6.83 (d, J=8.5 Hz, 2 H), 5.23 (s, 1 H), 5.07 (s, 2 H), 4.21 (d, J=9.5 Hz, 1 H), 3.08 (sym m, 1 H), 2.83–2.56 (m, 4 H), 2.28 (s, 3 H), 2.28–2.05 (m, 2 H), 1.84 (br d, J=13.5 Hz, 2 H), 1.54 (s, 1 H), 0.82 (d, J=6.5 Hz, 3 H).

The product of the above reaction (0.69 g, 1.6 mmol) was dissolved in tetrahydrofuran (30 mL) and methanol (30 mL) and ammonium formate (1.0 g, 16 mmol, and 10% palladium on carbon (0.15 g) were added. The reaction was stirred 2 h at ambient temperature and then filtered through diatomaceous earth. The filter pad was rinsed with ethanol and water. The filtrate was concentrated and the residue was stirred with ethyl acetate and saturated aqueous bicarbonate. The solid precipitate was collected, rinsed with ether and air dried to afford 0.611 g (100%) of 1R*,2R* 1-(4-hydroxy-3-methylphenyl)-2-(4-hydroxy-4-phenylpiperidin-1-yl)-propan-1-ol as a white solid. The solid was chromatographed on silica gel (1×3 inches packed with 50% ethyl acetate/hexane) with gradient elution from 50% ethyl acetate/hexane to 2% methanol/ethyl acetate. Product fractions were combined, concentrated and recrystallized from nitromethane to afford 0.063 g (11.5%) of pure free base product. Anal calculated for $C_{21}H_{27}NO_3$: C, 73.87; H, 7.97; N, 4.10. Found: C, 73.60; H, 8.21; N, 4.22. This product was converted to its mesylate salt. It was slurried in methanol (a few drops) and methanesulfonic acid (0.010 mL, 0.152 mmol) was added. The mixture was diluted with isopropanol (1 mL) and concentrated to about 0.25 mL at the boil. The crystals which formed upon cooling were collected to give the mesylate salt as a crystalline white solid (0.053 g) which had: mp 196–197° C.

Example 26

(1R*,2R*)-1-(3,5-Dimethyl-4-hydroxyphenyl)-2-(4-hydroxy-4-phenylpiperidin-1-yl)-propan-1-ol mesylate A mixture of 4-benzyloxy-3,5-dimethyl-α-bromopropiophenone (2.59 g, 7.45 mmol), 4-hydroxy-4-phenylpiperidine (1.1 g, 6.21 mmol), and triethylamine (2.08 mL, 14.9 mmol) in ethanol (15 mL) was refluxed 6 h. The solvent was removed at reduced pressure and the residue was partitioned between methylene chloride and water. The phases were separated and the organic layer was washed with brine, dried over magnesium sulfate and concentrated. The residue was flash chromatographed on silica gel (1.5×3.5 inches packed in 10% ethyl acetate/hexane) with elution proceeding as follows: 10% ethyl acetate/hexane (500 mL), nil; 20% ethyl acetate/hexane (250 mL), nil; 50% ethyl acetate/hexane (400 mL), 2.16 g (79%) of 1-(4-benzyloxy-3,5-dimethylphenyl)-2-(4-hydroxy-4-phenylpiperidin-1-yl)-propan-1-one as an orange foam which had: NMR δ7.82 (s, 2 H), 7.55–7.21 (m, 10 H), 4.87 (s, 2 H), 4.17 (q, J=7 Hz, 1 H), 2.93–2.78 (m, 3 H), 2.66 (dt J=3, 12 Hz, 1 H), 2.35 (s, 6 H), 2.26–2.04 (m, 2 H), 1.95–1.69 (m, 3 H), 1.34 (d, J=7 Hz, 3 H). The material had about 15% of an unidentified impurity but was suitable for use without further purification.

A mixture of lithium aluminum hydride (0.257 g, 6.77 mmol) and tetrahydrofuran (45 mL) was chilled to 0° C. and 1-(4-benzyloxy-3,5-dimethylphenyl)-2-(4-hydroxy-4-phenylpiperidin-1-yl)-propan-1-one (1.50 g, 3.38 mmol) was added all at once. The reaction was allowed to warm to ambient temperature and stir overnight. The reaction was carefully quenched with water (0.487 mL) and stirred 4 h. The slurry was dried with sodium sulfate, filtered through diatomaceous earth and concentrated. The residue was flash chromatographed on silica gel (1×3 inches packed with a mixture of 20% ethyl acetate/hexane) with elution proceeding as follows: 20% ethyl acetate/hexane (100 mL), nil; 20% ethyl acetate/hexane (100 mL) and 30% ethyl acetate/hexane (250 mL), 1.32 g (66%) of 1R*,2R* 1-(4-benzyloxy-3,5-dimethylphenyl)-2-(4-hydroxy-4-phenylpiperidin-1-yl)-propan-1-ol as a yellow solid which had: mp 133–135° C.; NMR δ7.54–7.48 (m, 4 H), 7.47–7.25 (m, 6 H), 7.02 (s, 2 H), 5.23 (s, 1 H), 4.79 (s, 2 H), 4.19 (d, J=9.5 Hz, 1 H), 3.09 (sym m, 1 H), 2.81–2.59 (m, 4 H), 2.29 (s, 6 H), 2.30–2.25 (m, 2 H), 1.85 (br d, J=13.5 Hz, 2 H), 1.54 (s, 1 H), 0.84 (d, J=6.5 Hz, 3 H).

The product of the above reaction (1.30 g, 2.92 mmol) was dissolved in tetrahydrofuran (50 mL) and methanol (50 mL) and ammonium formate (1.8 g, 29 mmol, and 10% palladium on carbon (0.3 g) were added. The reaction was stirred 2 h at ambient temperature and then filtered through diatomaceous earth. The filter pad was rinsed with ethanol and water. The filtrate was concentrated and the residue was partitioned between chloroform, saturated aqueous bicarbonate and a small amount of acetone. The phases were separated and the organic layer was washed with brine, dried and concentrated to afford 0.886 g (86%) of 1R*,2R* 1-(3,5-dimethyl-4-hydroxyphenyl)-2-(4-hydroxy-4-phenylpiperidin-1-yl)-propan-1-ol as a white solid. This product was converted to its mesylate salt. It was slurried in methanol (a few mL) and methanesulfonic acid (0.163 mL, 2.52 mmol) was added. The mixture was concentrated and the residue was triturated with ether. The remaining solid was recrystallized from isopropanol to afford 0.273 g (24%) of the mesylate salt which had: mp 203–204° C. Anal calculated for $C_{22}H_{29}NO_3 \cdot CH_4SO_3 \cdot 0.5\ H_2O$: C, 59.98; H, 7.44; N, 3.04. Found: C, 60.10; H, 7.63; N, 3.13.

Example 27

(1R,2R)-1-(4-Hydroxy-3-methoxyphenyl)-2-(4-hydroxy-4-phenyl-piperidin-1-yl)-propan-1-ol and (1S,2S)-1-(4-Hydroxy-3-methoxyphenyl)-2-(4-hydroxy-4-phenyl-piperidin-1-yl)-propan-1-ol The product of Example 21 was dissolved in ethanol and separated into its enantiomers by HPLC using the following chromatographic conditions: Column, Chiralcel OD; mobile phase, 25% ethanol/75% hexane; temperature, ambient (approximately 22° C.); detection, UV at 215 nM. Under these conditions, (1R,2R)-1-(4-hydroxy-3-methoxyphenyl)-2-(4-hydroxy-4-phenyl-piperidin-1-yl)-propan-1-ol eluted with a retention time of approximately 9.12 min and (1S, 2S)-1-(4-hydroxy-3-methoxyphenyl)-2-(4-hydroxy-4-phenyl-piperidin-1-yl)-propan-1-ol eluted with a retention time of approximately 16.26 min.

Preparation 1
4-Propionyl-2-methylphenol

A mixture of 2-methylphenol (10.48 g, 96.91 mmol), propionic acid (5.23 mL, 97.88 mmol) and trifluoromethanesulfonic acid (50 g) was heated at 80° C. for 30 h. The reaction was cooled, poured onto ice, and extracted with chloroform. The organic phase was separated and washed with aqueous bicarbonate and brine; then it was dried, filtered, and concentrated to a brown solid. This residue was distilled at 1.5 mm Hg to afford two fractions: 25–150° C. (forerun, discarded); 160° C. (5.58 g, 35%) of 4-propionyl-2-methylphenol as a white crystalline solid which had: mp 83–85° C.; NMR δ7.81 (d, J=1.5 Hz, 1 H), 7.76 (dd, J=2, 8.5 Hz, 1 H), 6.88 (d, J=8.5 Hz, 1 H), 6.61 (s, 1 H), 2.98 (q, J=7.5 Hz, 2 H), 2.30 (s, 3 H), 1.22 (t, J=7.5 Hz, 3 H).

Preparation 2
4-Propionyl-2-methylphenol

To a mixture of aluminum chloride (51.8 g, 0.388 mol) and methylene chloride (140 mL) was added propionyl chloride (11.25 mL, 0.129 mol) followed by 2-methylphenol (7.0 g, 64.73 mmol in methylene chloride (25 mL with a 10 mL rinse)). The mixture was stirred 2 h at ambient temperature and then poured onto ice. The phases were separated and the organic phase was washed with aqueous bicarbonate and brine. The organic phase was dried over calcium sulfate and concentrated onto silica gel. The material was flash chromatographed on silica gel (3.5×3 inches) with elution proceeding as follows: hexane (200 mL), nil; 4% ethyl acetate/hexane (1000 mL), nil; 8% ethyl acetate/hexane (2000 mL), 8.17 g of 4-propionyl-2-methylphenyl propionate as a light yellow oil which had: NMR δ7.86 (s, 1 H), 7.82 (dd, J=2, 8.5 Hz, 1 H), 2.98 (q, J=7 Hz, 2 H), 2.65 (q, J=7.5 Hz, 2 H), 2.23 (s, 3 H), 1.30 (t, J=7.5 Hz, 3 H), 1.22 (t, J=7.5 Hz, 3 H).

The product from the above reaction (7.61 g, 34.57 mmol) was added to a mixture of methanol (100 mL), water (100 mL) and potassium hydroxide (3.88 g, 68.14 mmol) and refluxed for 1.5 h. The methanol was removed at reduced pressure and the residue was acidified with 6N HCl. The aqueous phase was extracted with ethyl acetate. This organic layer was washed with aqueous bicarbonate and brine; then it was dried and concentrated to yield 5.29 g (93%) of 4-propionyl-2-methylphenol as a white crystalline solid which was identical to the material prepared in Preparation 1.

Preparation 3
4-Triisopropylsilyloxy-3-methylpropiophenone

To a mixture of 4-propionyl-2-methylphenol (the compound of Preparations 1 and 2, 5.19 g, 31.63 mmol) and imidazole (4.31 g, 63.26 mmol) in dimethylformamide (35 mL) was added triisopropylsilyl chloride (7.44 mL, 34.79 mmol in 15 mL of dimethylformamide with a 2 mL rinse). The reaction was stirred at ambient temperature for 15 h; then poured onto a mixture of ice and 1N aqueous lithium chloride. The mixture was extracted with ethyl acetate (3×). The combined organic phase was washed with 1N lithium chloride and brine, dried over calcium sulfate and concentrated to afford 9.61 g (95%) of 4-triisopropylsilyloxy-3- methylpropiophenone as a yellow oil which contained a small silyl impurity by NMR but which was suitable for use without further purification. The product had NMR δ7.80 (d, J=2 Hz, 1 H), 7.71 (dd, J=2.5, 8.5 Hz, 1 H), 6.80 (d, J=8.5 Hz, 1 H), 2.94 (q, J=7.5 Hz, 2 H), 2.28 (s, 3 H), 1.33 (sym m, 3 H), 1.20 (t, J=7.5 Hz, 3 H), 1.12 (d, J=7 Hz, 18 H).

Preparation 4
4-Benzyloxy-3-methylpropiophenone

A mixture of benzyl bromide (4.44 mL, 37.34 mmol), potassium carbonate (9.38 g, 67.88 mmol) and 4-propionyl-2-methylphenol (the compound of Preparations 1 and 2, 5.57 g, 33.94 mmol) in acetone (100 mL) was stirred at ambient temperature for 24 h. The solvent was removed at reduced pressure and the residue was partitioned between water and methylene chloride. The phases were separated and the organic phase was washed with brine, dried over calcium sulfate and concentrated. This residue was flash chromatographed on silica gel (2×4 inches) with elution proceeding as follows: 5% ethyl acetate/hexane (300 mL), discarded forerun; 5% ethyl acetate/hexane (500 mL) and 10% ethyl acetate/hexane (600 mL), 8.03 g (93%) of 4-benzyloxy-3-methylpropiophenone as a white crystalline solid which had: NMR δ7.83–7.78 (m, 2 H), 7.48–7.31 (m, 5 H), 6.89 (d, J=9 Hz, 1 H), 5.14 (s, 2 H), 2.94 (q, J=7.5 Hz, 2 H), 2.31 (s, 3 H), 1.20 (t, J=7.5 Hz, 3 H). This material was suitable for use without further purification.

Preparation 5
4-Benzyloxy-3-methyl-α-bromopropiophenone

To a mixture of 4-benzyloxy-3-methylpropiophenone (the compound of Preparation 4, 7.89 g, 31.06 mmol) in carbon tetrachloride (80 mL) was added bromine (1.63 mL, 31.68 mmol in 20 mL of carbon tetrachloride with a 5 mL rinse) dropwise with the bromine color nearly dissipating on contact with the reaction solution. The reaction was stirred 15 min at ambient temperature and then aqueous sodium bisulfite was added. The mixture was stirred 30 min more. The phases were separated and the organic layer was washed with aqueous bicarbonate and brine. The organic layer was dried over calcium sulfate and concentrated to yield 10.29 g (99.5%) of the title product as a light tan solid which had: mp 88.5–89.5° C. and was suitable for use without further purification.

Preparation 6
4-Triisopropylsilyloxy-3-methyl-α-bromopropiophenone

To a solution of 4-triisopropylsilyloxy-3-methylpropiophenone (the compound of Preparation 3, 9.35 g, 29.19 mmol) in carbon tetrachloride (100 mL) was added bromine (1.53 mL, 29.77 mmol in 20 mL of carbon tetrachloride) dropwise with the bromine color dissipating almost on contact with the reaction solution. The reaction was stirred 15 min; then aqueous bisulfite was added and the mixture was stirred 15 min more. The phases were separated and the organic layer was washed with aqueous bicarbonate and brine. The organic layer was dried over calcium sulfate and concentrated to afford 11.65 g (100%) of 4-triisopropylsilyloxy-3-methyl-α-bromopropiophenone as a light yellow oil which had: NMR δ7.86 (d, J=2 Hz, 1 H), 7.78 (dd, J=2.5, 8.5 Hz, 1 H), 6.82 (d, J=8.5 Hz, 1 H), 5.27 (q, J=6.5 Hz, 1 H), 2.29 (s, 3 H), 1.88 (d, J=6.5 Hz, 3 H), 1.42–1.27 (m, 3 H), 1.13 (d, J=7 Hz, 18 H). This material was suitable for use without further purification.

Preparation 7
4-Propionyl-2-fluorophenol

To a mixture of aluminum chloride (45.8 g, 0.343 mol) in methylene chloride (140 mL) was added propionyl chloride (10.85 mL, 124.9 mmol) all at once followed by 2-fluorophenol (5.57 mL, 62.44 mmol in 25 mL of methylene chloride with a 10 mL rinse). The mixture was gently refluxed 5 h, cooled to ambient temperature and poured onto ice. The phases were separated and the aqueous layer was extracted with methylene chloride. The combined organic layer was washed with aqueous bicarbonate and brine. The organic layer was dried over calcium sulfate and concentrated to give 11.43 g (82%) of 4-propionyl-2-fluorophenyl propionate as a clear tan oil which was used without characterization.

The product of the above reaction (10.76 g, 48.01 mmol) was added to a mixture of methanol (125 mL), water (125 mL) and potassium hydroxide (5.39 g, 56.11 mmol). The reaction was refluxed 2 h, cooled and the methanol was removed at reduced pressure. The residue was acidified with 6 N HCl and extracted with ethyl acetate. The organic phase was washed with aqueous bicarbonate and brine, dried over calcium sulfate and concentrated to a tan solid. This tan residue was flash chromatographed on silica gel (2×3 inches packed in hexane) with elution proceeding as follows: 5% ethyl acetate/hexane (800 mL), discarded forerun; 10% ethyl acetate/hexane (500 mL), nil; 25% ethyl acetate/hexane (1000 mL), 5.56 g (69%) of 4-propionyl-2-fluorophenol as a white solid which had: mp 104–106° C.; NMR δ7.74 (dd, J=2, 9.5 Hz, 1 H), 7.71–7.68 (m, 1 h), 7.05 (t, J=8.5 Hz, 1 H), 5.82 (br s, 1 H), 2.93 (q, J=7.5 Hz, 2 H), 1.20 (t, J=7 Hz, 3 H).

Preparation 8
4-Propionyl-2-fluorophenol

A mixture of 4-bromo-2-fluorophenol (1.0 g, 5.24 mmol) in tetrahydrofuran (15 mL) was chilled to −78° C. and butyllithium (4.6 mL, 11.5 mmol, 2.5 M solution) was added rapidly, dropwise. The reaction was stirred 12 min and N-methyl-N-methoxypropionamide (the compound of Preparation 9, 0.735 g, 6.28 mmol in 1 mL of tetrahydrofuran with a 1 mL rinse) was added. The reaction was allowed to stir 5 min at −78° C. and then it was warmed to ambient temperature. A few drops of water were added; then the solvent was removed at reduced pressure. The residue was taken up in methylene chloride and washed with aqueous ammonium chloride and brine. The organic layer was dried and concentrated. The residue was flash chromatographed on silica gel (1×2.5 inches packed in hexane) with elution proceeding as follows: 10% ethyl acetate/hexane (250 mL), discarded forerun; 20% ethyl acetate/hexane (250 mL), 0.186 g of a yellow crystalline solid which had NMR identical to that of preparation 7.

Preparation 9
N-Methyl-N-methoxypropionamide

A mixture of N,O-dimethyl hydroxylamine hydrochloride (4.43 g, 45.39 mmol) and triethylamine (6.93 mL, 49.71 mmol) in methylene chloride (150 mL) was chilled to 0° C. and propionyl chloride (3.76 mL, 43.23 mmol in 25 mL of methylene chloride with a 25 mL rinse) was added dropwise. The mixture was allowed to warm to ambient temperature and stir over the weekend. The reaction was extracted with water and brine, dried, and concentrated to afford 3.08 g (61%) of N-methyl-N-methoxypropionamide as a yellow oil which had: NMR δ3.66 (s, 3 H), 3.16 (s, 3 H), 2.42 (q, J=7.5 Hz, 2 H), 1.12 (t, J=7.5 Hz, 3 H). This material was suitable for use without further purification.

Preparation 10
4-Triisopropylsilyloxy-3-fluoropropiophenone

A mixture of 4-propionyl-2-fluorophenol (the compound of Preparation 7, 5.44 g, 32.37 mmol), imidazole (4.41 g, 64.74 mmol), and triisopropylsilyl chloride (7.62 mL, 35.60 mmol) in dimethylformamide (55 mL) was stirred 15 h at ambient temperature. The reaction poured onto a mixture of ice and 1N aqueous lithium chloride. The mixture was extracted with ethyl acetate (3x). The combined organic phase was washed with 1N lithium chloride and brine, dried over calcium sulfate and concentrated to afford 10.5 g (100%) of 4-triisopropylsilyloxy-3-fluoropropiophenone as a yellow oil which had: NMR δ7.75–7.60 (m, 2 H), 6.95 (t, J=8 Hz, 1 H), 2.92 (q, J=7 Hz, 2 H), 1.25 (sym m, 3 H), 1.19 (t, J=7.5 Hz, 3 H), 1.09 (d, J=7 Hz, 18 H). The material was suitable for use without further purification.

Preparation 11
4-Triisopropylsilyloxy-3-fluoro-α-bromopropiophenone

To a solution of 4-triisopropylsilyloxy-3-fluoropropiophenone (the compound of Preparation 10, 10.27 g, 31.67 mmol) in carbon tetrachloride (110 mL) was added bromine (1.66 mL, 32.3 mmol in 20 mL of carbon tetrachloride) dropwise. (Note that after the first few drops of bromine solution were added, the bromine color did not dissipate. To initiate the reaction one drop of 48% HBr was added and the mixture was stirred 5 min until the color dissipated. Then the rest of the bromine solution was added dropwise.) The mixture was stirred 15 min; then aqueous bisulfite was added and the reaction was stirred 15 min more. The phases were separated and the organic layer was washed with aqueous bicarbonate and brine. The organic layer was dried over calcium sulfate and concentrated to yield 11.68 g (91%) of 4-triisopropylsilyloxy-3-fluoro-α-bromopropiophenone as a yellow oil which had: NMR δ7.80–7.69 (m, 2 H), 6.99 t, J=8.5 Hz, 1 H), 5.20 (q, J=6.5 Hz, 1 H), 1.89 (d, J=6.5 Hz, 3 H), 1.28 (sym m, 3 H), 1.12 (d, J=7 Hz, 18 H). This product was suitable for use without further purification.

Preparation 12
2,6-Dichloro-4-propionylphenol

A mixture of 2,6-dichlorophenol (10.10 g, 61.96 mmol) and propionic acid (3.34 mL, 62.58 mmol) in trifluoromethanesulfonic acid (50 g) was heated to 80° C. for 24 h. The reaction was cooled to ambient temperature, poured onto ice and extracted with chloroform (3x). The combined organic layer was washed with aqueous bicarbonate and brine, dried, and concentrated to give 8.90 g (66%) of 2,6-dichloro-4-propionylphenol as a tan solid which had: mp 50–52° C.; NMR δ7.89 (s, 2 H), 6.29 (s, 1 H), 2.91 (q, J=7 Hz, 2 H), 1.20 (t, J=7 Hz, 3 H). This material was used without further purification.

Preparation 13
3,5-Dichloro-4-triisopropylsilyloxypropiophenone

A mixture of 2,6-dichloro-4-propionylphenol (the compound of Preparation 12, 8.67 g, 39.59 mmol), imidazole (5.39 g, 79.18 mmol), and triisopropylsilyl chloride (9.32 mL, 43.56 mmol) in dimethylformamide (90 mL) was stirred 15 h at ambient temperature. The reaction poured onto a mixture of ice and 1N aqueous lithium chloride. The mixture was extracted with ethyl acetate (3x). The combined organic phase was washed with 1N lithium chloride and brine, dried over calcium sulfate and concentrated. The residue was flash chromatographed on silica gel (3×3 inches packed in hexane) with elution proceeding as follows: hexane (200 mL), nil; 2% ethyl acetate/hexane (400 mL), nil; 5% ethyl acetate/hexane (400 mL), nil; 5% ethyl acetate/hexane (500 mL) and 8% ethyl acetate/hexane (200 mL), 5.72 g of white solid. This material was Kugelrohr distilled at 1.5 mm Hg and the following fractions were collected: 70° C. (pot temperature), discarded forerun; 130° C., discarded forerun; 150–170° C., 3.84 g (26%) of 3,5-dichloro-4-triisopropylsilyloxypropiophenone as a white solid which contained a small impurity by NMR but was suitable for use without further purification. A sample which was kugelrohr distilled again had: mp 74–76° C.; NMR δ7.88 (s, 2 H), 2.92 (q, J=7 Hz, 2 H), 1.45 (sym m, 3 H), 1.21 (t, J=7 Hz, 3 H), 1.14 (d, J=7.5 Hz, 18 H).

Preparation 14
3,5-Dichloro-4-triisopropylsilyloxy-α-bromopropiophenone

To a solution of 3,5-dichloro-4-triisopropylsilyloxypropiophenone (the compound of Preparation 13, 3.84 g, 10.23 mmol) in carbon tetrachloride (45 mL) was added bromine (0.54 mL, 10.48 mmol in 5 mL of carbon tetrachloride) dropwise. After the first few drops of bromine solution were added, addition was stopped until the reaction initiated as indicated by disappearance of the red color of the solution. Then addition of bromine solution was resumed (total addition time was 20 min). The reaction was stirred 1 h, then aqueous bisulfite was added and the mixture was stirred 1.5 h more. The layers were separated and the organic phase was washed with aqueous bicarbonate and brine. The organic layer was dried over magnesium sulfate and concentrated to afford 4.88 g (100%) of 3,5-dichloro-4-triisopropylsilyloxy-α-bromopropiophenone as a pale yellow oil which had: NMR δ7.95 (s, 2 H), 5.15 (q, J=6.7 Hz, 1 H), 1.89 (d, J=6.7 Hz, 3 H), 1.53–1.42 (m, 3 H), 1.15 (d, J=7.4 Hz, 18 H). The NMR spectrum also indicated some minor impurities were present but the product was found suitable for use without further purification.

Preparation 15
2,6-Dimethyl-4-propionylphenol

To a mixture of aluminum chloride (32.0 g, 24 mmol) in methylene chloride (100 mL) was added propionyl chloride (3.56 mL, 40.95 mmol) all at once followed by 2,6-dimethylphenol (5.0 g, 40.93 mmol in 25 mL of methylene chloride) over 5 min. After stirring 1 h at ambient temperature a second equivalent of propionyl chloride was added (3.56 mL). The reaction was stirred 2 h more and then carefully quenched with water. The mixture was extracted with ether (3x) and the combined organic phase was washed with aqueous bicarbonate and brine; then it was dried over magnesium sulfate and concentrated to give 8.18 g (85%) of 2,6-dimethyl-4-propionylphenyl propionate as a waxy tan solid which had: NMR δ7.68 (s, 2 H), 2.95 (q, J=7.3 Hz, 2 H), 2.65 (q, J=7.5 Hz, 2 H), 2.19 (s, 6 H), 1.32 (t, J=7.6 Hz, 3 H), 1.20 (t, J=7.3 Hz, 3 H). This product also contained some minor impurities in the NMR spectrum but was found suitable for use without further purification.

The product from the above reaction (8.18 g, 34.91 mmol) was added to mixture of methanol (100 mL), water (100 mL) and potassium hydroxide (3.9 g, 69.5 mmol) and the reaction was refluxed 1 h. The methanol was removed at reduced pressure and the residue was acidified to pH 4 with 6 N HCl. This aqueous phase was extracted with ether. The organic layer was washed with aqueous bicarbonate (2x), dried over magnesium sulfate and concentrated to give 5.4 g (87%) of 2,6-dimethyl-4-propionylphenol as a waxy tan solid which had: NMR δ7.65 (s, 2 H), 5.47 (s, 1 H), 2.94 (q, J=7.3 Hz, 2 H), 2.30 (s, 6 H), 1.21 (t, J=7.3 Hz, 3 H).

Preparation 16
2,6-Dimethyl-4-propionylphenol

A mixture of 2,6-dimethylphenol (10.5 g, 85.95 mmol), propionic acid (4.64 mL, 86.81 mmol), and trifluoromethanesulfonic acid (59 g) was heated to 80° C. for 48 h, then poured onto ice. The mixture was extracted with chloroform and this organic phase was washed with aqueous bicarbonate and brine. The organic layer was dried and concentrated to a dark orange oily solid. The residue was kugelrohr distilled at 1.5 mm Hg and the following fractions were collected: 23–105° C. (pot temperature), discarded forerun; 105–135° C., 11.2 g (73%) of 2,6-dimethyl-4-propionylphenol as a yellow-white solid which had NMR identical to that of preparation 15.

Preparation 17
3,5-Dimethyl-4-triisopropylsilyloxypropiophenone

A mixture of 2,6-dimethyl-4-propionylphenol (the compound of Preparations 15 and 16, 3.0 g, 16.83 mmol), imidazole (2.3 g, 33.8 mmol), and triisopropylsilyl chloride (4.0 mL, 18.7 mmol) in dimethylformamide (30 mL) was stirred at ambient temperature overnight. The reaction was poured onto ice and extracted with ether. The organic phase was washed with 1N lithium chloride (2x), water, and brine; then it was dried over magnesium sulfate and concentrated to give a 5.62 g (100%) of 3,5-dimethyl-4-triisopropylsilyloxypropiophenone as a yellow solid which had: mp 87–88.5° C.; NMR δ7.62 (s, 2 H), 2.94 (q, J=7.2 Hz, 2 H), 2.30 (s, 6 H), 1.37–1.28 (m, 3 H), 1.20 (t, J=7.2 Hz, 3 H), 1.12 (d, J=7.1 Hz, 18 H).

Preparation 18
3,5-Dimethyl-4-triisopropylsilyloxy-α-bromopropiophenone

To a solution of 3,5-dimethyl-4-triisopropylsilyloxypropiophenone (the compound of Preparation 17, 5.50 g, 16.44 mmol) in carbon tetrachloride (60 mL) was added bromine (0.87 g, 16.89 mmol in 15 ml of carbon tetrachloride) dropwise. After the first few drops of bromine solution were added, addition was stopped until the reaction initiated as indicated by disappearance of the red color of the solution. Then addition of bromine solution was resumed (total addition time was 20 min). The reaction was stirred 30 min, then aqueous bisulfite was added and the mixture was stirred 1 h more. The layers were separated and the organic phase was washed with aqueous bicarbonate and brine. The organic layer was dried over magnesium sulfate and concentrated to afford 7.0 g (100%) of 3,5-dimethyl-4-triisopropylsilyloxy-α-bromopropiophenone as a orange solid which had: NMR δ7.68 (s, 2 H), 5.28 (q, J=6.6 Hz, 1 H), 2.31 (s, 6 H), 1.88 (d, J=6.6 Hz, 3 H), 1.38–1.27 (m, 3 H), 1.13 (d, J=7.2 Hz, 18 H); $^{13}$C NMR δ192.66, 158.87, 132.77, 130.18, 128.61, 126.88, 41.52, 20.40, 18.07, 17.94, 17.70, 14.26, 12.29.

Preparation 19
3,5-Difluoro-4-triisopropylsilyloxypropiophenone

A mixture of 2,6-difluoro-4-propionylphenol (Indofine Chemicals Company, Inc., P.O. Box 473, Somerville, N.J., 08876, U.S.A., 1.69 g, 9.08 mmol), imidazole (1.24 g, 18.2 mmol), and triisopropylsilyl chloride (2.14 mL, 10.0 mmol) in dimethylformamide (20 mL) was stirred at ambient temperature overnight. The mixture was poured into water and extracted with ether (3x). The combined organic layer was washed with 1N lithium chloride (2x), water, and brine; then it was dried over magnesium sulfate and concentrated to yield 3.06 g (98%) of 3,5-difluoro-4-triisopropylsilyloxypropiophenone as a light tan oil which had: NMR δ7.51 (long range coupled d, J=8.5 Hz, 2 H), 2.92 (q, J=7.2 Hz, 2 H), 1.35–1.19 (m, 6 H), 1.10 (d, J=7.1 Hz, 18 H).

Preparation 20
3,5-Difluoro-4-triisopropylsilyloxy-α-bromopropiophenone

To a mixture of 3,5-difluoro-4-triisopropylsilyloxypropiophenone (the compound of Preparation 19, 3.0 g, 8.76 mmol) in carbon tetrachloride (35 mL) was added bromine (0.46 mL, 8.93 mmol in 5 mL of carbon tetrachloride) dropwise. After the first few drops of bromine solution were added, the addition was stopped waiting for the bromination to initiate. After 5 min, 1 drop of 48% HBr was added. When the bromine color did not dissipate after 5 min more, the mixture was heated to about 50° C. After 10 min, the reaction initiated and the remaining bromine solution was added dropwise (20 min). The reaction was stirred 15 min and then aqueous bisulfite was added followed by stirring 30 min more. The phases were separated and the organic layer was washed with water, aqueous bicarbonate and brine. The organic layer was dried over calcium sulfate and concentrated to afford 3.26 g (88%) of 3,5-difluoro-4-triisopropylsilyloxy-α-bromopropiophenone as a white solid which had: NMR δ7.58 (long range coupled dd, J=1.3, 7.3 Hz, 2 H), 5.14 (q, J=6.7 Hz, 1 H), 1.89 (d, J=6.5 Hz, 3 H), 1.36–1.20 (m, 3 H), 1.11 (d, J=7.4 Hz, 18 H); $^{13}$C NMR δ190.50, 156.16, 156.09, 152.88, 152.81, 125.99, 113.05, 112.91, 112.82, 112.71, 40.75, 20.05, 17.16, 12.90.

Preparation 21
3,5-Difluoro-4-benzyloxypropiophenone

A mixture of 2,6-difluoro-4-propionylphenol (Indofine Chemicals Company, Inc., P.O. Box 473, Somerville, N.J., 08876, U.S.A., 2.5 g, 13.43 mmol), potassium carbonate (3.7 g, 26.8 mmol), and benzyl bromide (1.75 mL, 14.71 mmol) in acetone (40 mL) was stirred at ambient temperature overnight. The mixture was concentrated at reduced pressure and the residue was partitioned between ether and water. The phases were separated and the organic phase was washed with water and brine, dried over magnesium sulfate, and concentrated to an oily solid. This residue was triturated with hexane to afford 1.40 g of product. The mother liquors were flash chromatographed on silica gel (1×4 inches) with elution proceeding as follows: hexane (200 mL), unweighed benzyl bromide; 20% ethyl acetate/hexane (150 mL), 0.38 g of product. In this fashion 1.78 g (48%) of 3,5-difluoro-4-benzyloxypropiophenone was obtained as a white solid which had: NMR δ7.56–7.32 (m, 7 H), 5.30 (s, 2 H), 2.91 (q, J=7.2 Hz, 2 H), 1.21 (t, J=7.1 Hz, 3 H).

Preparation 22
3,5-Difluoro-4-benzyloxy-α-bromopropiophenone

To a solution of 3,5-difluoro-4-benzyloxypropiophenone (the compound of Preparation 21, 1.78 g, 6.44 mmol) in carbon tetrachloride (25 mL) was added bromine (0.34 mL, 6.60 mmol in 5 mL of carbon tetrachloride) dropwise. After the first few drops of bromine solution were added, addition was stopped until the reaction initiated as indicated by disappearance of the red color of the solution. Then addition of bromine solution was resumed (total addition time was 15 min). The reaction was stirred 1 h, then concentrated under a stream of nitrogen. The residue was taken up in ether and washed with aqueous bisulfite, aqueous bicarbonate, and brine; then it was dried and concentrated to afford 2.16 g (94%) of 3,5-difluoro-4-benzyloxy-α-bromopropiophenone as a straw colored oil which had: NMR δ7.58 (d, J=9 Hz, 2 H), 7.47–7.32 (m, 5 H), 5.33 (s, 2 H), 5.11 (q, J=6.6 Hz, 1 H), 1.88 (d, J=6.6 Hz, 3 H). There was also a small amount of starting material observed in the NMR spectrum but the product was found to be suitable for further reaction without additional purification.

Preparation 23
2-Acetoxy-2,6-dimethyl-3,4,5,6-cyclohexadien-1-one

To a slurry of lead tetraacetate (20.0 g, 45.1 mmol) in acetic acid (33 mL) was added 2,6-dimethylphenol (5.00 g, 40.93 mmol in 27 mL of acetic acid) dropwise over 15 min. The reaction was stirred at ambient temperature 2 h and gradually turned homogeneous yellow. The mixture was diluted with water and extracted with chloroform (3x). The combined organic layer was washed with water and brine, dried over calcium sulfate, and concentrated to a yellow oil. The residue was kugelrohr distilled at 0.4 mm Hg. The material which distilled from a pot temperature of 75–85° C. (5.69 g) was collected as a yellow oil. A 3.2 g sample was further purified by flash chromatography on silica gel (1×5 inches) with elution proceeding as follows: hexane (500 mL), nil; 5% ether/hexane (500 mL) and 10% ether/hexane (250 mL), 1.89 g of 2-acetoxy- 2,6-dimethyl-3,4,5,6-cyclohexadien-1-one as a bright yellow waxy solid which had: NMR δ6.80–6.76 (m, 2 H), 6.19–6.09 (m, 4 H), 2.05 (s, 3 H), 1.92 (d, J=0.8 Hz, 3 H), 1.36 (s, 3 H).

Preparation 24
1,3-Diacetoxy-2,4-dimethylbenzene

To a mixture of 2-acetoxy-2,6-dimethyl-3,4,5,6-cyclohexadien-1-one (the compound of Preparation 23, 0.5 g, 2.77 mmol) in acetic anhydride (1 mL) chilled to 0° C. was added boron trifluoride etherate (0.075 mL) slowly down the side of the flask. The reaction was stirred 15 min at 0° C., then it was warmed to ambient temperature and stirred 1 h more. Aqueous bicarbonate was added and the mixture was stirred vigorously for 30 min. The reaction was extracted with ether. The organic phase was washed with brine, dried over magnesium sulfate, and concentrated to yield 0.59 g (97%) of 1,3-diacetoxy-2,4-dimethylbenzene as a light yellow oil which had: NMR δ7.08 (d, J=8.2 Hz, 1 H), 6.87 (d, J=8.2 Hz, 1 H), 2.35 (s, 3 H), 2.32 (s, 3 H), 2.15 (s, 3 H), 1.98 (s, 3 H).

Preparation 25
1,3-Dihydroxy-2,4-dimethylbenzene

To a slurry of lithium aluminum hydride (0.56 g, 14.76 mmol) in ether (35 mL) was added 1,3-diacetoxy-2,4-dimethylbenzene (the compound of Preparation 24, 1.65 g, 7.42 mmol in 40 mL of ether) via syringe. The mixture was stirred overnight; then it was carefully quenched with sodium sulfate decahydrate (excess). The mixture was dried with anhydrous sodium sulfate, filtered, and concentrated to give 0.62 g (62%) of 1,3-dihydroxy-2,4-dimethylbenzene as a waxy light yellow solid which had: NMR δ6.83 (d, J=8 Hz, 1 H), 6.34 (d, J=8.1 Hz, 1 H), 4.71 (s, 2 H), 2.19 (s, 3 H), 2.17 (s, 3 H). There was also a small amount of an impurity observed in the NMR spectrum but the product was found to be suitable for use without further purification. The product was somewhat air sensitive and was used the same day it was synthesized.

Preparation 26
6,8-Dimethyl-7-hydroxychroman-4-one

A mixture of 1,3-dihydroxy-2,4-dimethylbenzene (the compound of Preparation 25, 0.62 g, 4.49 mmol), 3-chloropropionic acid (0.49 g, 4.52 mmol) and trifluoromethanesulfonic acid (2 mL) was heated to 80° C. for 2.25 h. The reaction was cooled and poured into chloroform. This mixture was extracted with water and this aqueous phase was back extracted with ether. The combined organic phase was washed with brine, dried over magnesium sulfate, and concentrated to give 2,4-dihydroxy-3,5-dimethyl-β-chloropropiophenone as a red oil.

The product of the above reaction was added to 50 mL of 2N sodium hydroxide which had been pre-cooled to 0° C. The mixture was stirred 2 h, then acidified to pH 1–2 with 6 N HCl and extracted with ethyl acetate (3x). The combined organic phase was washed with aqueous bicarbonate and brine, dried over magnesium sulfate, and concentrated to afford 0.55 g (64% for the two steps) of 6,8-dimethyl-7-hydroxychroman-4-one as an orange solid which had: NMR δ7.59 (s, 1 H), 5.45 (s, 1 H), 4.52 (t, J=6.4 Hz, 2 H), 2.74 (t, J=6.4 Hz, 2 H), 2.22 (s, 3 H), 2.13 (s, 3 H).

Preparation 27
6,8-Dimethyl-7-triisopropylsilyloxychroman-4-one

A mixture of 6,8-dimethyl-7-hydroxychroman-4-one (the compound of Preparation 26, 0.50 g, 2.60 mmol), imidazole (0.35 g, 5.14 mmol), and triisopropylsilyl chloride (0.61 mL, 2.85 mmol) in dimethylformamide (10 mL) was stirred at ambient temperature overnight. The reaction was diluted with water and extracted with ether (2x). The combined organic phase was washed with 1N lithium chloride (2x) and brine, dried over magnesium sulfate and concentrated. The residue was flash chromatographed on silica gel (1×4 inches packed in hexane) with elution proceeding as follows: 5% ethyl acetate/hexane (100 mL), nil; 5% ethyl acetate/hexane (100 mL) and 10% ethyl acetate/hexane (150 mL), 0.529 g (58%) of 6,8-dimethyl-7-triisopropylsilyloxychroman-4-one as a waxy lemon yellow solid which had: NMR δ7.57 (s, 1 H), 4.52 (t, J=6.4 Hz, 2 H), 2.74 (t, J=6.4 Hz, 2 H), 2.21 (s, 3 H), 2.11 (s, 3 H), 1.40–1.26 (m, 3 H), 1.13 (d, J=7.2 Hz, 18 H); $^{13}$C NMR δ191.60, 160.25, 159.93, 125.91, 122.55, 116.15, 115.29, 67.24, 37.52, 17.91, 17.69, 17.38, 14.24, 12.28, 9.97. A small silyl impurity was noted in the proton NMR at 1.06 ppm however, the material was found to be suitable for further transformations without additional purification.

Preparation 28
3,3-Dibromo-6,8-dimethyl-7-triisopropylsilyloxychroman-4-one To a solution of 6,8-dimethyl-7-triisopropylsilyloxychroman-4-one (the compound of Preparation 27, 0.50 g, 1.43 mmol) in carbon tetrachloride (10 mL) was added bromine (0.16 mL, 3.11 mmol in 5 mL of carbon tetrachloride) dropwise. The mixture was stirred 1 h at ambient temperature, then aqueous bisulfite was added and the mixture was stirred 30 min more. The phases were separated and the organic layer was washed with water and brine, dried over magnesium sulfate and concentrated to afford 0.64 g (89%) of 3,3-dibromo-6,8-dimethyl-7-triisopropylsilyloxychroman-4-one as an orange solid which had: NMR δ7.64 (s, 1 H), 4.68 (s, 2 H), 2.22 (s, 3 H), 2.13 (s, 3 H), 1.38–1.15 (m, 3 H), 1.11 (d, J=7.3 Hz, 18 H). Some minor impurities were noted in the NMR spectrum. However, the material was suitable for use without further purification.

Preparation 29
6-Fluoro-7-hydroxychroman-4-one

A mixture of 1,3-dimethoxybenzene (3.80 mL, 29.0 mmol) and N-fluorodibenzenesulfonamide (4.21 g, 29.21 mmol) was heated at 60° C. overnight. The mixture was cooled and flash chromatographed on silica gel (2×5 inches packed in hexane) with elution proceeding as follows: 3% ethyl acetate/hexane (1000 mL), discarded forerun; 3% ethyl acetate/hexane (1000 mL), 2.69 g of a 2:1 mixture of 2,4-dimethoxyfluorobenzene and starting material which was carried directly into the next step.

The product of the above reaction was combined with acetic acid (11 mL) and 48% HBr (11 mL) and refluxed 3 h.

The reaction was concentrated and flash chromatographed on silica gel (2×5 inches packed in hexane) with elution proceeding as follows: 10% ethyl acetate/hexane (2000 mL), 0.95 g (43%) of 2,4-dihydroxyfluorobenzene as a waxy white solid which was used without purification.

A mixture of 2,4-dihydroxyfluorobenzene (0.15 g, 1.17 mmol), 3-chloropropionic acid (0.13 g, 1.20 mmol) and trifluoromethanesulfonic acid (1 mL) were heated to 80° C. for 3 h. The reaction was poured into water and extracted with ether (3x). The combined organic phase was washed with water and brine, dried over magnesium sulfate, and concentrated to give 2,4-dihydroxy-5-fluoro-β-chloropropiophenone as a red solid which had: NMR δ7.37 (d, J=10.8 Hz, 1 H), 6.54 (d, J=7.7 Hz, 1 H), 3.87 (t, J=6.8 Hz, 2 H), 3.33 (t, J=6.8 Hz, 2 H). This product still contained some residual 3-chloropropionic acid but was suitable for use in the next reaction.

The product from the above reaction was combined with 2N sodium hydroxide (15 mL) and stirred overnight at ambient temperature. The reaction was acidified to pH 1–2 with 1 N HCl and extracted with ethyl acetate (3x). The combined organic phase was washed with water and brine, dried over magnesium sulfate and concentrated. The residue was flash chromatographed on silica gel (1×4 inches packed in hexane) with elution proceeding as follows: 25% ethyl acetate/hexane (300 mL), nil; 25% ethyl acetate/hexane (200 mL), 0.11 g (52% for the last two steps) of 6-fluoro-7-hydroxychroman-4-one as a white solid which had: mp 222–223° C.; NMR δ7.61 (d, J=10.3 Hz, 1 H), 6.58 (d, J=7.2 Hz, 1 H), 5.70–5.58 (m, 1 H), 4.51 (t, J=6.5 Hz, 2 H), 2.77 (t, J=6.4 Hz, 2 H).

Preparation 30
6-Fluoro-7-benzyloxychroman-4-one

A mixture of 6-fluoro-7-hydroxychroman-4-one (the compound of Preparation 29, 0.93 g, 5.11 mmol), benzyl bromide (0.61 mL, 5.13 mmol), potassium carbonate (1.41 g, 10.2 mmol) in acetone (100 mL) was stirred at ambient temperature overnight. The mixture was cooled, filtered, and concentrated to a yellow solid. This residue was recrystallized from ethyl acetate/ether to give 1.02 g (73%) of 6-fluoro-7-benzyloxychroman-4-one in two crops as cream white crystals which had: mp 155–156° C.; NMR δ7.58 (d, J=11 Hz, 1 H), 7.46–7.33 (m, 5 H), 6.54 (d, J=6.7 Hz, 1 H), 5.16 (d, 2 H), 4.50 (t, J=6.4 Hz, 2 H), 2.75 (t, J=6.4 Hz, 2 H). Analysis calculated for $C_{16}H_{13}FO_2$: C, 70.58; H, 4.81. Found: C, 70.45; H, 4.80.

Preparation 31
3,3-Dibromo-4-fluoro-7-benzyloxychroman-4-one

To a mixture of 6-fluoro-7-benzyloxychroman-4-one (the compound of Preparation 30, 0.99 g, 3.64 mmol) in carbon tetrachloride (45 mL) was added bromine (0.37 mL, 7.18 mmol in 5 mL of carbon tetrachloride) dropwise. The reaction was allowed to stir overnight at ambient temperature. Water was added to the reaction and 87 mg of an unidentified pink solid was collected by filtration and discarded. The phases were separated from the filtrate and the organic layer was washed with water, aqueous bicarbonate and brine, dried over magnesium sulfate, and concentrated to an air sensitive oil which was a mixture of brominated products and starting material (0.93 g). This material was combined with ethyl acetate (100 mL) and cupric bromide (0.6 g, 2.69 mmol) and refluxed 4 h. Cupric bromide (0.3 g, 1.35 mmol) was added and the reaction was refluxed overnight. Cupric bromide (0.6 g, 2.69 mmol) was added a third time and the reaction was continued at reflux overnight. The mixture was cooled, filtered, and concentrated. The residue was taken up in ethyl acetate and washed with water and brine, dried over magnesium sulfate and concentrated to give 0.91 g of a mixture of 3,3-dibromo-6-fluoro-7-benzyloxychroman-4-one and over brominated products. Key features from the NMR spectrum are signals at δ7.69(t, J=9.3 Hz), 7.63–7.32 (m), 6.62 (pair of d, J=5.7 and 7 Hz), 5.19 (s), 4.70 (s). This material was used crude for coupling experiments.

Preparation 32
6-Methyl-7-hydroxychroman-4-one

A mixture of 1,3-dihydroxy-4-methylbenzene (5.0 g, 40.3 mmol), 3-chloropropionic acid (4.38 g, 40.36 mmol) and trifluoromethanesulfonic acid (20 g) was heated to 80° C. overnight. The reaction was poured onto water and extracted with 1:1 ether/ethyl acetate (2x). The combined organic phase was washed with water (2x) and brine, dried over magnesium sulfate, and concentrated to an orange gum (7.6 g).

The gum from the above reaction was combined with 2 N sodium hydroxide (200 mL) and refluxed overnight. The mixture was acidified to pH 1–2 with 6 N HCl and extracted with ethyl acetate (3x). The combined organic phase was washed with water, aqueous bicarbonate (2x) and brine; then it was dried over magnesium sulfate and concentrated. The residue was flash chromatographed on silica gel (1.5×4 inches packed in hexane) with elution proceeding as follows: 10% ethyl acetate/hexane (500 mL), nil; 20% ethyl acetate/hexane (500 mL), nil; 30% ethyl acetate/hexane (500 mL), 3.1 g of a yellow solid. This material was recrystallized from ethyl acetate to give 1.66 g (23% over the two step sequence) of 6-methyl-7-hydroxychroman-4-one as a light pink solid which had: mp 185–186° C.; NMR δ7.66 (s, 1 H), 6.90 (br s, 1 H), 6.38 (s, 1 H), 4.45 (t, J=6.4 Hz, 2 H), 2.73 (t, J=6.4 Hz, 2 H), 2.17 (s, 3 H).

Preparation 33
6-Methyl-7-triisopropylsilyloxychroman-4-one

A mixture of 6-methyl-7-hydroxychroman-4-one (the compound of Preparation 32, 1.50 g, 8.42 mmol), imidazole (1.15 g, 16.9 mmol), and triisopropylsilyl chloride (2.0 mL, 9.2 mmol) in dimethylformamide (30 mL) was stirred overnight at ambient temperature. The reaction was poured into water and extracted with ether (2x). The combined organic layer was washed with 1 N lithium chloride (2x), dried over magnesium sulfate, and concentrated to afford 3.01 g (100%) of 6-methyl-7-triisopropylsilyloxychroman-4-one as a dull yellow oil which had: NMR δ7.64 (s, 1 H), 6.30 (s, 1 H), 4.45 (t, J=6.4 Hz, 2 H), 2.70 (t, J=6.4 Hz, 2 H), 2.14 (s, 3 H), 1.40–1.25 (m, 3 H), 1.09 (d, J=7.3 Hz, 18 H). The product also had a small silyl impurity and residual dimethylformamide present but was suitable for subsequent reaction.

Preparation 34
3,3-Dibromo-6-methyl-7-triisopropylsilyloxychroman-4-one and 6-Methyl-3,3,5-tribromo-triisopropylsilyloxychroman-4-one To a mixture of 6-methyl-7-triisopropylsilyloxychroman-4-one (the compound of Preparation 33, 3.0 g, 8.97 mmol) in carbon tetrachloride (70 mL) was added bromine (0.93 mL, 18.05 mmol in 20 mL of carbon tetrachloride) dropwise over 15 min. The reaction was stirred 1 h at ambient temperature and aqueous bisulfite was added. The reaction was stirred 15 min; then the phases were separated and the organic phase was washed with aqueous bicarbonate and brine, dried over magnesium sulfate and concentrated to an orange oil. This residue was flash chromatographed on silica gel (2×4 inches) with elution proceeding as follows: hexane (250 mL), nil; 3% ether/hexane (500 mL), nil; 3% ether/hexane (300 mL), 2.61 g of a mixture of 3,3-dibromo-6-methyl-7-triisopropylsilyloxychroman-4-one and 6-methyl-3,3,5-tribromo-7-triisopropylsilyloxychroman-4-one as a colorless oil (ratio of products was approximately 2.5:1). Key features of the NMR spectrum for 3,3-dibromo-6-methyl-7-triisopropylsilyloxychroman-4-one are $\delta 7.77$ (H at C-5), 6.38 (H at C-8), 4.68 (C-2 methylene), 2.19 (C-6 methyl).

Preparation 35
3-Trifluoromethanesulfonyloxy-8-methyl-8-azabicyclo-(3.2.1)-octane Tropine (14.2 g, 0.10 mol) was dissolved in methylene chloride (210 mL) and triethylamine (23 mL, 0.16 mol). Trifluoromethanesulfonyl chloride (9.3 mL, 0.12 mol) was added dropwise at a rate such that the methylene chloride boiled gently. The reaction was stirred at ambient temperature for 1 h; then it was washed with cold 0.5 N sodium hydroxide, water, and brine. The organic phase was dried and concentrated to a yellow solid which had: NMR $\delta 4.88$ (t, 1 H), 3.10–3.05 (m, 2 H), 2.94 (s, 3 H), 2.22 (s, 3 H), 2.20–2.10 (m, 2 H), 2.02–1.88 (m, 6 H).

Preparation 36
3-(4-Fluorophenylsulfanyl)-8-methyl-8-azabicyclo-(3.2.1)-octane

In a 3 neck round bottom flask equipped for overhead mechanical stirring sodium hydride (2.02 g, 50.47 mmol, 60% oil dispersion) was rinsed free of oil with hexane (2 washes) and tetrahydrofuran (225 mL) was added followed by 4-fluorothiophenol (4.89 mL, 45.89 mmol in 30 mL of tetrahydrofuran with a 20 mL rinse). Hydrogen gas freely evolved from the reaction. Upon cessation of hydrogen evolution, 3-trifluoromethanesulfonyloxy-8-methyl-8-azabicyclo-(3.2.1)-octane (the compound of Preparation 35, 9.42 g, 45.89 mmol) was added all at once neat as a solid with a 50 mL tetrahydrofuran rinse. The reaction was refluxed overnight, then cooled. The solvent was removed at reduced pressure and residue was taken up in ethyl acetate. The organic phase was washed with water and brine, dried over calcium sulfate and concentrated to afford 8.28 g (72%) of 3-(4-fluorophenylsulfanyl)-8-methyl-8-azabicyclo-(3.2.1)-octane as a tan oil which had: NMR $\delta 7.38$ (dd, J=5, 9 Hz, 2 H), 6.96 (long range coupled t, J=9 Hz, 2 H), 3.22–3.08 (m, 3 H), 2.23 (s, 3 H), 2.02–1.94 (m, 2 H), 1.83–1.64 (m, 4 H), 1.50 (ABq, $\Delta v_{1-3}$=14.5 Hz, J=6.5 Hz, 2 H).

Preparation 37
3-(4-Fluorophenylsulfanyl)-8-(2,2,2-trichloroethoxycarbonyl)-8-azabcyclo-(3.2.1)-octane A mixture of 3-(4-fluorophenylsulfanyl)-8-methyl-8-azabicyclo-(3.2.1)-octane (the compound of Preparation 36, 8.20 g, 32.65 mmol), 2,2,2-trichloroethyl chloroformate (4.94 mL, 35.92 mmol), and potassium carbonate (4.96 g, 35.92 mmol) in benzene (140 mL) was refluxed overnight. The solvent was removed at reduced pressure and the residue was taken up in ethyl acetate. The organic phase was washed with aqueous bicarbonate and brine, dried over calcium sulfate and concentrated. The residue was flash chromatographed on silica gel (3×4 inches) with elution proceeding as follows: hexane (350 mL), nil; 10% ethyl acetate/hexane (400 mL), discarded forerun; 10% ethyl acetate/hexane (600 mL), 20% ethyl acetate/hexane (500 mL), and 30% ethyl acetate/hexane (250 mL), 10.32 g (77%) of 3-(4-fluorophenylsulfanyl)-8-(2,2,2-trichloroethoxycarbonyl)-8-azabicyclo-(3.2.1)-octane as an off white solid which had: mp 65–67° C.; NMR $\delta 7.40$ (dd, J=5.5, 9 Hz, 2 H), 6.98 (long range coupled t, J=8.5 Hz, 2 H), 4.72 (ABq, $\Delta v_{1-3}$=60 Hz, J=12 Hz, 2 H), 4.35 (sym m, 2 H), 3.32 (septet, J=6 Hz, 1 H), 2.10–1.94 (m, 2 H), 1.94–1.58 (m, 6 H).

Preparation 38
3-(4-Fluorophenylsulfanyl)-8-azabicyclo-(3.2.1)-octane

A mixture of 3-(4-fluorophenylsulfanyl)-8-(2,2,2-trichloroethoxycarbonyl)-8-azabicyclo-(3.2.1)-octane (the compound of Preparation 37, 10.28 g, 24.92 mmol), 48% HBr (20 mL), and acetic acid (80 mL) was heated to 110° C. for 78 h. The reaction was adjusted to pH 11 by addition of 4 N sodium hydroxide and extracted with methylene chloride. The organic phase was filtered through Diatomaceous earth, washed with brine, dried over calcium sulfate and concentrated. The residue was kugelrohr distilled (110° C. (pot temperature), 1.5 mm Hg) to give 3.30 g of 3-(4-fluorophenylsulfanyl)-8-azabicyclo-(3.2.1)-octane as a yellow oil which had NMR $\delta 7.41$ (dd, J=5.5, 9 Hz, 2 H), 7.00 (long range coupled t, J=8.5 Hz, 2 H), 4.11 (s, impurity), 3.55 (br t, J=3.5 Hz, 2 H), 3.24 (sym m, 1 H), 2.58 (br s, 2 H, exchanges with $D_2O$, should integrate for 1 H), 1.90–1.77 (m, 4 H), 1.70–1.51 (m, 4 H). This product was suitable for use without further purification.

Preparation 39
3-(4-Chlorophenylsulfanyl)-8-methyl-8-azabicyclo-(3.2.1)-octane

In a 3 neck round bottom flask equipped for overhead mechanical stirring sodium hydride (2.03 g, 50.91 mmol, 60% oil dispersion) was rinsed free of oil with hexane (2 washes) and tetrahydrofuran (200 mL) was added followed by 4-chlorothiophenol (6.69 g, 46.28 mmol in 20 mL of tetrahydrofuran). Hydrogen gas freely evolved from the reaction. Upon cessation of hydrogen evolution, 3-trifluoromethanesulfonyloxy-8-methyl-8-azabicyclo-(3.2.1)-octane (9.5 g, 46.28 mmol in 70 mL of tetrahydrofuran) was added. The reaction was refluxed overnight, then cooled and filtered through Diatomaceous earth (with ether rinse). The filtrate was concentrated at reduced pressure and residue was taken up in ether. The organic phase was washed with water and brine, dried over calcium sulfate and concentrated to afford 8.08 g (65%) of 3-(4-chlorophenylsulfanyl)-8-methyl-8-azabicyclo-(3.2.1)-octane as a tan oil which had: NMR $\delta 7.42$–7.23 (m, 4 H), 3.22 (sym m, 1 H), 3.20–3.11 (m, 2 H), 2.24 (s, 3 H), 2.03–1.97 (m, 2 H), 1.82–1.66 (m, 4 H), 1.53 (ABq, $\Delta v_{1-3}$=14.5 Hz, J=6.5 Hz, 2 H).

Preparation 40
3-(4-Chlorophenylsulfanyl)-8-(2,2,2-trichloroethoxycarbonyl)-8-azabicyclo-(3.2.1)-octane A mixture of 3-(4-chlorophenylsulfanyl)-8-methyl-8-azabicyclo-(3.2.1)-octane (8.06 g, 30.12 mmol), 2,2,2-trichloroethyl chloroformate (4.56 mL, 33.13 mmol), and potassium carbonate (4.58 g, 33.13 mmol) in benzene (150 mL) was refluxed overnight. The solvent was removed at reduced pressure and the residue was taken up in ethyl acetate. The organic phase was washed with aqueous bicarbonate and brine, dried over calcium sulfate and concentrated. The residue was flash chromatographed on silica gel (3×4 inches) with elution proceeding as follows: hexane (350 mL), nil; 10% ethyl acetate/hexane (500 mL), discarded forerun; 10% ethyl acetate/hexane (500 mL), 20% ethyl acetate/hexane (500 mL), and 30% ethyl acetate/hexane (250 mL), 9.26 g (72%) of 3-(4- chlorophenylsulfanyl)-(2,2,2-trichloroethoxycarbonyl)-8-azabicyclo-(3.2.1)-octane as a yellow solid which had: mp 70–71.5° C.; NMR δ7.33 (long range coupled d, J=8.5 Hz, 2 H), 7.26 (long range coupled δ, J=8.5 Hz, 2 H), 4.73 (ABq, $\Delta v_{1-3}$=58 Hz, J=12 Hz, 2 H), 4.43–4.30 (m, 2 H), 3.40 (septet, J=6 Hz, 1 H), 2.10–1.56 (m, 8 H).

Preparation 41
3-(4-Chlorophenylsulfanyl)-8-azabicyclo-(3.2.1)-octane

A mixture of 3-(4-chlorophenylsulfanyl)-8-(2,2,2-trichloroethoxycarbonyl)-8-azabicyclo-(3.2.1)-octane (8.70 g, 20.28 mmol), 48% HBr (17 mL), and acetic acid (68 mL) was heated to 110° C. for 78 h. The reaction was adjusted to pH 11 by addition of 4 N sodium hydroxide and extracted with methylene chloride. The organic phase was filtered through diatomaceous earth, washed with brine, dried over calcium sulfate and concentrated to afford 3-(4-chlorophenylsulfanyl)-8-azabicyclo-(3.2.1)-octane as a yellow oil. The product was kugelrohr distilled (110–130° C., (pot temperature), 1.5 mm Hg) to give 4.1 g (79%) of 3-(4-chlorophenylsulfanyl)-8-azabicyclo-(3.2.1)-octane as a nearly colorless oil which solidified and had: NMR δ7.30 (m, 4 H), 3.54 (br t, J=3.5 Hz, 2 H), 3.32 (sym m, 1 H), 1.97–1.72 (m, 5 H), 1.71–1.52 (m, 4 H).

Preparation 42
1-(2,2-Diphenyl-benzo(1,3)dioxol-5-yl)-propan-1-one

A mixture of 3,4-dihydroxypropiophenone (ICN Biomedicals, Inc., 3300 Hyland Ave., Costa Mesa, Calif., 92626, USA, 5.0 g, 30 mmol) and dichlorodiphenylmethane (10.0 mL, 52.1 mmol) was heated for 7 min at 170° C. The reaction was cooled and poured into 1 N sodium hydroxide. The mixture was extracted with ether (2×) and the combined extracts were washed with water and brine. The organic layer was dried over magnesium sulfate and concentrated. The residue was flash chromatographed on silica gel (2×5 inches packed in hexane) with elution proceeding as follows: 2% ether/hexane (500 mL), 0.84 g of a white solid tentatively identified as 2-chloro-1-(2,2-diphenyl-benzo(1,3)dioxol-5-yl)-propan-1-one; 5% ether/hexane (250 mL), 1.9 g of an unidentified orange oil; 5% ether/hexane (250 mL), 2.18 g of recovered dichlorodiphenylmethane; 10% ether/hexane (500 mL), 4.82 g (48%) of 1-(2,2-diphenyl-benzo(1,3)dioxol-5-yl)-propan-1-one as an orange oil which solidified on standing. The product had: mp 69–70.5° C. Analysis calculated for $C_{22}H_{17}ClO_3$: C, 79.98; H, 5.49. Found: C, 80.05; H, 5.34.

Preparation 43
2-Bromo-1-(2,2-diphenyl-benzo(1,3)dioxol-5yl)-propan-1-one 1-(2,2-Diphenyl-benzo(1,3)dioxol-5-yl)-propan-1-one (the compound of Preparation 42, 4.70 g, 14.23 mmol) was dissolved in carbon tetrachloride (60 mL) and bromine (0.74 mL, 14.36 mmol in 10 mL of carbon tetrachloride) was added dropwise. The reaction was stirred at ambient temperature 30 min and then it was extracted with saturated aqueous bicarbonate solution. The organic phase was washed with water and brine, dried over magnesium sulfate, and concentrated to afford 5.58 g (96%) of 2-bromo-1-(2,2-diphenyl-benzo(1,3)dioxol-5-yl)-propan-1-one as a dark orange oil which had: NMR δ7.68–7.37 (m, 12 H), 6.95 (d, J=8.3 Hz, 1 H), 5.21 (q, J=6.7 Hz, 1 H), 1.88 (d, J=6.6 Hz, 3 H).

Preparation 44
4-Benzyloxy-3-hydroxypropiophenone

A mixture of 3,4-dihydroxypropiophenone (ICN Biomedicals, Inc., 3300 Hyland Ave., Costa Mesa, Calif., 92626, USA, 2.00 g, 12.0 mmol), benzyl bromide (1.43 mL, 12.0 mmol), and potassium carbonate (3.33 g, 24.1 mmol) in acetone (100 mL) was refluxed 24 h. The reaction was cooled and filtered. The filtrate was concentrated and the residue was partitioned between ethyl acetate and 0.25 N hydrochloric acid. The phases were separated and the organic layer was washed with water and brine, dried over magnesium sulfate, and concentrated. The residue was flash chromatographed on silica gel (1×5 inches packed in hexane) with elution proceeding as follows: 10% ethyl acetate/hexane (500 mL), nil; 30% ethyl acetate/hexane (1000 mL), 0.88 g (28%) of 4-benzyloxy-3-hydroxypropiophenone as a white solid which had: NMR δ7.58–7.52 (m, 2 H), 7.44–7.36 (m, 5 H), 6.96 (d, J=8.2 Hz, 1 H), 5.72 (s, 1 H), 5.19 (s, 2 H), 2.94 (q, J=7.2 Hz, 2 H), 1.21 (t, J=7.3 Hz, 3 H).

Preparation 45
4-Benzyloxy-3-methoxypropiophenone

A mixture of 4-benzyloxy-3-hydroxypropiophenone (the compound of Preparation 44, 0.88 g, 3.43 mmol), potassium carbonate (0.95 g, 6.87 mmol), and methyl iodide (0.50 mL, 8.0 mmol) in acetone (50 mL) was refluxed 2 h and allowed to stir at ambient temperature over the weekend. The reaction was filtered and the filtrate was concentrated. The residue was partitioned between ether and water. The phases were separated and the organic phase was washed with water and brine, dried over magnesium sulfate, and concentrated to afford 0.88 g (95%) of 4-benzyloxy-3-methoxypropiophenone as a white solid which had: NMR δ7.55 (d, J=2 Hz, 1 H), 7.50 (dd, J=2, 8.4 Hz, 1 H), 7.44–7.28 (m, 5 H), 6.87 (d, J=8.4 Hz, 1 H), 5.22 (s, 2 H), 3.93 (s, 3 H), 2.93 (q, J=7.3 Hz, 2 H), 1.20 (t, J=7.3 Hz, 3 H).

Preparation 46
4-Benzyloxy-α-bromo-3-methoxypropiophenone

4-Benzyloxy-3-methoxypropiophenone (the compound of Preparation 45, 0.84 g, 3.11 mol) was dissolved in carbon tetrachloride (20 mL) and bromine (0.16 mL, 3.11 mmol in 5 mL of carbon tetrachloride) was added over 10 min. The reaction was stirred for 30 min at ambient temperature. The reaction was poured into saturated aqueous bicarbonate and the phases were separated. The organic layer was washed with water and brine, dried over magnesium sulfate and concentrated. The residue was taken up in ether and concentrated and this process was repeated to remove residual carbon tetrachloride from the product. In this manner 1.12 g (100%) of 4-benzyloxy-α-bromo-3-methoxypropiophenone was obtained as a waxy light orange solid which had: NMR δ7.58–7.54 (m, 3 H), 7.42–7.23 (m, 4 H), 6.89 (d, J=8.3 Hz, 1 H), 5.25–5.21 (m, 3 H), 3.93 (s, 3 H), 1.85 (d, J=6.6 Hz, 3 H).

Preparation 47
4-(3,5-Dibromophenyl)-4-hydroxy-piperidine hydrochloride

A solution of 1,3,5-tribromobenzene (15.75 g, 50.0 mmol) in ether (500 mL) was chilled to −78° C. and butyllithium (20.8 mL, 50.0 mmol, 2.4 M in hexane) was added dropwise over 30 min. The reaction was stirred 30 min and then 1-tert-butyloxycarbonylpiperidin-4-one (5.0 g, 25 mmol in 100 mL of ether) was added dropwise over 30 min. with a 20 mL ether rinse. The reaction was stirred 2 h at −78° C., then the reaction was quenched with water and allowed to warm to ambient temperature. The phases were separated and the organic layer was washed with brine, dried over calcium sulfate and concentrated. The residue was flash chromatographed on silica gel (4×4 inches) with elution proceeding as follows: 1% ethyl acetate/hexane (1000 mL), nil; 5% ethyl acetate/hexane (1000 mL) and 10% ethyl acetate/hexane (1000 mL), unweighed mixture of starting tribromide and 1,3 dibromobenzene; 10% ethyl acetate/hexane (1000 mL), nil; 15% ethyl acetate/hexane (2000 mL), nil; 20% ethyl acetate/hexane (2000 mL), 6.76 g (62%) of 4-(3,5-dibromophenyl)-4-hydroxy-1-tert-butyloxycarbonylpiperidine as a light yellow foam which had: NMR δ7.56 (m, 3 H), 4.06 (br d, J=13 Hz, 2 H), 3.21 (t, J=13 Hz, 2 H), 1.93 (dt, J=4.5, 13 Hz, 2 H), 1.80 (s, 1 H), 1.68 (d, J=13 Hz, 2 H), 1.48 (s, 9 H). The product was estimated to be 88% pure and contaminated by 12% of 1-tert-butyloxycarbonylpiperidin-4-one (NMR triplets at δ3.71 and 2.44). This material was suitable for use without further purification.

The product of the above reaction (6.76 g, 15.5 mmol) was dissolved in ether (150 mL) and dioxane saturated with HCl (15 mL) was added. The mixture was stirred 30 min at ambient temperature, then chilled to 0° C. and HCl gas was bubbled into the solution for 3 min. The reaction was allowed to warm to ambient temperature and stir overnight. Nitrogen gas was bubbled through the mixture to remove HCl gas and the precipitate was filtered to afford 3.27 g of a cream colored solid. The filtrate was again saturated with HCl gas and stirred 6 h. Again the mixture was purged with nitrogen gas and the precipitate collected (1.63 g). The HCl hydrolysis was repeated a third time to yield 0.45 g more product. In this fashion 5.45 g (94%) 4-(3,5-dibromophenyl)-4-hydroxypiperidine hydrochloride was obtained as a cream colored solid. This material was used without purification.

Preparation 48

(1R*,2R*)-1-(4-Hydroxyphenyl)-2-(4-(3,5-dibromophenyl)-4-hydroxypiperidin-1-yl)-propan-1-ol A mixture of 4-triisopropylsilyloxy-α-bromopropiophenone (3.0 g, 7.79 mmol), 4-(3,5-dibromophenyl)-4-hydroxypiperidine hydrochloride (the compound of Preparation 47, 2.89 g, 7.79 mmol) and triethylamine (3.26 mL, 23.4 mmol) in ethanol (200 mL) was refluxed overnight. The solvent was removed at reduced pressure and the residue was partitioned between ethyl acetate and water. The phases were separated and the organic layer was washed with brine, dried over calcium sulfate and concentrated. The residue was flash chromatographed on silica gel (2×4 inches) with elution proceeding as follows: 1% ethyl acetate/hexane (500 mL), nil; 5% ethyl acetate/hexane (300 mL), unweighed starting ketone; 5% ethyl acetate/hexane (700 mL) and 15% ethyl acetate/hexane (300 mL), nil; 15% ethyl acetate/hexane (1200 mL), 3.55 g (71%) of 1-(4-triisopropylsilyloxyphenyl)-2-(4-(3,5-dibromophenyl)-4-hydroxypiperidin-1-yl)-propan-1-one as a crunchy off white foam which had: NMR δ8.03 (d, J=9 Hz, 2 H), 7.57–7.53 (m, 3 H), 6.92 (d, J=8.5 Hz, 2 H), 4.14 (q, J=7 Hz, 1 H), 2.85 (dd, J=2, 9.5 Hz, 2 H), 2.77–2.70 (m, 1 H), 2.60 (dt, J=2.5, 11.5 Hz, 1 H), 2.13–1.92 (m, 2 H), 1.74–1.56 (m, 3 H), 1.32 (d, J=7 Hz, 3 H), 1.36–1.18 (m, 3 H), 1.12 (d, J=7 Hz, 18 H).

An ice cold mixture of sodium borohydride (0.21 g, 5.56 mmol) and ethanol (50 mL) was stirred 10 min and then 1-(4-triisopropylsilyloxyphenyl)-2-(4-(3,5-dibromophenyl)-4-hydroxypiperidin-1-yl)-propan-1-one (3.55 g, 5.56 mmol in 50 mL of ethanol) was added dropwise over 15 min. The reaction was allowed to warm to ambient temperature and stir overnight. Additional sodium borohydride (0.10 g) was added and the reaction was stirred 6 h more. The white precipitate was collected and rinsed with ethanol and weighed 0.84 g. The filtrate was treated with sodium borohydride (0.10 g) and stirred overnight. The white precipitate was collected and rinsed with ethanol and weighed 2.56 g. The combined precipitate (3.40 g) was recrystallized from ethanol to afford 3.0 g (84%) of (1R*,2R*)-1-(4-triisopropylsilyloxyphenyl)-2-(4-(3,5-dibromophenyl)-4-hydroxypiperidin-1-yl)-propan-1-ol as fluffy white needles which had: mp 235–236.5° C. Analysis calculated for $C_{29}H_{43}Br_2NO_3Si$: C, 54.29; H, 6.76; N, 2.18. Found: C, 54.17; H, 6.50; N, 2.35.

The product of the above reaction (0.53 g, 0.827 mmol) was dissolved in tetrahydrofuran (20 mL) and tetrabutylammonium fluoride (1.25 mL, 1.25 mmol, 1 M tetrahydrofuran solution) was added. The reaction was stirred 1 h at ambient temperature and then concentrated. The residue was flash chromatographed on silica gel (1.5×3 inches) with elution proceeding as follows: 25% ethyl acetate/hexane (600 mL), unweighed forerun; 25% ethyl acetate/hexane (200 mL), nil; 25% ethyl acetate/hexane (200 mL) and 50% ethyl acetate/hexane (800 mL), 0.20 g, (50%) of (1R*, 2R*)-1-(4-hydroxyphenyl)-2-(4-(3,5-dibromophenyl)-4-hydroxypiperidin-1-yl)-propan-1-ol as a white solid which had: mp 232–234° C. Analysis calculated for $C_{20}H_{23}Br_2NO_3$: C, 49.51; H, 4.78; N, 2.89. Found: C, 49.77; H, 4.58; N, 2.76.

Preparation 49

1R*,2R*1-(4-Hydroxyphenyl)-2-(4-(3,5-ditritiophenyl-4-hydroxypiperidin-yl)-propan-1-ol To a solution of (1R*,2R*)-1-(4-hydroxyphenyl)-2-(4-(3,5-dibromophenyl)-4-hydroxypiperidin-1-yl)-propan-1-ol (the compound of Preparation 48, 0.015 g, 0.031 mmol) in dioxane (3 mL) was added 10% palladium on carbon (0.013 g) and triethylamine (0.015 mL). The reaction mixture was freeze/thaw degassed three times and then exposed to tritium gas (15 curies) for 6 h at ambient temperature. The reaction was filtered through diatomaceous earth and the pad washed well with methanol (3 mL). The filtrate was concentrated. The residue was diluted with methanol (1 mL) and concentrated to remove any labile tritium impurities. This dilution/evaporation process was repeated three times. The residue was dissolved in ethanol (20 mL) and filtered through a Teflon syringe filter to afford 913 mCi of activity. The entire lot was purified by chromatography on silica gel (2.5×8 cm) eluting with ethyl acetate to afford 156 mCi of (1R*,2R*)-1-(4-Hydroxyphenyl)-2-(4-(3,5-ditritiophenyl)-4-hydroxypiperidin-yl)-propan-1-ol which had a radiochemical purity of >98% and a specific activity of 42.8 Ci/mmol.

Preparation 50

3,5-Dimethyl-4-hydroxypropiophenone

A mixture of 2,6-dimethylphenol (10.5 g, 85.9 mmol), propionic acid (4.64 mL, 86.8 mmol), and trifluoromethanesulfonic acid (59 g) was heated to 80° C. for 48 h. The reaction was cooled, poured onto ice, and extracted with chloroform. The organic extracts were washed with saturated aqueous bicarbonate and brine, dried, and concentrated to a dark oily solid. This material was Kugelrohr distilled 105–135° C. (1.5 mm Hg, pot temperature) to afford 11.2 g (73%) of 3,5-dimethyl-4-hydroxypropiophenone as a solid which had: NMR δ7.63 (s, 2 H), 5.30 (s, 1 H), 2.92 (q, J=7.5 Hz, 2 H), 2.27 (s, 6 H), 1.18 (t, J=7.5 Hz, 3 H).

Preparation 51

4-Benzyloxy-3,5-dimethylpropiophenone

A mixture of 3,5-dimethyl-4-hydroxypropiophenone (11.2 g, 62.9 mmol), benzyl bromide (8.23 mL, 69.2 mmol), and potassium carbonate (17.4 g, 125.8 mmol) in acetone (200 mL) was stirred overnight. The mixture was filtered and the solvent was removed. The residue was partitioned between ethyl acetate and water. The phases were separated and the organic layer was washed with brine, dried over calcium sulfate and concentrated. The residue was flash chromatographed on silica gel (2.5×3.5 inches packed with hexane) and eluted as follows: 5% ethyl acetate/hexane (700 mL), nil; 7% ethyl acetate/hexane (400 mL) and 10% ethyl acetate/hexane (1500 mL), 15.33 g (91%) of 4-benzyloxy-3,5-dimethylpropiophenone as a light yellow solid which had: mp 67–68.5° C.; NMR δ7.66 (s, 2 H), 7.47–7.32 (m, 5 H), 4.83 (s, 2 H), 2.95 (q, J=7.5 Hz, 2 H), 2.32 (s,6 H), 1.20 (t, J=7.5 Hz, 3 H).

Preparation 52
4-Benzyloxy-α-bromo-3,5-dimethylpropiophenone

To a solution of 4-benzyloxy-3,5-dimethylpropiophenone (15.19 g, 56.6 mmol) in carbon tetrachloride (160 mL) was added bromine (2.98 mL, 57.8 mmol in 40 mL of carbon tetrachloride) dropwise. The reaction was stirred 15 min after the addition was completed and then aqueous sodium sulfite was added and the mixture was stirred 30 min more. The phases were separated and the organic layer was washed with saturated aqueous bicarbonate and brine, dried, and concentrated to afford 19.55 g (99%) of 4-benzyloxy-α-bromo-3,5-dimethylpropiophenone as a yellow solid which was suitable for use without purification and had: NMR δ7.72 (s, 2 H), 7.52–7.30 (m, 5 H), 5.27 (q, J=6.5 Hz, 1 H), 4.85 (s, 2 H), 2.33 (s, 6 H), 1.88 (d, J=6.5 Hz, 3 H).

What is claimed is:

1. A method of treating Parkinson's Disease in a mammal comprising administering to said mammal a Parkinson's Disease treating synergistic effective amounts of a combination of (+)-(1S,2S)-1-(4-hydroxy-phenyl)-2-(4-hydroxy-4-phenylpiperidino)-1-propanol and levodopa.

2. A pharmaceutical composition comprising a Parkinson's Disease treating synergistic effective amounts of a combination of (+)-(1S,2S)-1-(4-hydroxy-phenyl)-2-(4-hydroxy-4-phenylpiperidino)-1-propanol and levodopa; and a pharmaceutically acceptable diluent or carrier.

3. A method for achieving a synergistic antiparkinson effect in a mammal in need thereof which comprises administering to said mammal synergistic effective amounts of two therapeutic agents:

(a) a forebrain selective NMDA antagonist, wherein said NMDA antagonist is (+)-(1S,2S)-1-(4-hydroxy-phenyl)-2-(4-hydroxy-4-phenylpiperidino)-1-propanol; and (b) an excitatory feedback enhancing agent, wherein said excitatory feedback enhancing agent is levodopa, wherein the amount of (a) alone and the amount of (b) alone is insufficient to achieve the therapeutic effect; and wherein the combined effect of the amounts of the therapeutic agents administered is greater than the sum of the therapeutic effects of the amounts of the individual therapeutic agents separately administered.

4. A method of claim 3 wherein an amount of a forebrain selective NMDA antagonist and an amount of an excitatory feedback enhancing agent are administered simultaneously.

5. A method of claim 3 wherein an amount of a forebrain selective NMDA antagonist and an amount of an excitatory feedback enhancing agent are administered sequentially in any order.

* * * * *